US010381107B2

(12) United States Patent
Smolyanitsky

(10) Patent No.: US 10,381,107 B2
(45) Date of Patent: Aug. 13, 2019

(54) NUCLEIC ACID SEQUENCER FOR ELECTRICALLY DETERMINING A SEQUENCE OF NITROGENOUS BASES IN A SINGLE STRANDED NUCLEIC ACID

(71) Applicant: The United States of America, as Represented by the Secretary of Commerce, Washington, DC (US)

(72) Inventor: Alex Smolyanitsky, Boulder, CO (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 161 days.

(21) Appl. No.: 15/599,076

(22) Filed: May 18, 2017

(65) Prior Publication Data
US 2018/0157790 A1   Jun. 7, 2018

Related U.S. Application Data

(60) Provisional application No. 62/430,097, filed on Dec. 5, 2016.

(51) Int. Cl.
*C12Q 1/6825* (2018.01)
*G01N 33/487* (2006.01)
(Continued)

(52) U.S. Cl.
CPC ............ *G16B 30/00* (2019.02); *B01L 3/5027* (2013.01); *C12Q 1/6806* (2013.01); *C12Q 1/689* (2013.01); *G01N 33/48721* (2013.01); *C12P 19/34* (2013.01); *C12Q 1/6825* (2013.01); *C12Q 1/6869* (2013.01)

(58) Field of Classification Search
None
See application file for complete search history.

(56) References Cited

U.S. PATENT DOCUMENTS

2013/0256139 A1   10/2013   Peng
2013/0256154 A1   10/2013   Peng
(Continued)

FOREIGN PATENT DOCUMENTS

WO   WO-2011046706 A1 *   4/2011   ............. B82Y 30/00

OTHER PUBLICATIONS

Wei et al, Nanolett., vol. 13, pp. 26-30, published online Dec. 5, 2012.*
(Continued)

*Primary Examiner* — Robert T. Crow
(74) *Attorney, Agent, or Firm* — Office of Chief Counsel for National Institute of Standards and Technology

(57) ABSTRACT

A nucleic acid sequencer includes: an atomically thin membrane; a solid electrode spaced apart from the atomically thin membrane and arranged in a capacitive configuration with the atomically thin membrane; a spacer member; a complementary base covalently disposed on the atomically thin membrane and arranged to base pair with a nitrogenous base of the single stranded nucleic acid; a power source in electrical communication with the solid electrode and that provides electrical power to the solid electrode; and a resistor in electrical communication with the power source and that receives electric current from the power source and that also is in electrical communication with the atomically thin membrane such that an amount of the electric current changes in response to a change in the selected distance between the atomically thin membrane and the solid electrode.

20 Claims, 37 Drawing Sheets
Specification includes a Sequence Listing.

(51) Int. Cl.
  *G16B 30/00*   (2019.01)
  *C12Q 1/6806*  (2018.01)
  *B01L 3/00*    (2006.01)
  *C12Q 1/689*   (2018.01)
  *C12Q 1/6869*  (2018.01)
  *C12P 19/34*   (2006.01)

(56) References Cited

U.S. PATENT DOCUMENTS

| 2014/0045270 A1* | 2/2014 | Shim | G01N 33/50 436/94 |
| 2014/0174927 A1* | 6/2014 | Bashir | C12Q 1/6827 204/452 |
| 2015/0028846 A1* | 1/2015 | Zhu | G01N 27/3275 324/71.5 |

OTHER PUBLICATIONS

Paulechka, E., et al., "Nucleobase-functionalized graphene nanoribbons for accurate high-speed DNA sequencing", Publication online arXiv.org https://arxiv.org/abs/1509.04778, Sep. 16, 2015.

Prasongkit, A., et al., "Theoretical Study of Electronic Transport through DNA Nucleotides in a Double-Functionalized Graphene Nanogap", J. Phys. Chem., on-line publication, Jul. 8, 2013, pp. 15421-15428, vol. 117, No. 29. American Chemical Society, United States.

Liu, J., et al., "Atomically Thin Molybdenum Disulfide Nanopores with High Sensitivity for DNA Translocation", ACSNANO, on-line publication, Feb. 18, 2014, pp. 2504-2511, vol. 8; No. 3. American Chemical Society, United States.

Schneider, G., et al., "DNA translocation through graphene nanopores", NANO Letters, on-line publication, Jul. 7, 2010, pp. 3163-3167, vol. 10; No. 8. American Chemical Society, United States.

Merchant, C., et al., "DNA Translocation through graphene nanopores", NANO Letters, on-line publication, Jul. 23, 2010, pp. 2915-2921, vol. 10; No. 8. American Chemical Society, United States.

Farimani, A., et al., "DNA Base Detection Using a Single-Layer MoS2", ACSNANO, on-line publication, Jul. 9, 2014, pp. 7914-7922, vol. 8; No. 8. American Chemical Society, United States.

Feng, J., et al., "Identification of single nucleotides in MoS2 nanopores", Nature Nanotechnology, on-line publication, Sep. 21, 2015, pp. 1070-1076, vol. 10.

* cited by examiner (A)

(B)

cytosine (C)  guanine (G)

(B)  thymine (T)  adenine (A)

NUCLEIC ACID SEQUENCER FOR ELECTRICALLY DETERMINING A SEQUENCE OF NITROGENOUS BASES IN A SINGLE STRANDED NUCLEIC ACID

CROSS REFERENCE TO RELATED APPLICATIONS

This application claims the benefit of U.S. Provisional Patent Application Ser. No. 62/430,097, filed Dec. 5, 2016, the disclosure of which is incorporated herein by reference in its entirety.

STATEMENT REGARDING FEDERALLY SPONSORED RESEARCH

This invention was made with United States Government support from the National Institute of Standards and Technology, an agency of the United States Department of Commerce. The Government has certain rights in the invention.

SEQUENCE LISTING

This application contains a Sequence Listing electronically submitted via EFS-web to the United States Patent and Trademark Office as a text file named "17-006us1_Sequence_Listing_FINAL_8-9-17.txt." The Sequence Listing serves as a paper required by 37 C.F.R. § 1.821 (c) and a computer readable form required by 37 C.F.R. § 1.821 (e). The sequence listing information recorded in computer readable form is identical to the written sequence listing. The information contained in the Sequence Listing is incorporated by reference herein in its entirety.

BRIEF DESCRIPTION

Disclosed is a nucleic acid sequencer to electrically determine a sequence of nitrogenous bases in a single stranded nucleic acid, the nucleic acid sequencer comprising: an atomically thin membrane; a solid electrode spaced apart from the atomically thin membrane and arranged in a capacitive configuration with the atomically thin membrane; a spacer member interposed between the atomically thin membrane and the solid electrode and comprising: a first surface on which the atomically thin membrane is disposed; and a second surface on which the solid electrode is disposed, such that the spacer member provides a selected distance between the atomically thin membrane and the solid electrode; a complementary base covalently disposed on the atomically thin membrane and arranged to base pair with a nitrogenous base of the single stranded nucleic acid; a power source in electrical communication with the solid electrode and that provides electrical power to the solid electrode; and a resistor in electrical communication with the power source and that receives electric current from the power source and that also is in electrical communication with the atomically thin membrane such that an amount of the electric current changes in response to a change in the selected distance between the atomically thin membrane and the solid electrode.

BRIEF DESCRIPTION OF THE DRAWINGS

The following descriptions should not be considered limiting in any way. With reference to the accompanying drawings, like elements are numbered alike.

Figure 29:
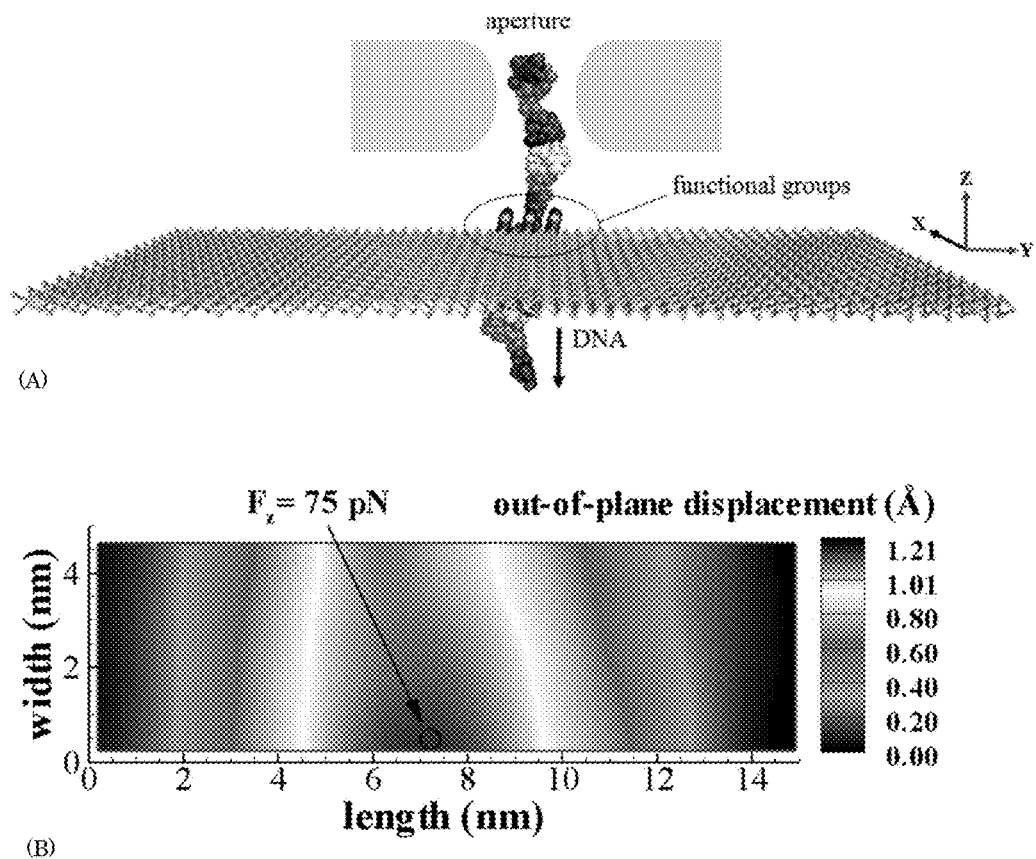
Figure 30:
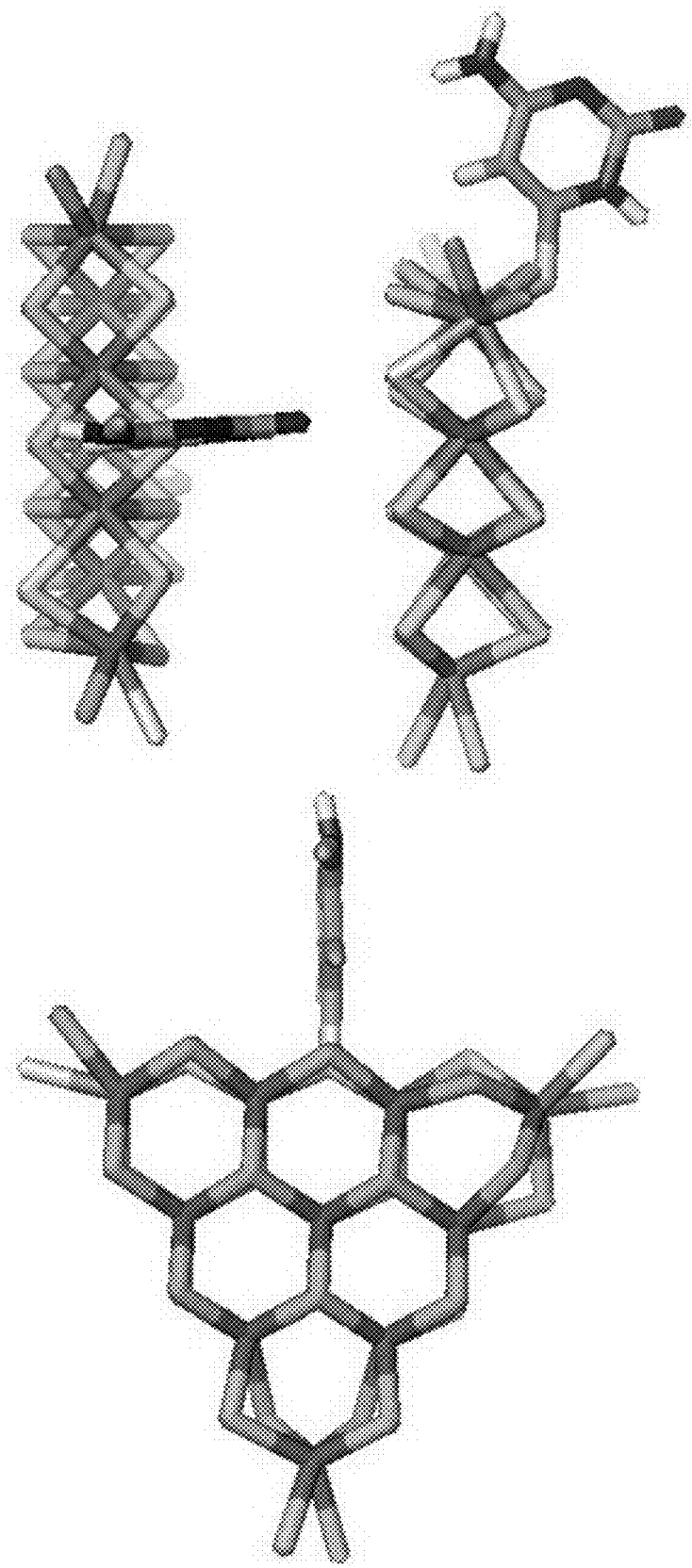
Figure 31:
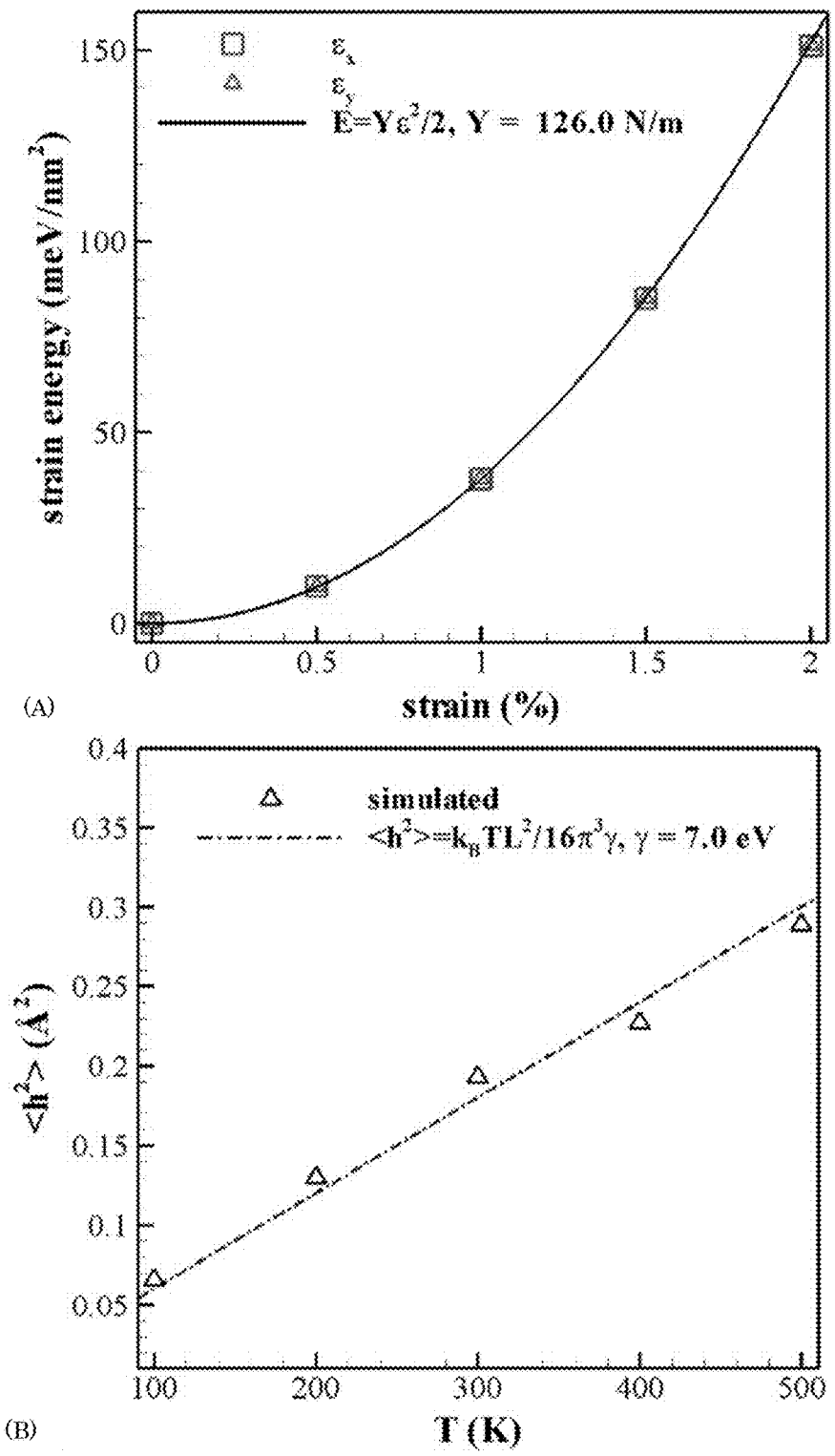
Figure 32:
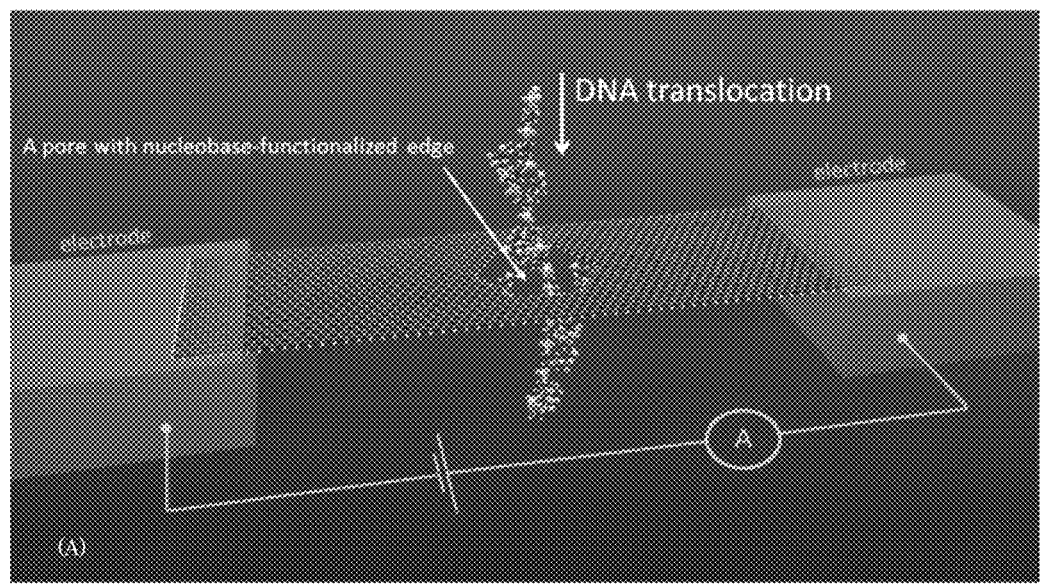
Figure 32:
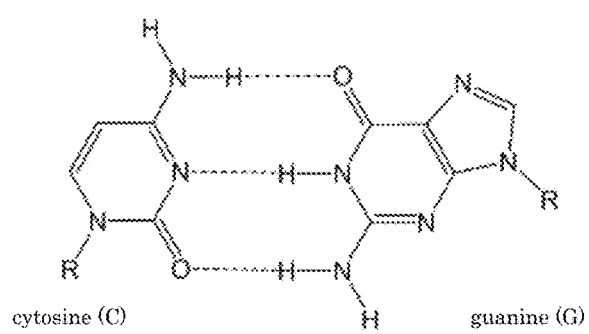
Figure 32:
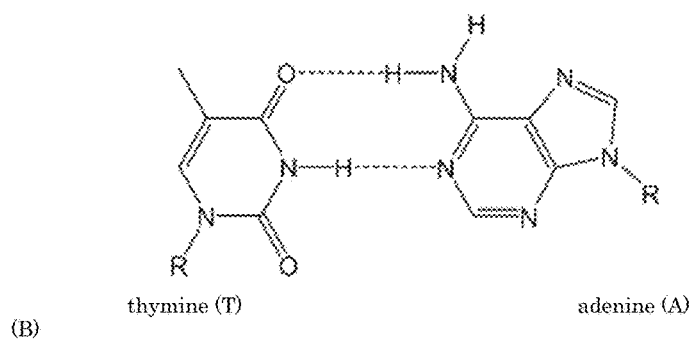
Figure 33:
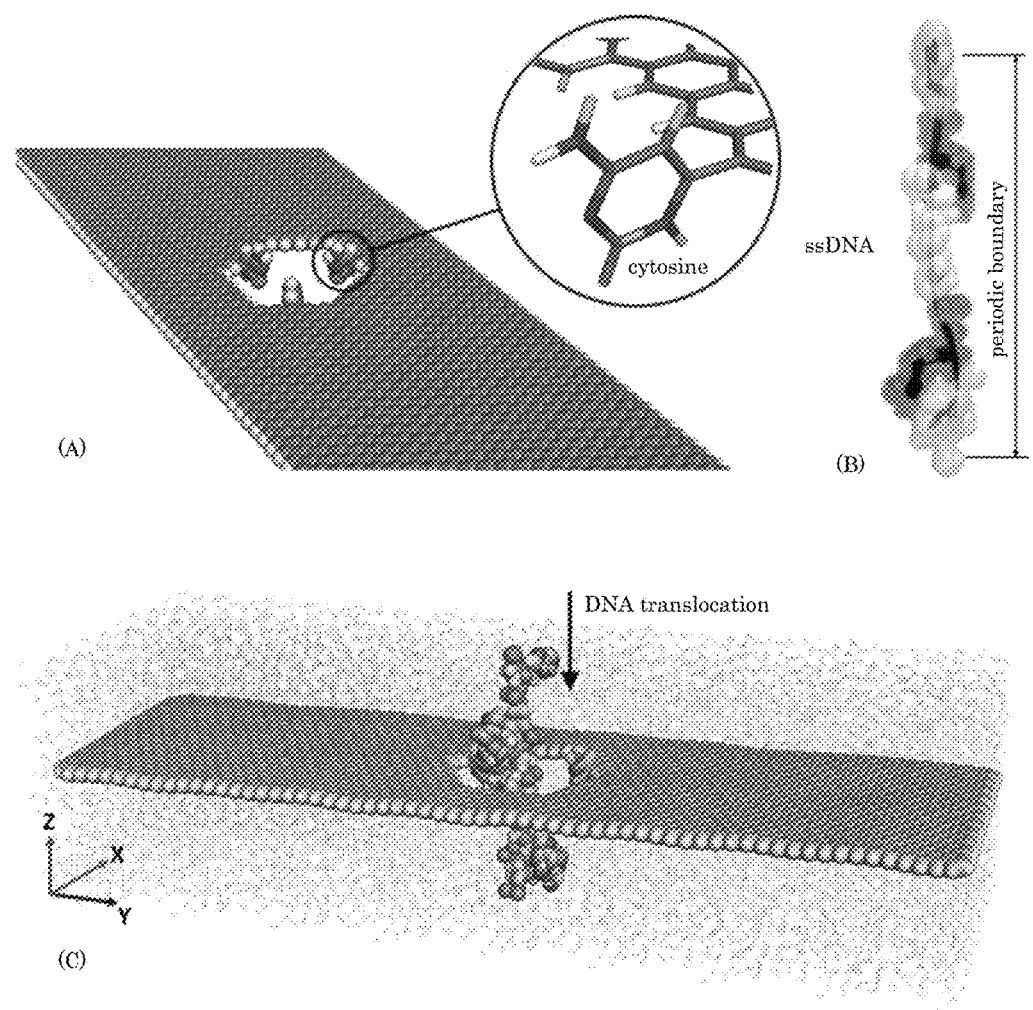
Figure 34:
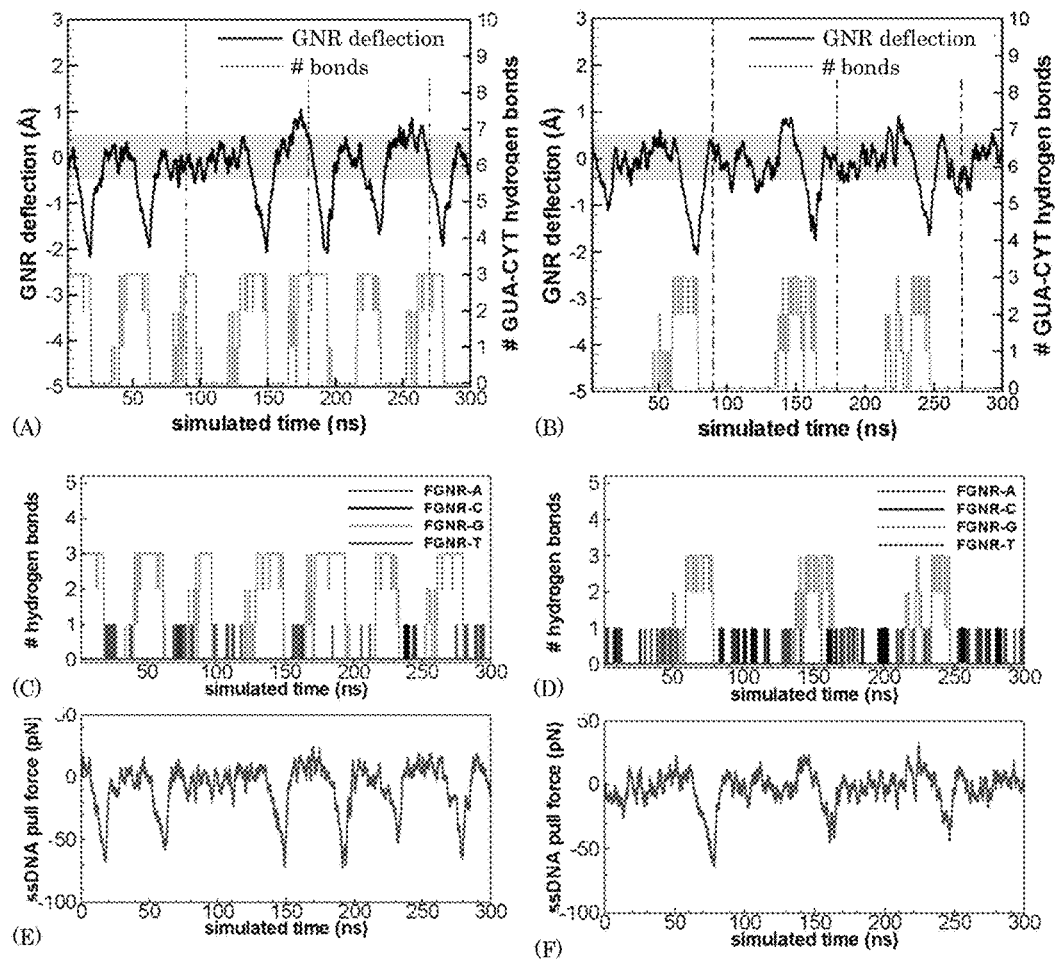
Figure 35:
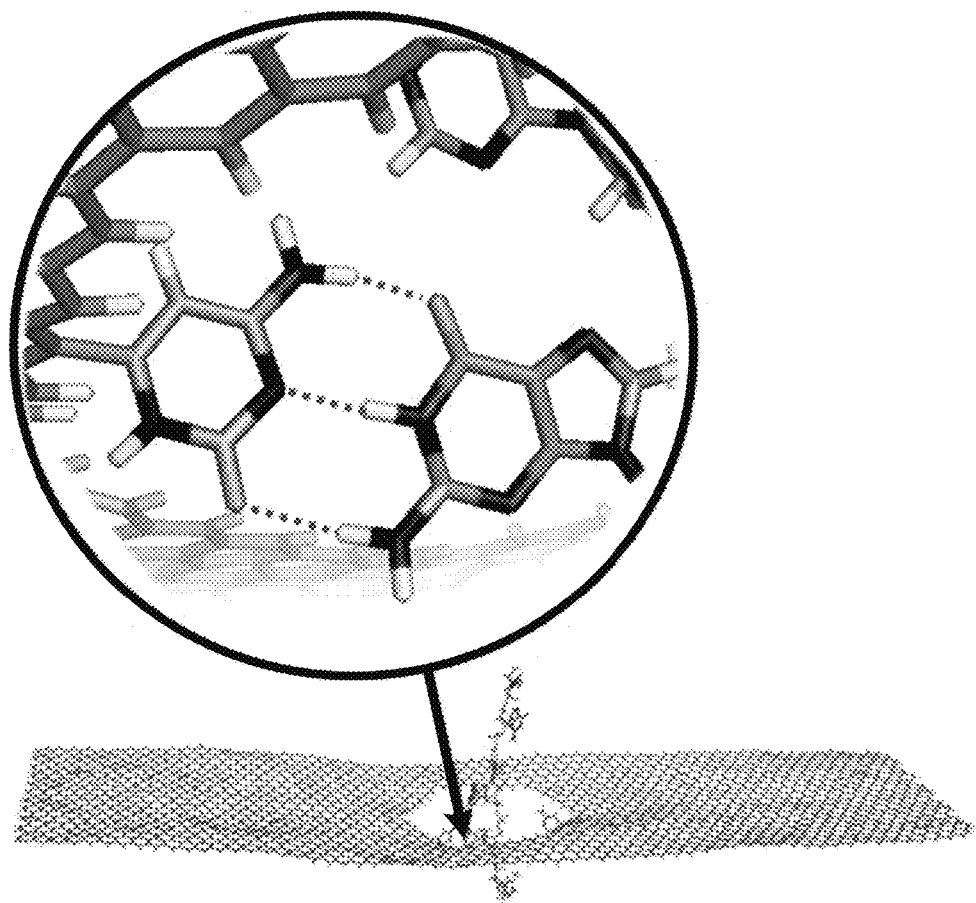
Figure 36:
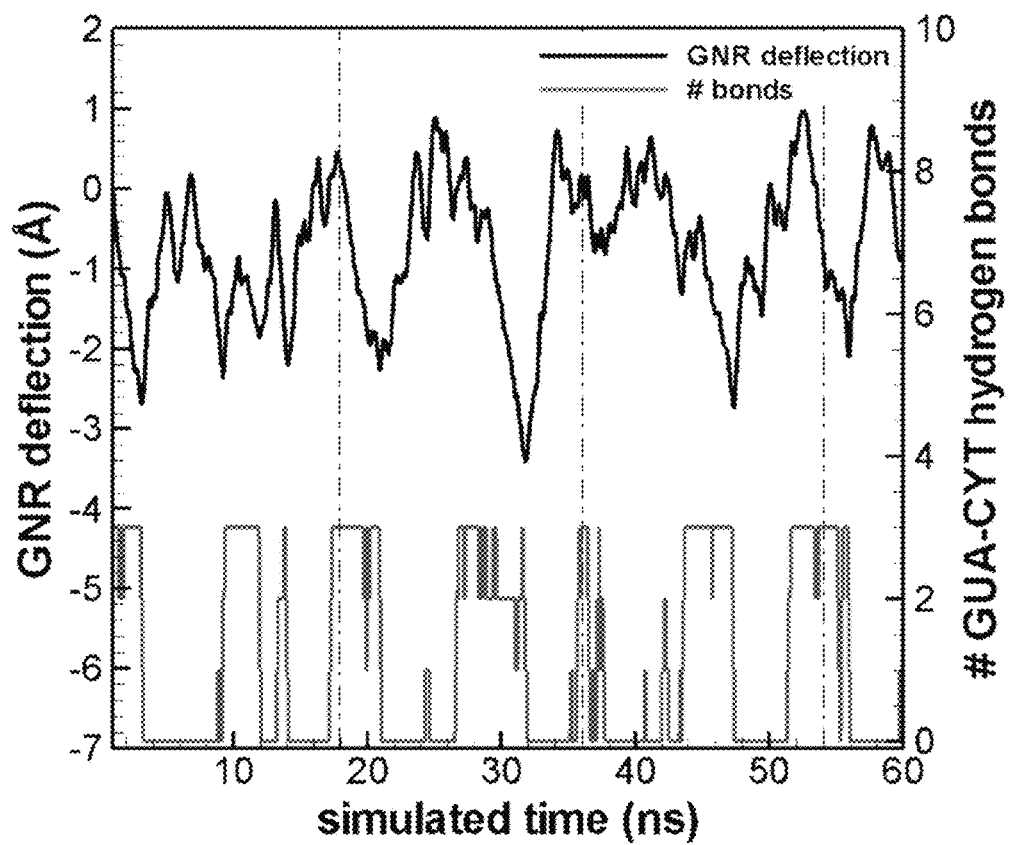
Figure 37:
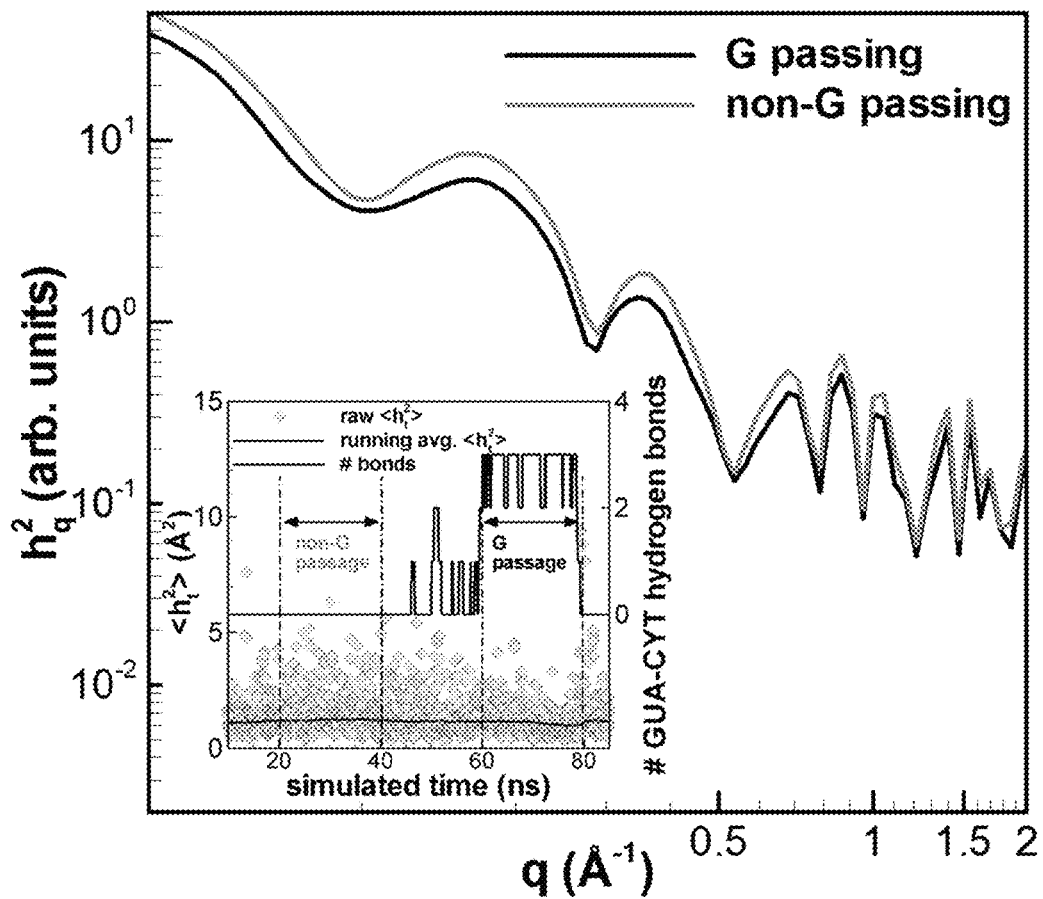

DNA translocation rate was 1 cm/s, and low-pass filter with 200 MHz cutoff was applied to the raw deflection data;

FIG. 29 shows a nucleic acid sequencer in an edge sensor configuration in an absence of an aperture (A) and the distribution of the out-of-plane atomic positions throughout the membrane (B), obtained for a constant $F_z$=75 pN force applied;

FIG. 30 shows an energy-minimized structure for a triangular $MoS_2$ cluster functionalized by a cytosine complementary base;

FIG. 31 shows data and theoretical fits for two-dimensional modulus from uniaxial stretching (A) and bending rigidity from direct simulations of ripples at a set of finite temperatures (B) of the $MoS_2$ model in which a rectangular 14 nm×15 nm $MoS_2$ sample with in-plane periodic boundaries (zigzag and armchair edges along X and Y, respectively) was used;

FIG. 32 shows a perspective view of a nucleic acid sequencer (A) and Watson-Crick base pair (B), wherein dotted lines in panel B are hydrogen bonds;

FIG. 33 shows an atomically thin membrane that includes graphene and a complementary base that includes cytosine disposed on an aperture (A), periodic ssDNA (B), and the atomically thin membrane disposed in water (C);

FIG. 34 shows deflection and several G-C hydrogen bonds as functions of simulation time for ssDNA sequence SEQ1 (periodic GAAGCT) (A) and sequence SEQ2 (periodic TCGAAC) (B); all hydrogen bonds between the FGNR and the ssDNA sequence SEQ1 (C) and SEQ2 (D); ssDNA pulling force during translocation of SEQ1 (E) and SEQ2 (F), wherein ssDNA translocation speed was 5 cm/s;

FIG. 35 shows a deflected state of the FGNR prior to G-C detachment;

FIG. 36 shows FGNR deflection and the number of G-C hydrogen bonds as functions of simulated time during ssDNA (SEQ1) translocation at a rate of 25 cm/s, wherein a low-pass filter with an effective bandwidth of 2.5 GHz was applied to the raw deflection data; and FIG. 37 shows FGNR rippling distributions $h_q^2$ during passage of G and non-G nucleobases, wherein an inset shows averaging regions, raw $\langle h_r^2 \rangle$ data, and $\langle h_r^2 \rangle$ running average data.

DETAILED DESCRIPTION

A detailed description of one or more embodiments is presented herein by way of exemplification and not limitation.

It has been discovered that a nucleic acid sequencer herein provides capacitive displacement to determine a sequence of single stranded nucleic acid, wherein the capacitive displacement and determination are ultra-fast and accurate at a selected temperature, e.g., room temperature. Here, an atomically thin membrane of the nucleic acid sequencer flexes in response to a sub-nanonewton force due to base pairing.

Figure 1:
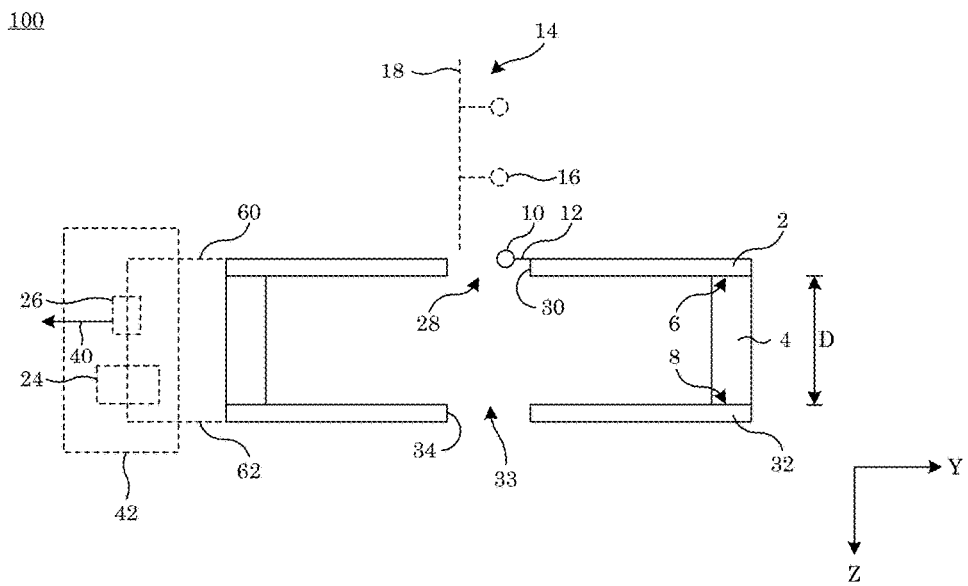
FIG. 1 shows a nucleic acid sequencer in a cross-sectional view along line A-A of the nucleic acid sequencer shown in FIG. 2.
Figure 1:
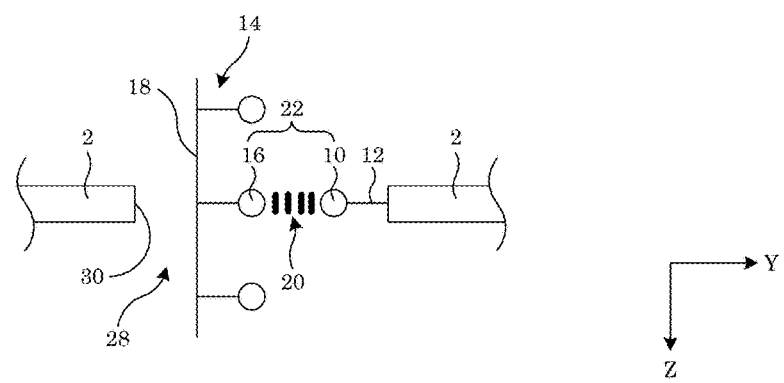
Figure 2:
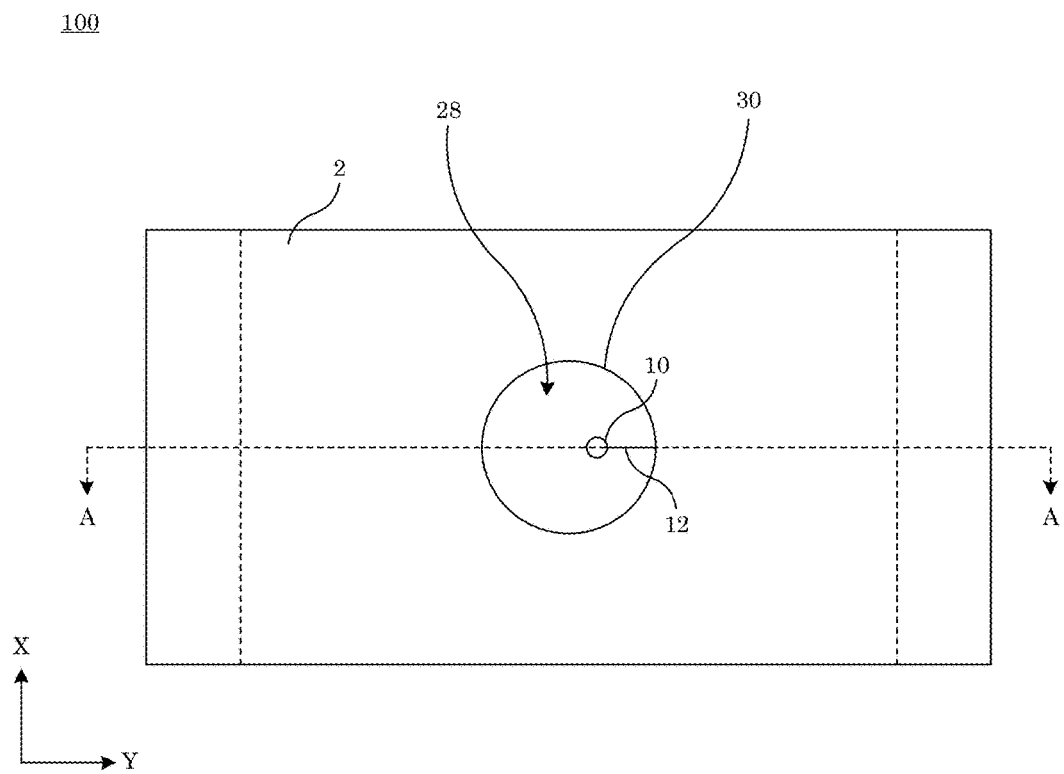
FIG. 2 shows a top view of the nucleic acid sequencer shown in FIG. 1.
Figure 3:
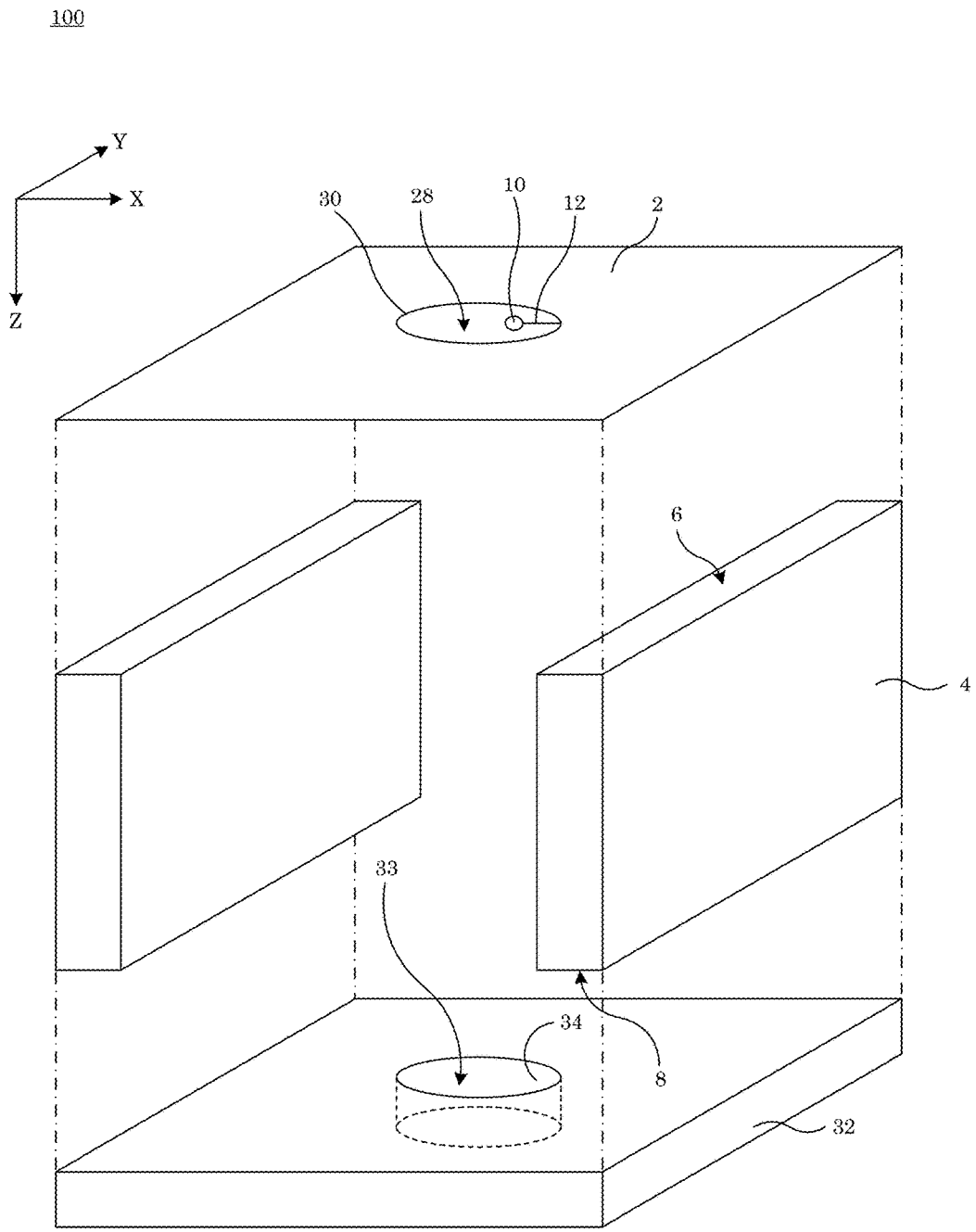
FIG. 3 shows an exploded view of the nucleic acid sequencer shown in FIG. 1.
Figure 23:
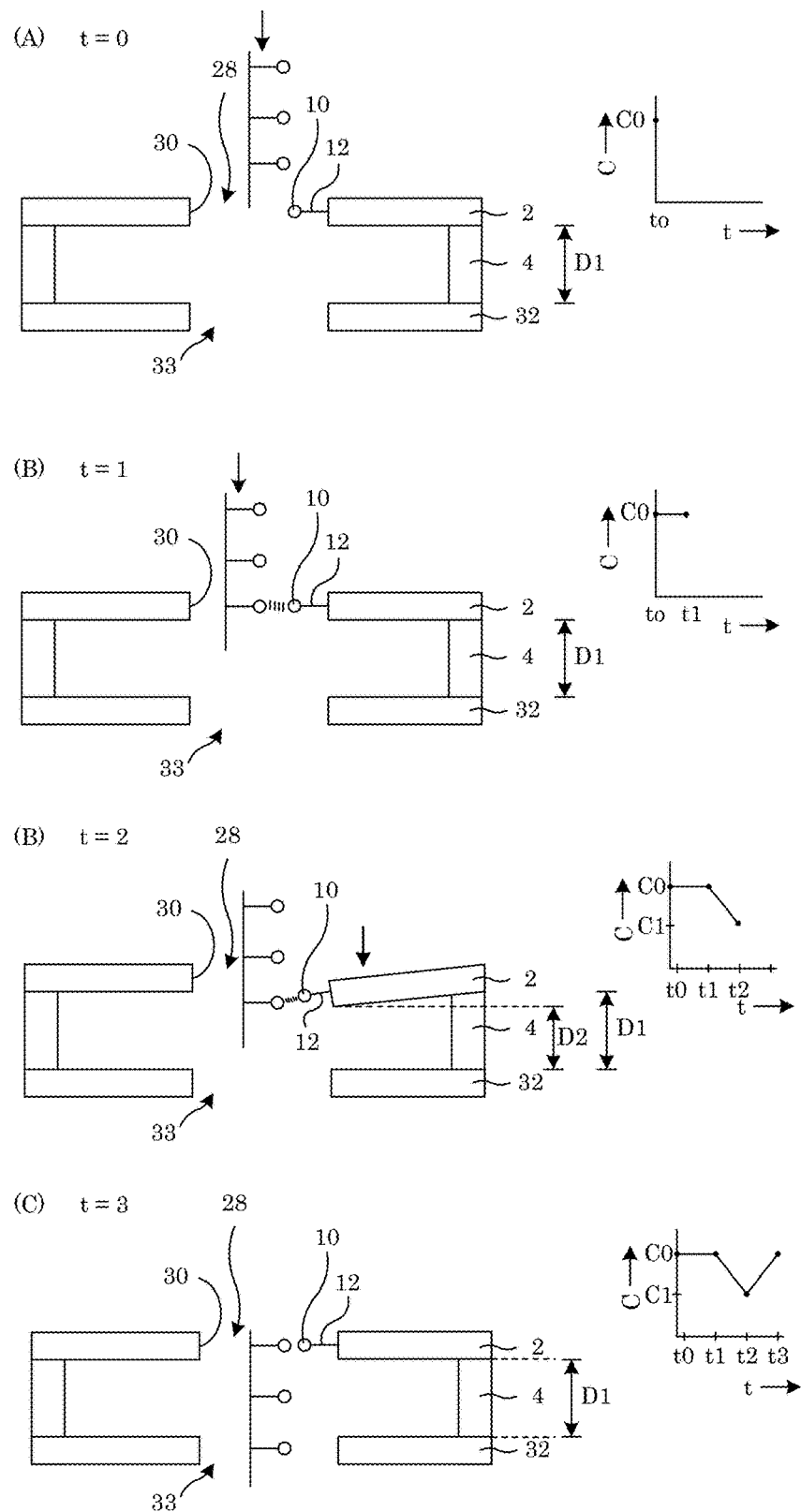
FIG. 23 shows a cross-section of a nucleic acid sequencer in presence of a single stranded nucleic acid.

In an embodiment, with reference to FIG. 1 (a cross-sectional view), FIG. 2 (top view), and FIG. 3 (exploded view), nucleic acid sequencer 100 electrically determines a sequence of nitrogenous bases in a single stranded nucleic acid and includes atomically thin membrane 2; solid electrode 32 spaced apart from atomically thin membrane 2 and arranged in a capacitive configuration with atomically thin membrane 2; spacer member 4 interposed between atomically thin membrane 2 and solid electrode 32 and including: first surface 6 on which atomically thin membrane 2 is disposed; and second surface 8 on which solid electrode 32 is disposed, such that spacer member 4 provides selected distance D between atomically thin membrane 2 and solid electrode 32; complementary base 10 covalently disposed on atomically thin membrane 2 and arranged to form base pair 22 (e.g., via hydrogen bond 20) with nitrogenous base 16 of single stranded nucleic acid 14; detector 42 that includes power source 24 in electrical communication via electrical conductor 62 (e.g., a wire, wire trace, and the like) with solid electrode 32 and that provides electrical power to solid electrode 32; and resistor 26 in electrical communication via electrical conductor 60 (e.g., a wire, wire trace, and the like) with power source 24 and that receives electric current from power source 24 and that also is in electrical communication with atomically thin membrane 2 such that an amount of the electric current changes in response to a change in selected distance between the atomically thin membrane 2 and solid electrode 32. Detector 42 produces sequencer signal 40 based on selected distanced D such that sequencer signal 40 has a value that changes as selected distance D changes. Moreover, atomically thin membrane 2 can include aperture 28 through which to communicate single stranded nucleic acid, wherein aperture 20 is bounded by wall 38 of atomically thin membrane 2. Additionally, solid electrode 32 can include aperture 33 bounded by wall 34. It is contemplated that single stranded nucleic acid 14 can include nitrogenous base 16 bonded to the backbone 18. Panel B of FIG. 1 shows hydrogen bond 20 formed between complementary base 10 (disposed on atomically thin membrane 2 via linker 12) and nitrogenous base 16 to form base pair 28 that includes nitrogenous bases 16 and complementary base 10. In this manner, single stranded nucleic acid for team is communicated through aperture 28 and moves toward solid electrode 32. As single stranded nucleic acid 14 communicated through aperture 28, nitrogenous base 16 can form base pair 22 with complementary base 10 disposed on atomically thin membrane 2 when complementary base 10 is a complement to nitrogenous base 16. As single stranded nucleic acid 14 further propagates toward solid electrode 32, atomically thin membrane 2 can flex toward solid electrode 32 decreasing selected distance D. As a result, a capacitance changes in the capacitive configuration that includes atomically thin membrane 2 and solid electrode 32. This electrical behavior is described below with reference to FIG. 23.

As used herein, "capacitive configuration" refers to a geometric combination of the atomically thin membrane and the solid electrode in which the atomically thin membrane and the solid electrode are opposingly stacked, spaced apart, and store electrical energy to produce an electric field between the atomically thin membrane and the solid electrode.

Figure 4:
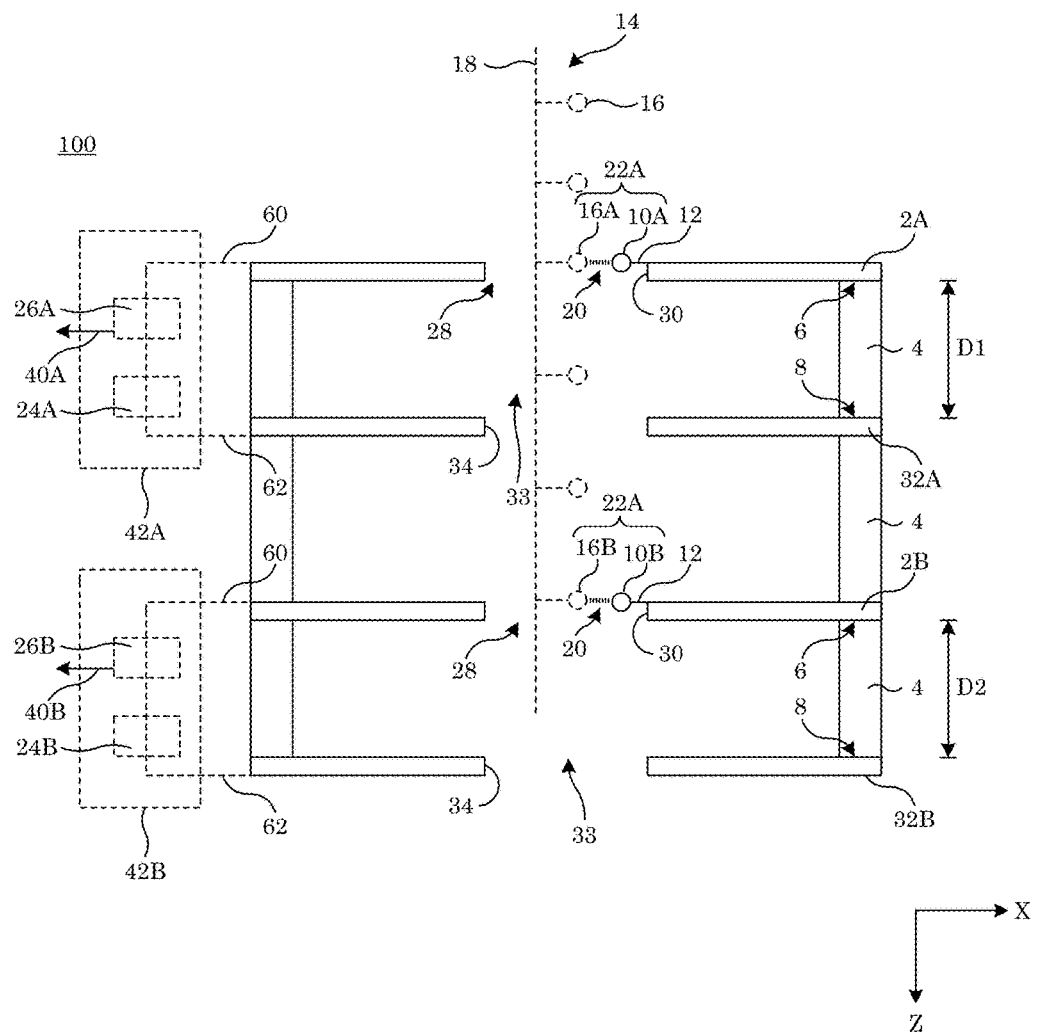
FIG. 4 shows a cross-section of a nucleic acid sequencer.

In an embodiment, with reference to FIG. 4, nucleic acid sequencer 100 includes first atomically thin membrane 2A; first complementary base 10A covalently disposed on first atomically thin membrane 2A and spaced apart from first solid electrode 32A; second atomically thin membrane 2B; second complementary base 10B covalently disposed on second atomically thin membrane 2B; and second solid electrode 32B spaced apart from the second atomically thin membrane 2B, wherein first atomically thin membrane 2A and second atomically thin membrane 2B are spaced apart, and first complementary base 10A is different than second complementary base 10B. Here, first complementary base 10A forms first base pair 22A with first nitrogenous base 16A, and second complementary base 10B forms second base pair 22B with second nitrogenous base 16B. Due to formation of first base pair 22A or second base pair 22B and flexure of first atomically thin membrane 2A or second atomically thin membrane 2B, first detector 42A produces first sequencer signal 40A based on first selected distanced D1, or second detector 42B produces second sequencer signal 40B based on second selected distanced D2. It should be appreciated that first nitrogenous base 16A is different than second nitrogenous base 16B because first complementary base 10A is different than the second complementary base 10B. In this manner, nucleic acid sequencer 100 produces unique sequencer signals (40A, 40B) due to an identity of complementary base (e.g., 10A, 10B) in a presence of the sequence of nitrogenous bases in single stranded nucleic acid 14.

Figure 5:
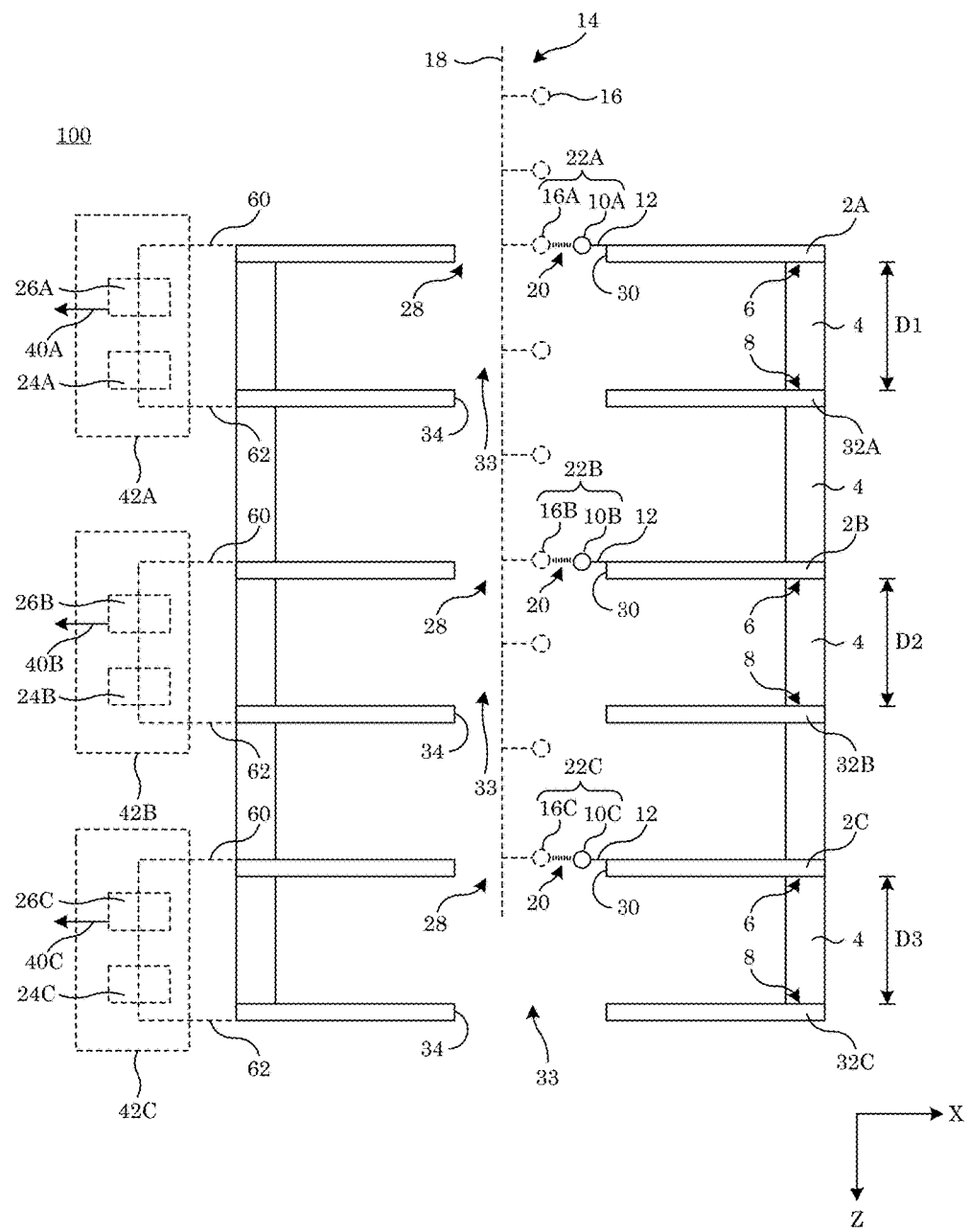
FIG. 5 shows a cross-section of a nucleic acid sequencer.

In an embodiment, with reference to FIG. 5, nucleic acid sequencer 100 includes first atomically thin membrane 2A; first complementary base 10A covalently disposed on first atomically thin membrane 2A and spaced apart from first solid electrode 32A; second atomically thin membrane 2B; second complementary base 10B covalently disposed on second atomically thin membrane 2B; and second solid electrode 32B spaced apart from the second atomically thin membrane 2B, wherein first atomically thin membrane 2A and second atomically thin membrane 2B are spaced apart, and first complementary base 10A is different than second complementary base 10B. Additionally, nucleic acid sequencer 100 includes third atomically thin membrane 2C and third complementary base 10C covalently disposed on third atomically thin membrane 2C, wherein first atomically thin membrane 2A, second atomically thin membrane 2B, and third atomically thin membrane 2C are spaced apart, and first complementary base 10A and second complementary base 10B are different than third complementary base 10C. Here, first complementary base 10A forms first base pair 22A with first nitrogenous base 16A. Second complementary base 10B forms second base pair 22B with second nitrogenous base 16B, and third complementary base 10C forms third base pair 22C with third nitrogenous base 16C. Due to formation of first base pair 22A, second base pair 22B, or third base pair 22C and flexure of first atomically thin membrane 2A, second atomically thin membrane 2B, or third atomically thin membrane 2C, first detector 42A produces first sequencer signal 40A based on first selected distanced D1, second detector 42B produces second sequencer signal 40B based on second selected distanced D2, or third detector 42C produces third sequencer signal 40C based on third selected distanced D3. It should be appreciated that first nitrogenous base 16A, second nitrogenous base 16B, and third nitrogenous base 16C are unique because first complementary base 10A, second complementary base 10B, and third complementary base 10C are unique. In this manner, nucleic acid sequencer 100 produces unique sequencer signals (40A, 40B, 40C) due to an identity of complementary base (e.g., 10A, 10B, 10C) in a presence of the sequence of nitrogenous bases in single stranded nucleic acid 14.

Figure 6:
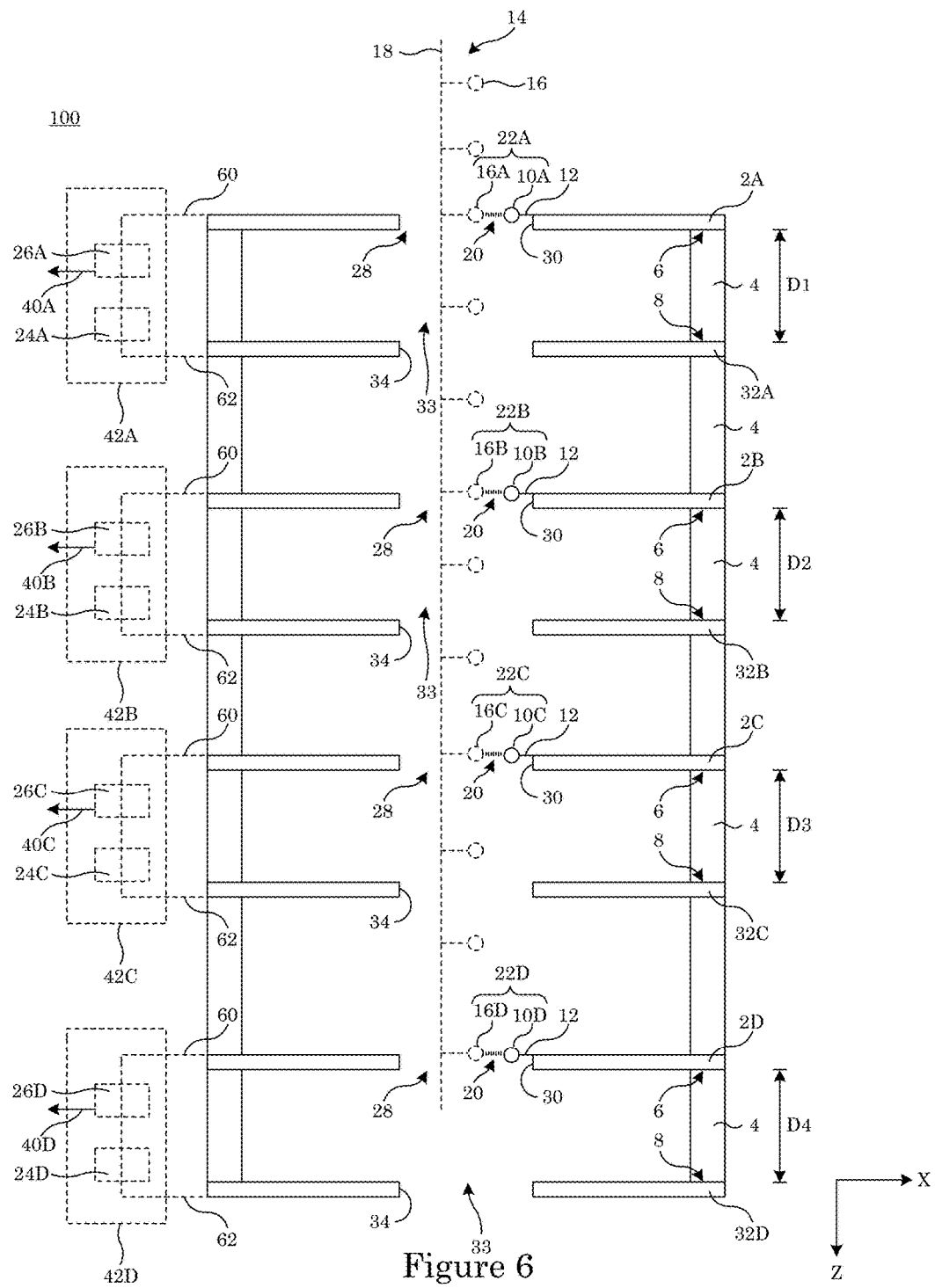
FIG. 6 shows a cross-section of a nucleic acid sequencer.
Figure 7:
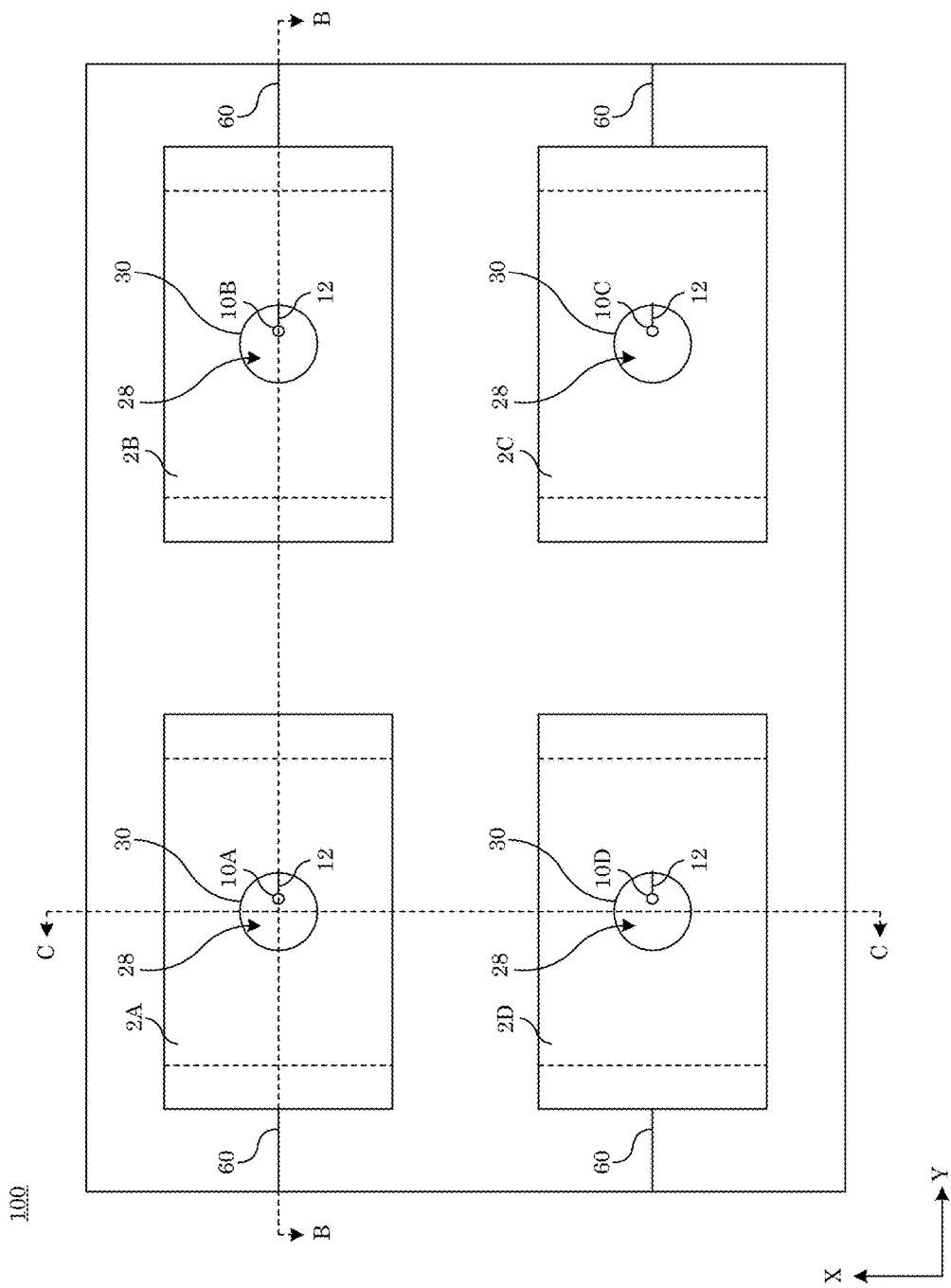
FIG. 7 shows a top view of a nucleic acid sequencer.
Figure 8:
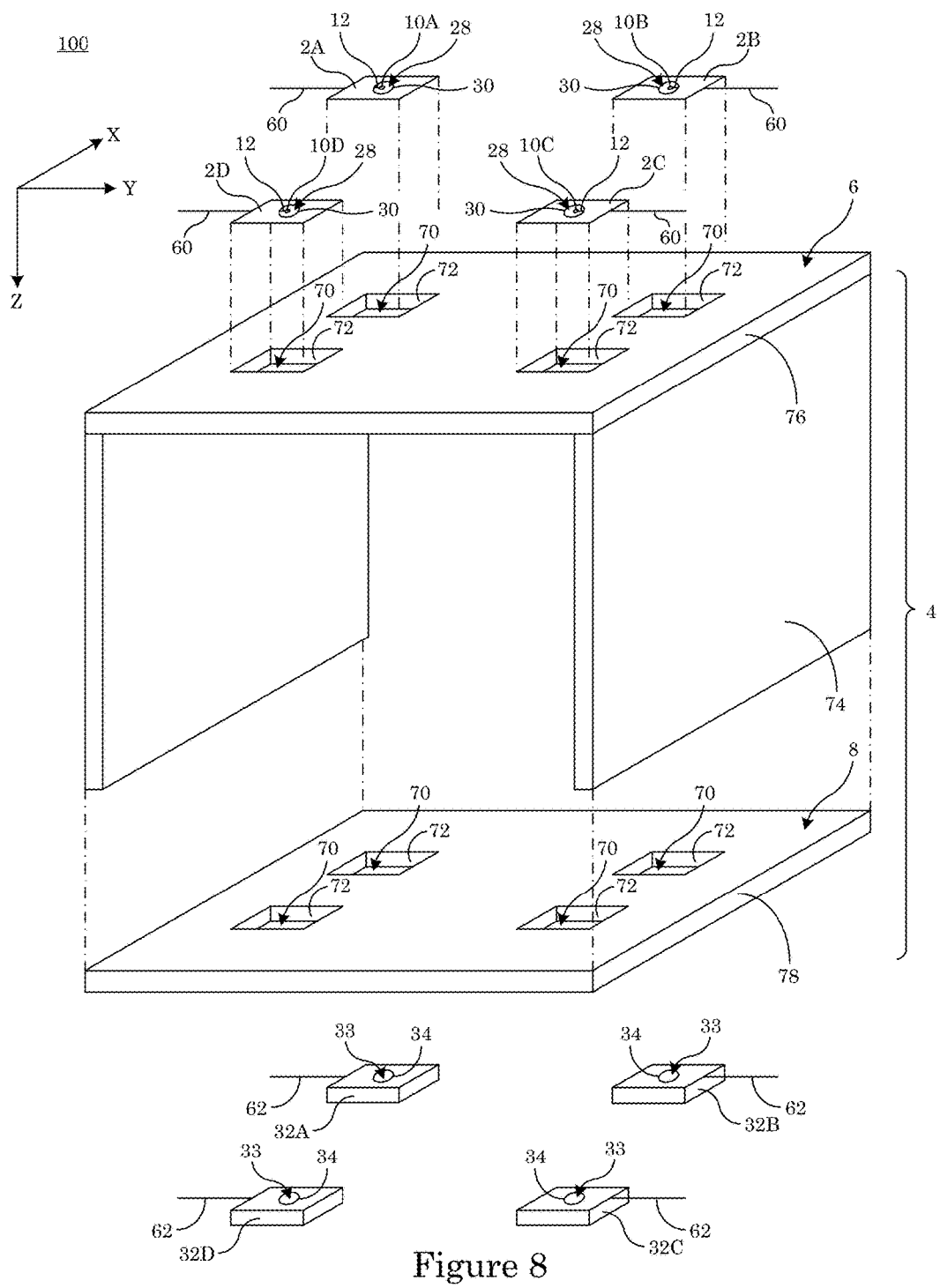
FIG. 8 shows an exploded view of the nucleic acid sequencer shown in FIG. 7.
Figure 9:
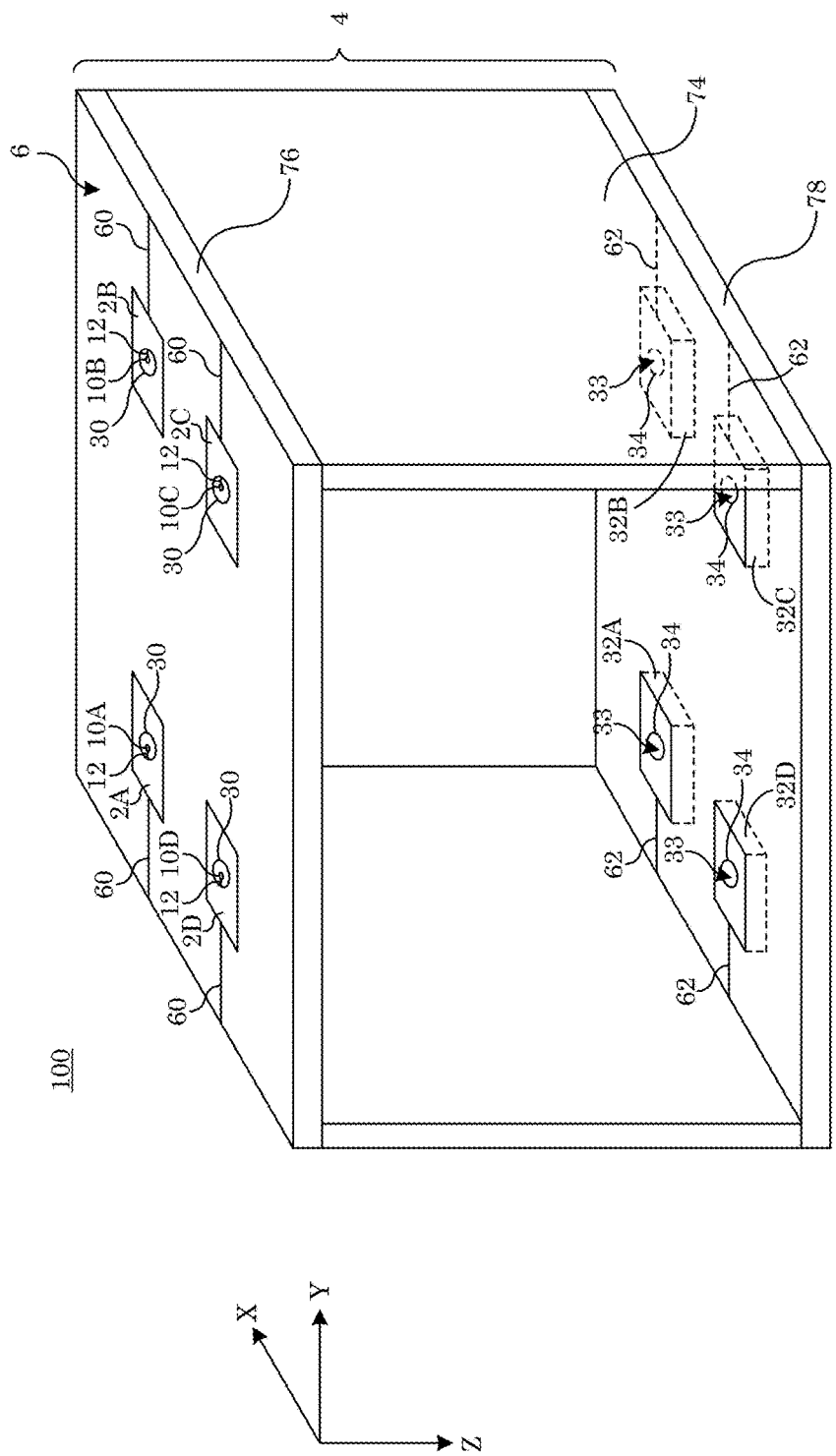
FIG. 9 shows a perspective view of the nucleic acid sequencer shown in FIG. 7.

In an embodiment, with reference to FIG. 6, nucleic acid sequencer 100 includes first atomically thin membrane 2A; first complementary base 10A covalently disposed on first atomically thin membrane 2A and spaced apart from first solid electrode 32A; second atomically thin membrane 2B; second complementary base 10B covalently disposed on second atomically thin membrane 2B; and second solid electrode 32B spaced apart from the second atomically thin membrane 2B, wherein first atomically thin membrane 2A and second atomically thin membrane 2B are spaced apart, and first complementary base 10A is different than second complementary base 10B. Additionally, nucleic acid sequencer 100 includes third atomically thin membrane 2C; third complementary base 10C covalently disposed on third atomically thin membrane 2C; fourth atomically thin membrane 2D; and fourth complementary base 10D covalently disposed on fourth atomically thin membrane 2D, wherein first atomically thin membrane 2A, second atomically thin membrane 2B, third atomically thin membrane 2C, and fourth atomically thin membrane 2D are spaced apart. Here, first complementary base 10A forms first base pair 22A with first nitrogenous base 16A, and second complementary base 10B forms second base pair 22B with second nitrogenous base 16B. Third complementary base 10C forms third base pair 22C with third nitrogenous base 16C, and fourth complementary base 10D forms fourth base pair 22D with fourth nitrogenous base 16D. Due to formation of first base pair 22A, second base pair 22B, third base pair 22C, or fourth base pair 22D and flexure of first atomically thin membrane 2A, second atomically thin membrane 2B, third atomically thin membrane 2C, or fourth atomically thin membrane 2D, first detector 42A produces first sequencer signal 40A based on first selected distanced DI; second detector 42B produces second sequencer signal 40B based on second selected distanced D2; third detector 42C produces third sequencer signal 40C based on third selected distanced D3, or fourth detector 42D produces fourth sequencer signal 40D based on fourth selected distanced D4. It should be appreciated that first nitrogenous base 16A, second nitrogenous base 16B, third nitrogenous base 16C, and forth nitrogenous base 16D are unique because first complementary base 10A, second complementary base 10B, third complementary base 10C, and forth complementary base 10D are unique. In this manner, nucleic acid sequencer 100 produces unique sequencer signals (40A, 40B, 40C, 40D) due to an identity of complementary base (e.g., 10A, 10B, 10C, 10D) in a presence of the sequence of nitrogenous bases in single stranded nucleic acid 14.

In an embodiment, nucleic acid sequencer 100 includes a plurality of atomically thin membranes 10 stackedly arranged to serially receive and to serially communicate single stranded nucleic acid 14 among the plurality of atomically thin membranes (e.g., 2A, 2B, 2C, 2D, and the like) as shown, e.g., in FIG. 4, FIG. 5, and FIG. 6.

Figure 10:
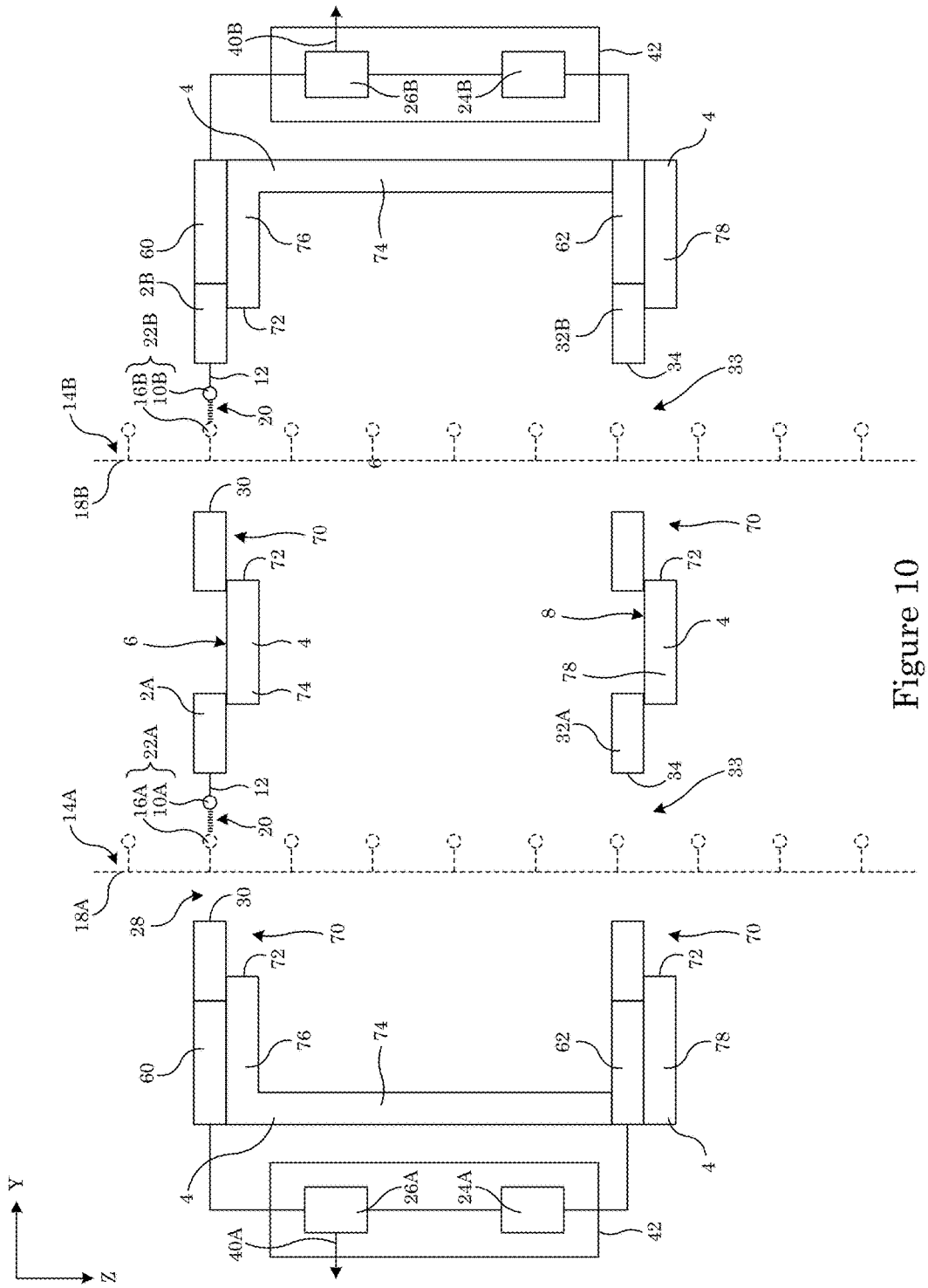
FIG. 10 shows a cross-section along line B-B of the nucleic acid sequencer shown in FIG. 7.
Figure 11:
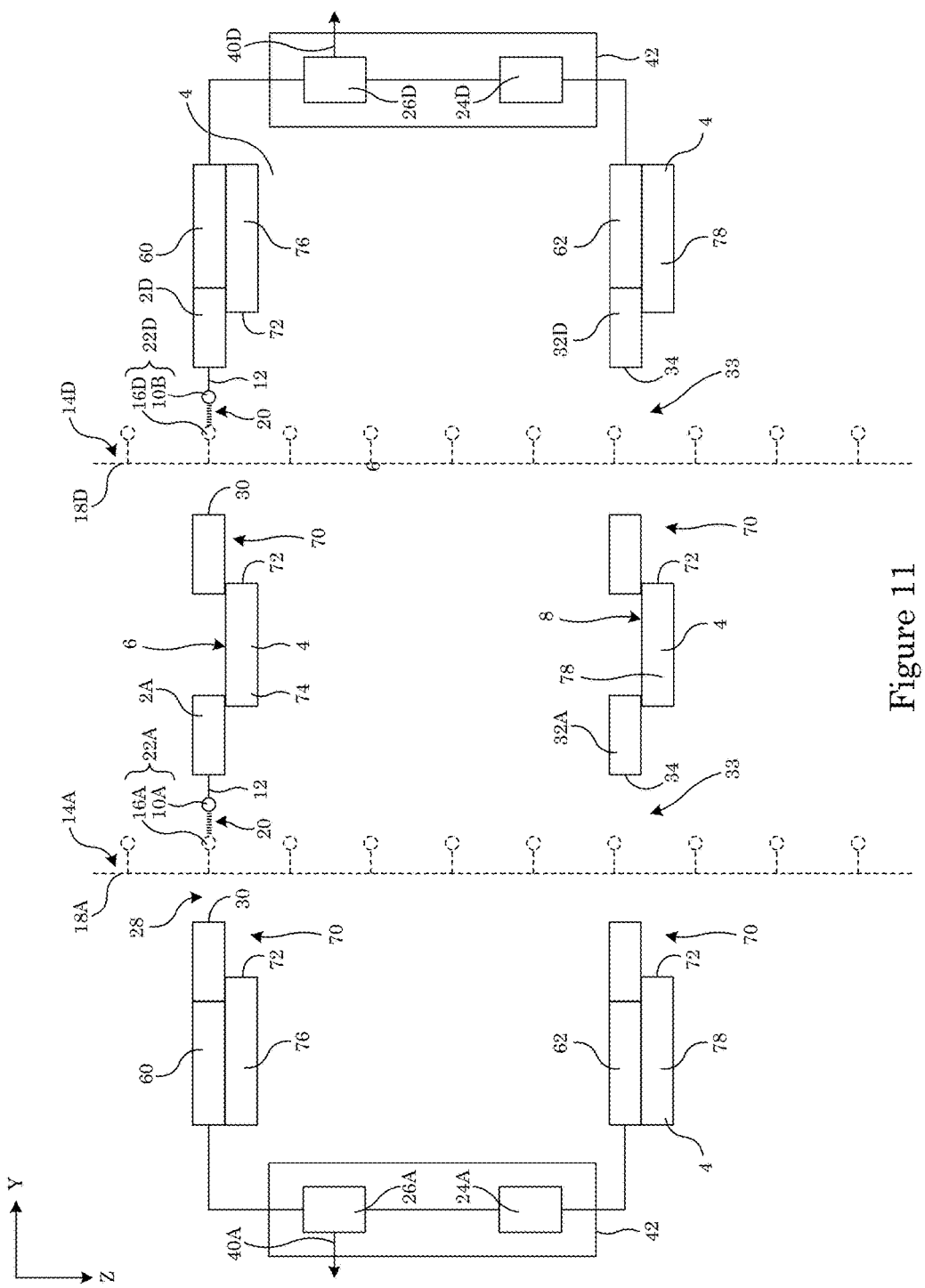
FIG. 11 shows a cross-section along line B-B of the nucleic acid sequencer shown in FIG. 7.
Figure 12:
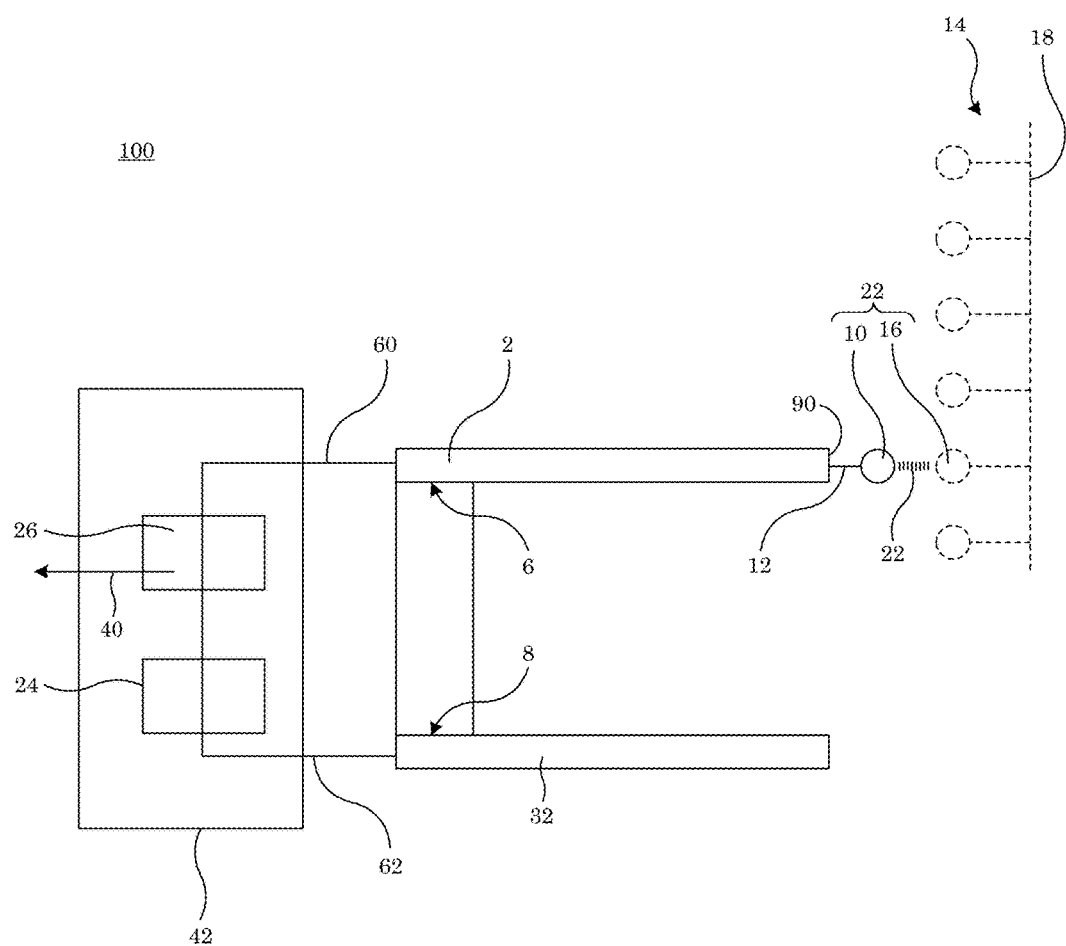
FIG. 12 shows a nucleic acid sequencer in a cross-sectional view along line A-A of the nucleic acid sequencer shown in FIG. 13.
Figure 13:
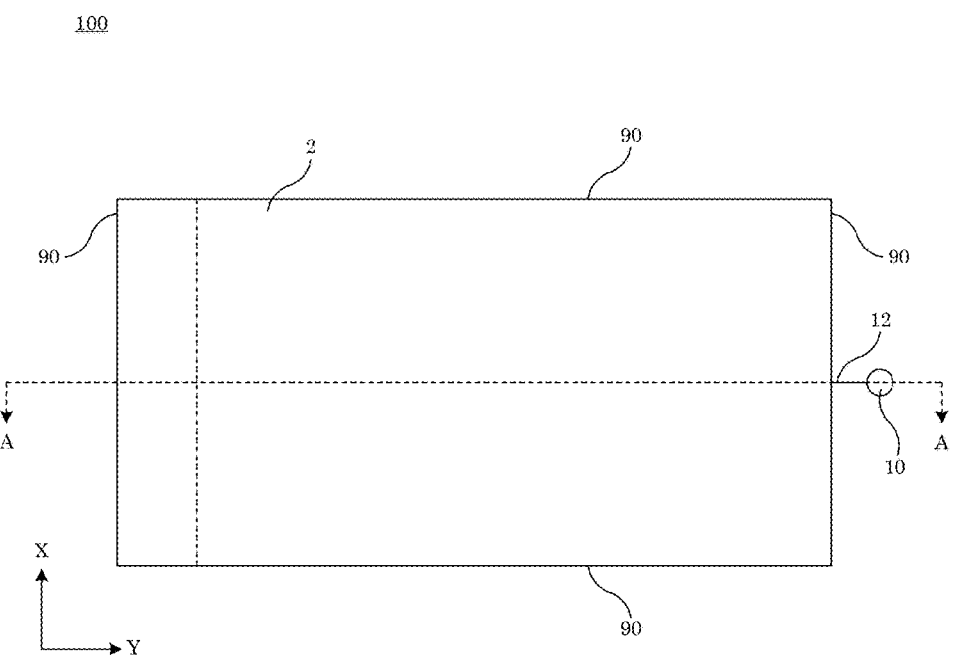
FIG. 13 shows a top view of the nucleic acid sequencer shown in FIG. 12.
Figure 14:
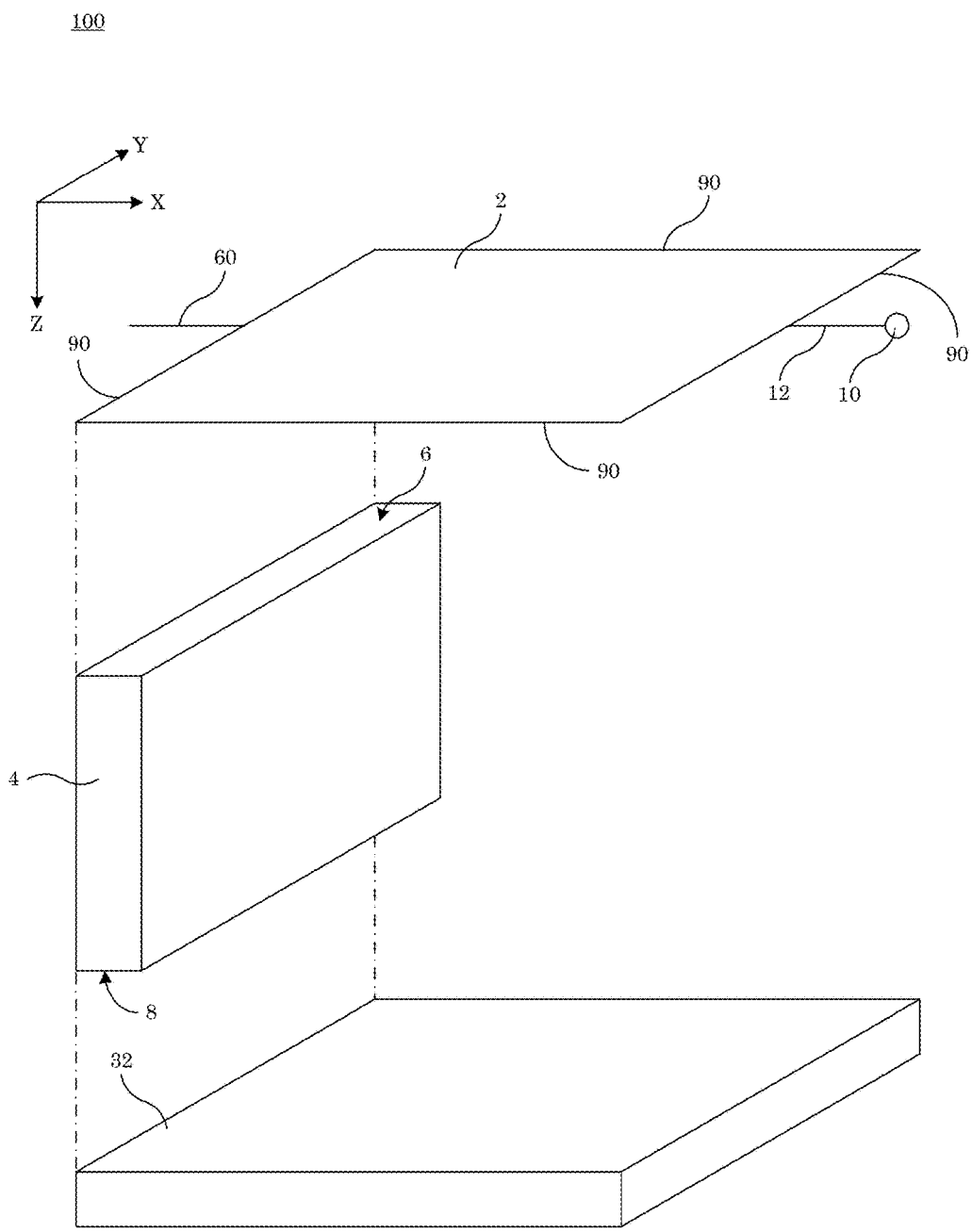
FIG. 14 shows an exploded view of the nucleic acid sequencer shown in FIG. 12.
Figure 15:
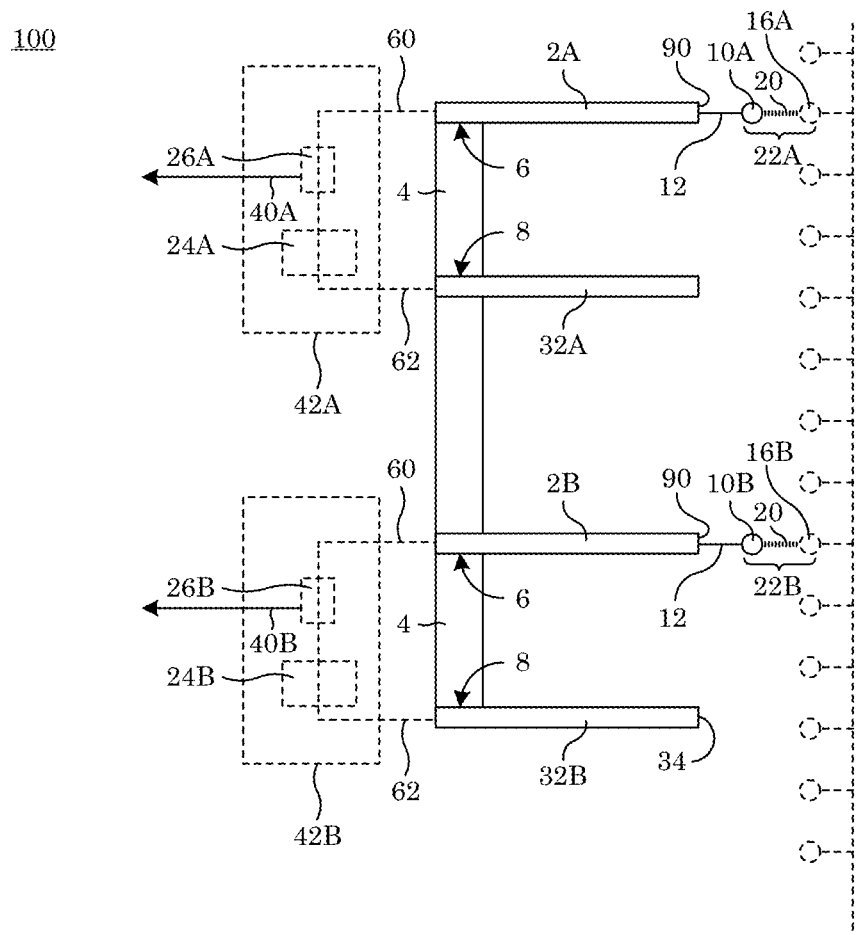
FIG. 15 shows a cross-section of a nucleic acid sequencer.
Figure 16:
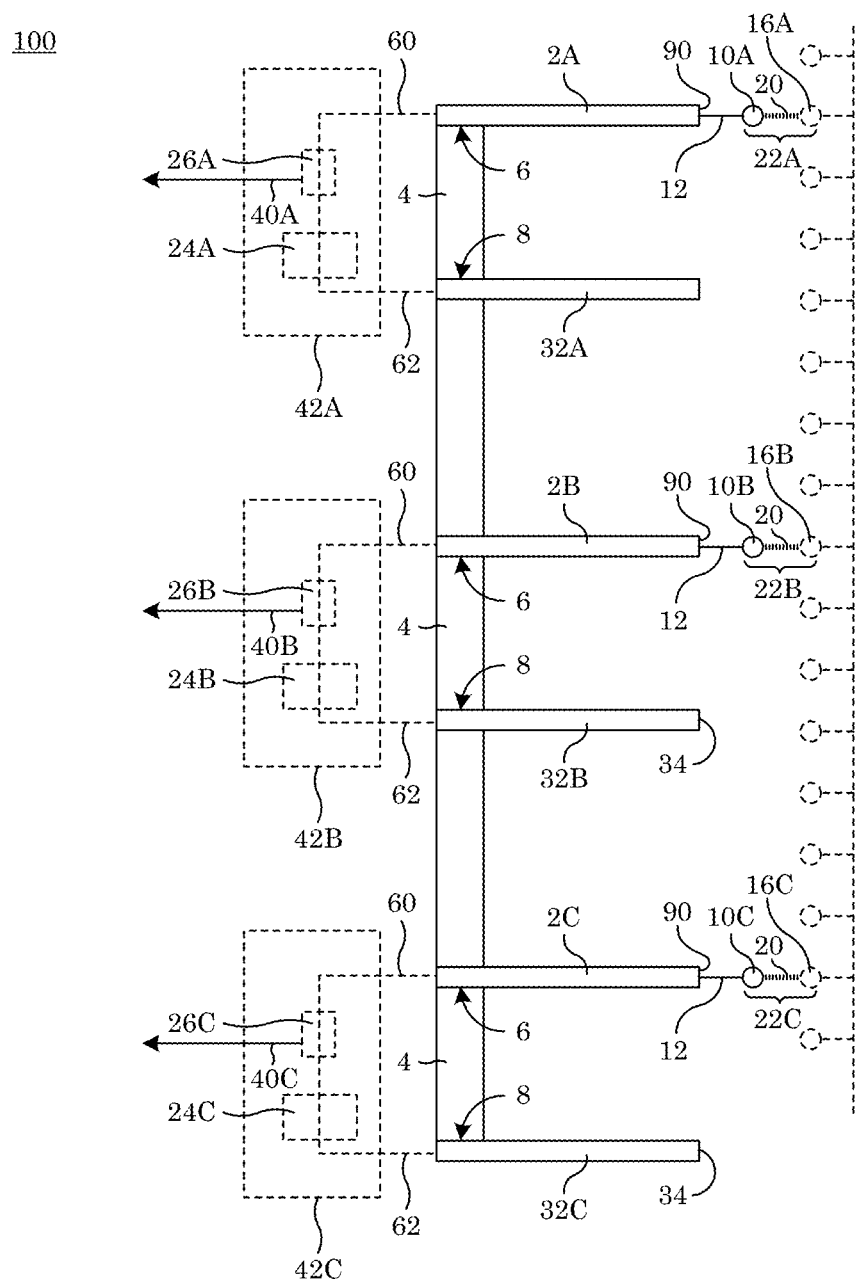
FIG. 16 shows a cross-section of a nucleic acid sequencer.
Figure 17:
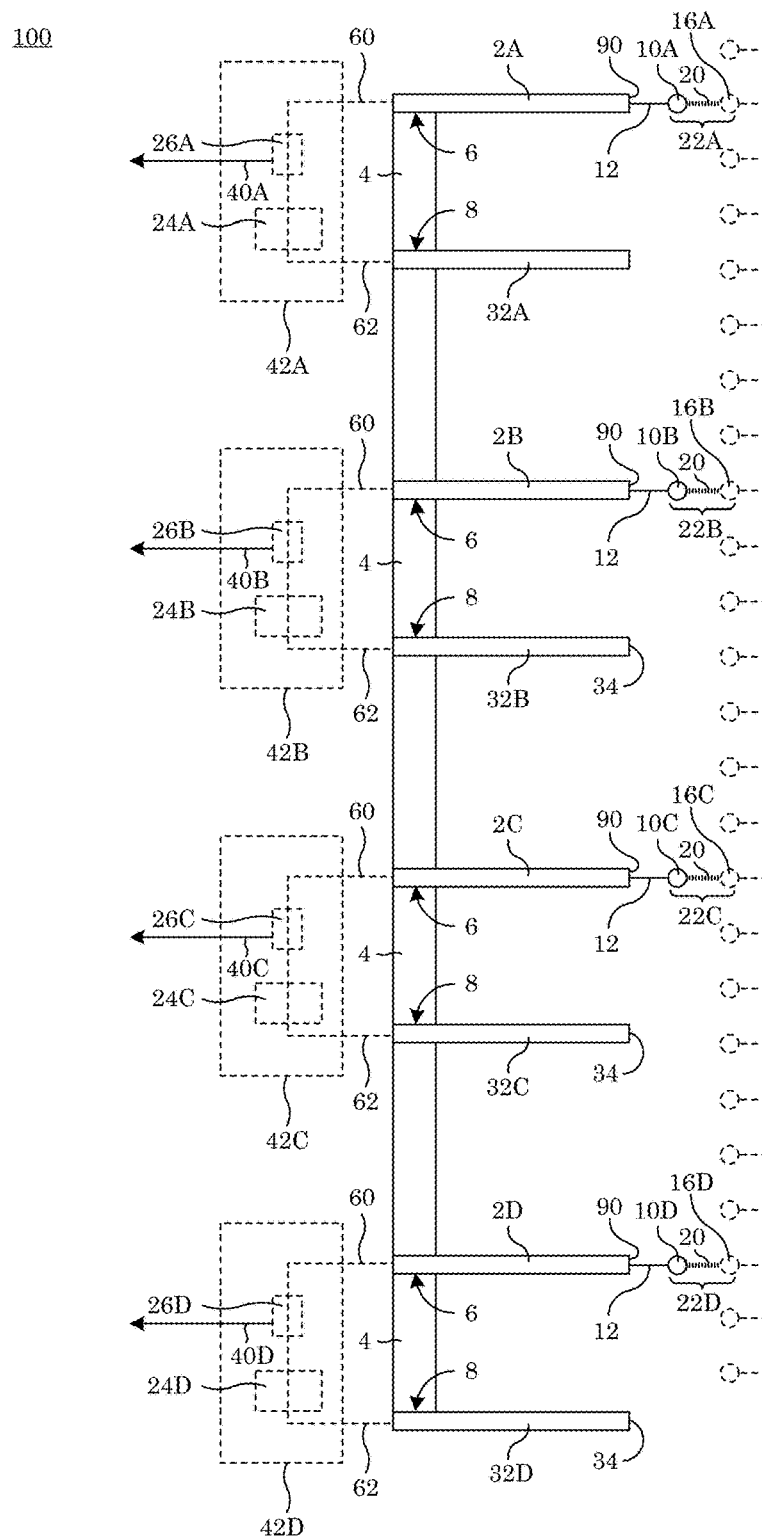
FIG. 17 shows a cross-section of a nucleic acid sequencer.

According to an embodiment, as shown in FIG. 7, FIG. 8, FIG. 9, FIG. 10, and FIG. 11, nucleic acid sequencer 100 includes a plurality of atomically thin membranes 2 (e.g., 2A, 2 B, 2 C, 2D, and the like) that include complementary base 10 (e.g., 10A, 10B, 10C, 10D, and the like) disposed thereon and laterally arranged to receive and communicate in parallel (e.g., synchronously or asynchronously) a plurality of single stranded nucleic acids 14 (e.g., 14A, 14B, 14C, 14D, and the like). Here, spacer member 4 includes sidewall 74; first wall 76 having first surface 6 in which apertures 70 bounded by walls 72 are disposed and on which atomically thin membranes (10A, 10B, 10C, 10D, and the like) are disposed; and second wall 78 having second surface 8 in which apertures 70 bounded by walls two are disposed in on which solid electrodes (32A, 32B, 32C, 32D, and the like) are disposed. In this manner, as shown in FIG. 10 and FIG. 11, first single stranded nucleic acid 14A communicates through aperture 28 of first atomically thin membrane 2A; second single stranded nucleic acid 14B communicates through aperture 28 of second atomically thin membrane 2B; third single stranded nucleic acid 14C communicates through aperture 28 of third atomically thin membrane 2C, and forth single stranded nucleic acid 14D communicates through aperture 28 of fourth atomically thin membrane 2D. Although, in FIG. 7, FIG. 8, FIG. 9, FIG. 10, and FIG. 11, atomically thin membranes 2 (e.g., 2A, 2 B, 2 C, 2D) are disposed in a two-dimensional arrangement, in an embodiment, atomically thin membranes 2 (e.g., 2A, 2 B, 2 C, 2D) are disposed in a linear arrangement, e.g., see FIG. 18.

Figure 18:
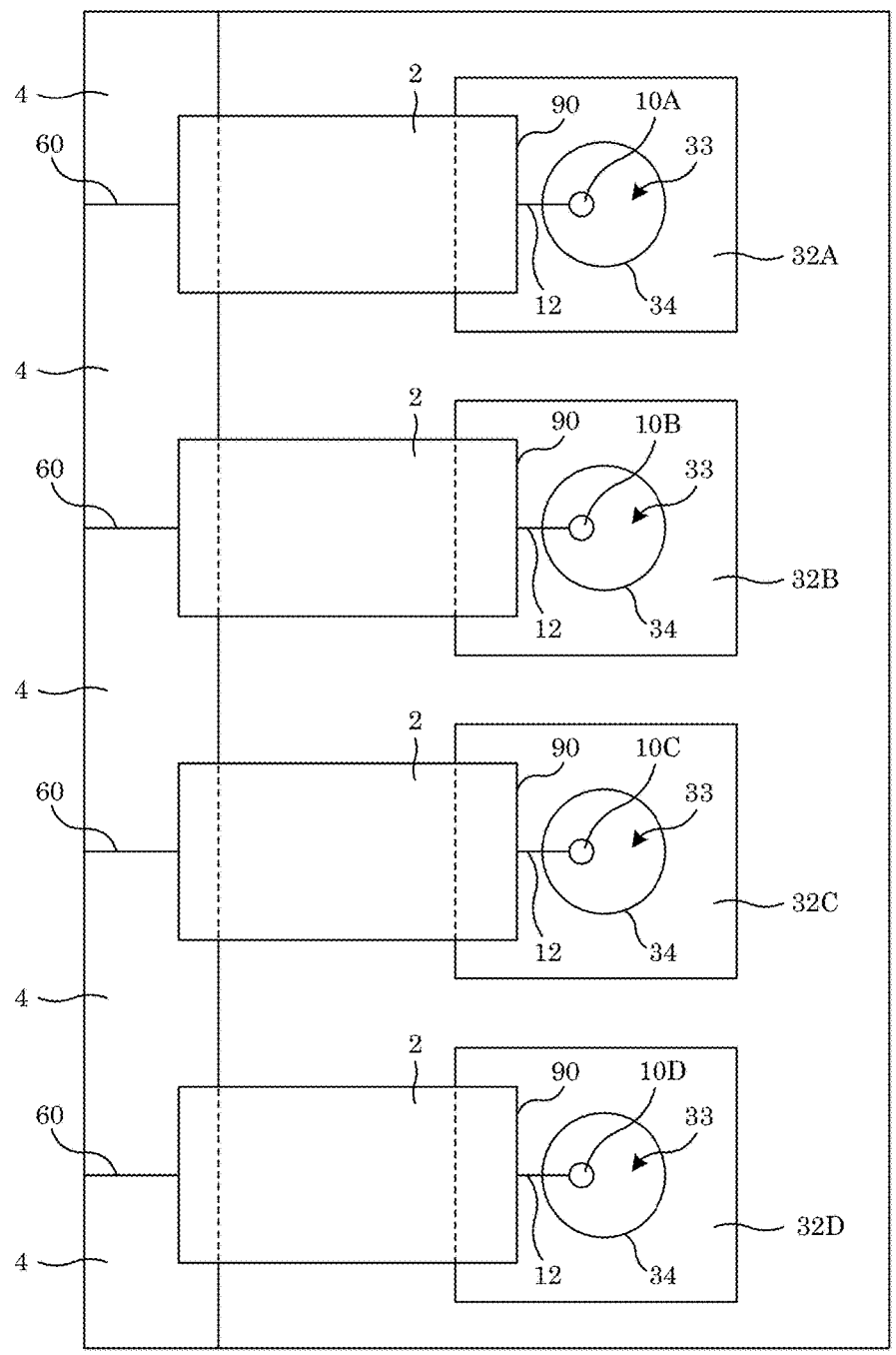
FIG. 18 shows a top view of a nucleic acid sequencer.
Figure 19:
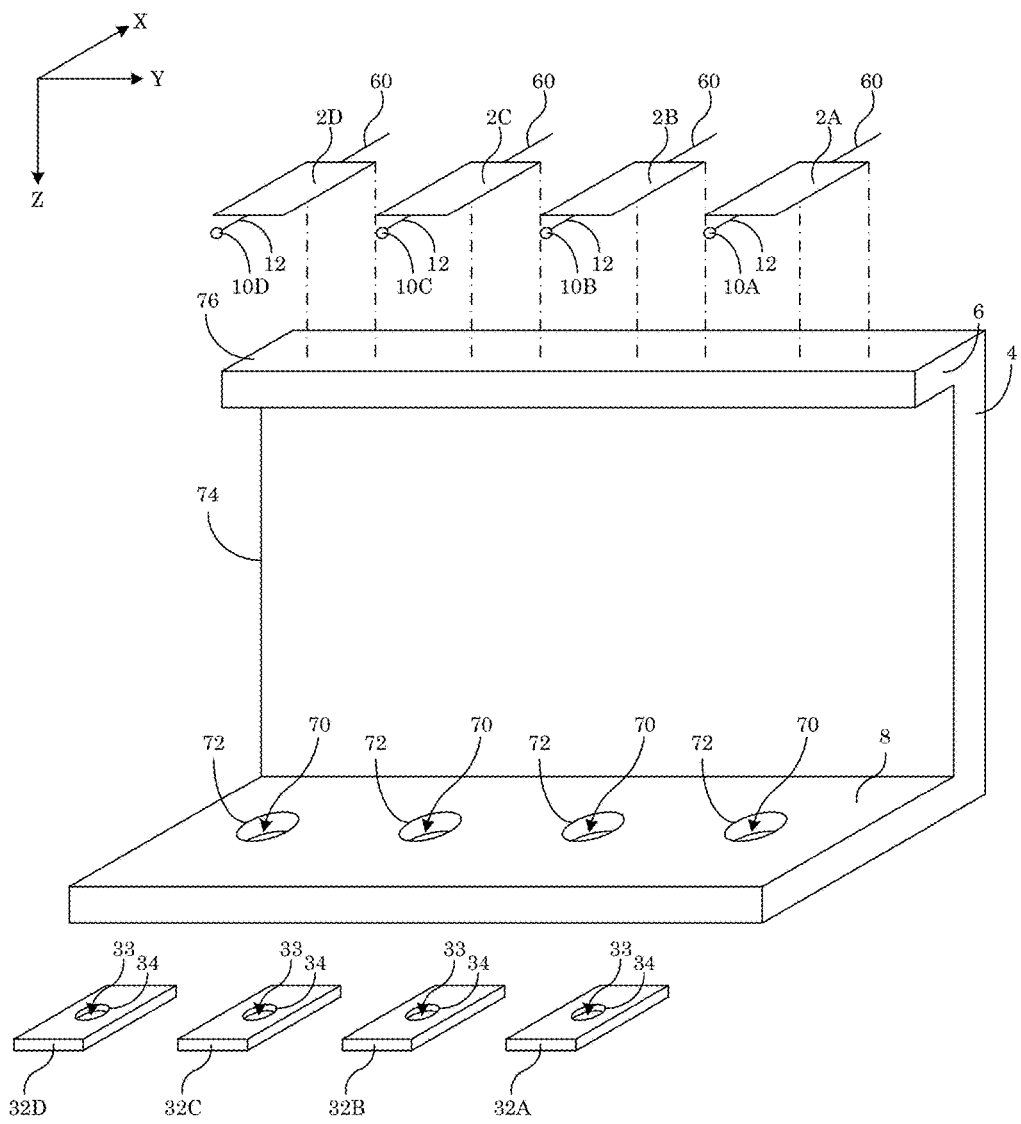
FIG. 19 shows an exploded view of the nucleic acid sequencer shown in FIG. 18.
Figure 20:
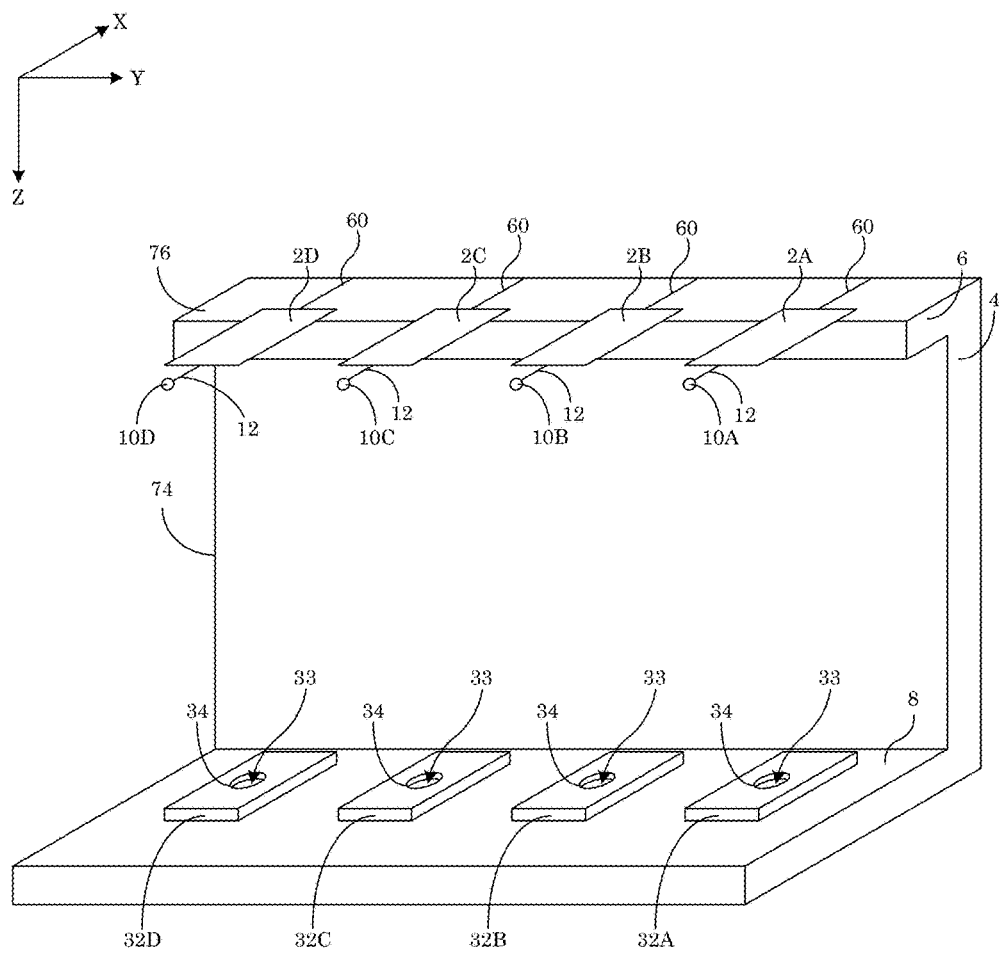
FIG. 20 shows a perspective view of the nucleic acid sequencer shown in FIG. 18.
Figure 21:
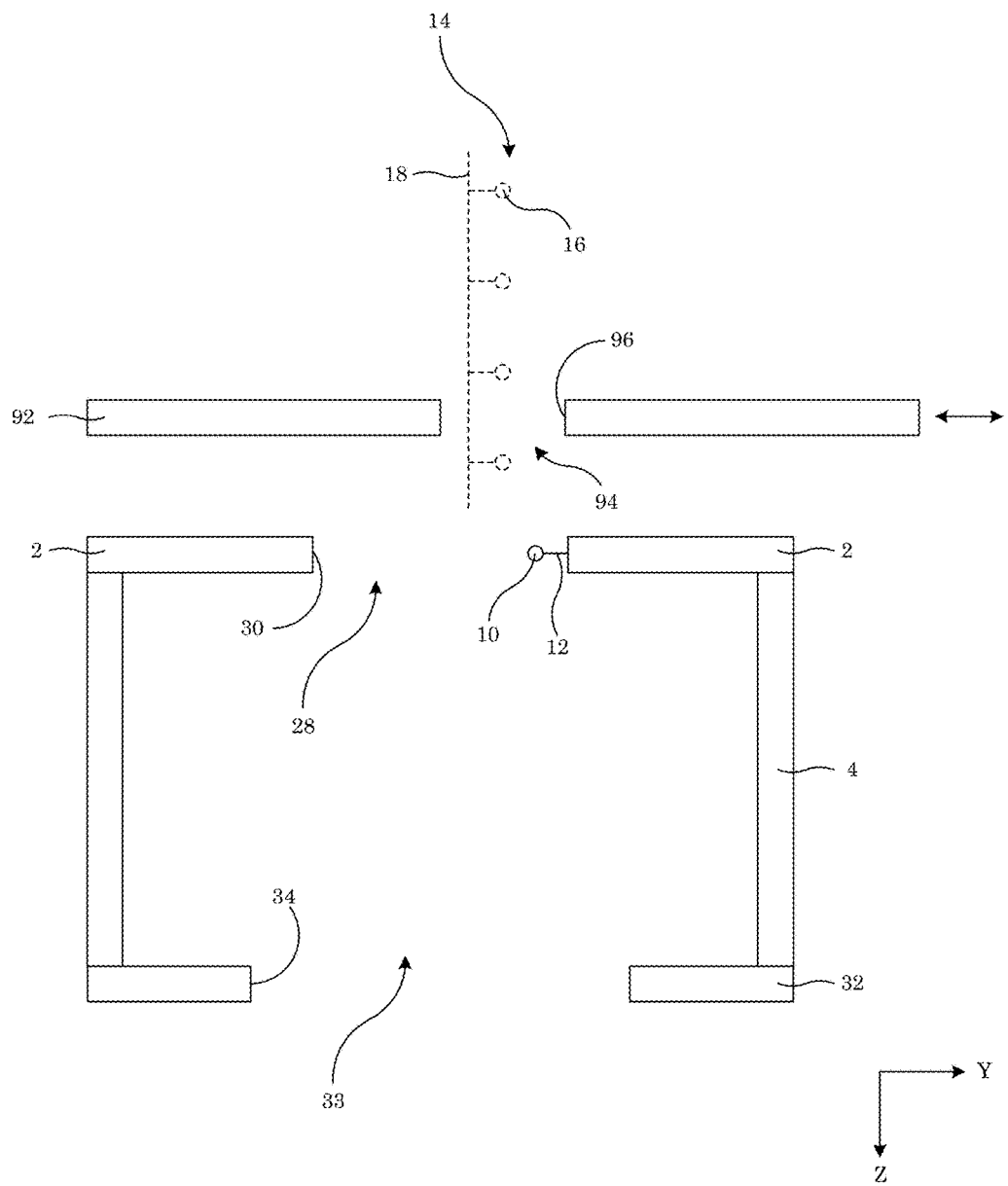
FIG. 21 shows a cross-section of a nucleic acid sequencer.

In an embodiment, with reference to FIG. 12, FIG. 13, FIG. 14, FIG. 15, FIG. 16, FIG. 17, FIG. 18, FIG. 19, and FIG. 20, nucleic acid sequencer 100 includes complementary base 10 disposed on atomically thin membrane 2 at edge 90 of atomically thin membrane 2. In an embodiment, nucleic acid sequencer 100 includes a plurality of atomically thin membranes 10 stackedly arranged to serially receive and to serially communicate single stranded nucleic acid 14 among the plurality of atomically thin membranes (e.g., 2A, 2B, 2C, 2D, and the like) as shown, e.g., in FIG. 15, FIG. 16, and FIG. 17. According to an embodiment, as shown in FIG. 18, FIG. 19, and FIG. 20, nucleic acid sequencer 100 includes a plurality of atomically thin membranes 2 (e.g., 2A, 2 B, 2 C, 2D, and the like) that include complementary base 10 (e.g., 10A, 10B, 10C, 10D, and the like) disposed thereon and laterally arranged to receive and communicate in parallel (e.g., synchronously or asynchronously) a plurality of single stranded nucleic acids 14 (e.g., 14A, 14B, 14C, 14D, and the like).

In an embodiment, nucleic acid sequencer 100 includes line member 92 disposed proximate to atomically thin membrane 24 aligning single stranded nucleic acid 14 with complementary base 10 disposed on atomically thin membrane 2. Here, alignment member 92 includes alignment aperture 94 bounded by wall 96, wherein alignment aperture 94 communicates single stranded nucleic acid 14 to atomically thin membrane 2. Alignment member 92 and atomically thin membrane 2 are spaced apart and can be a monolithic structure or separate item elements. It is contemplated that alignment member 92 moves laterally (e.g., in an x-y plane) separated at a distance from atomically thin membrane 2.

In the nucleic acid sequencer 100, solid electrode 32 is electrically conductive and part of the capacitive configuration with atomically thin membrane 2. As atomically thin membrane 2 flexes due to formation of base pair 22 and motion of single stranded nucleic acid 14, solid electrode 32 is immobile. In this regard, solid electrode 32 is rigid to maintain the shape and position. Exemplary materials for solid electrode 32 include degenerately doped silicon, copper, gold, or a combination thereof. A shape of solid electrode 32 can be rectangular, trapezoidal, or a combination thereof. A thickness of solid electrode 32 can be from 5 nanometers (nm) to 0.05 millimeters (mm), specifically from 5 nm to 50 micrometers (μm). An elastic modulus of solid electrode 32 can be from 50 GPa to 500 GPa, specifically from 50 GPa to 500 GPa, and more specifically from 50 GPa to 500 GPa.

Aperture 28 disposed in atomically thin membrane 2 can have an inner diameter from 1 nm to 50 μm, specifically from 1 nm to 50 μm, and more specifically from 1 nm to 50 μm.

In the nucleic acid sequencer 100, atomically thin membrane 2 is electrically conductive in a plane of atoms in atomically thin membrane 2. As used herein, "atomically thin" refers to materials that naturally form sheets that are one or a few (e.g., 2 or 3) atoms thick. Atomically thin membrane 2 is an element of the capacitive configuration with solid electrode 32. As atomically thin membrane 2 flexes due to formation of base pair 22 and motion of single stranded nucleic acid 14, solid electrode 32 is immobile. In this regard, although solid electrode 32 is rigid to maintain its shape and position, atomically thin membrane 2 flexes and changes selected distance D from solid electrode 32.

Exemplary materials for atomically thin membrane 2 include carbon, molybdenum, oxygen, sulfur, or a combination thereof. In an embodiment, atomically thin membrane 2 includes carbon arranged as graphene. In a certain embodiment, atomically thin membrane 2 includes molybdenum, oxygen, and sulfur arranged as molybdenum disulfide. A shape of atomically thin membrane 2 can be rectangular, trapezoidal, circular, or a combination thereof. A total thickness of atomically thin membrane 2 can be from 0.3 to 5 nanometers (nm) to millimeters (mm). A flexural rigidity of atomically thin membrane 2 can be from $1 \times 10^{-19}$ Pa·m$^3$ to $1 \times 10^{-17}$ Pa·m$^3$. Moreover, a bending modulus of atomically thin membrane 2 can be from 0.9 electron volts (eV) to 100 eV.

Aperture 28 disposed in atomically thin membrane 2 can have an inner diameter from 1 nm to 50 μm, specifically from 1 nm to 50 μm, and more specifically from 1 nm to 50 μm.

In the nucleic acid sequencer 100, complementary base 10 is disposed on atomically thin membrane 2 via linker 12. Complementary base 10 can be a nucleic acid such as an adenine, a cytosine, a guanine, a thymine, a uracil. Here, complementary base 10 can be derivatized with a functional group (e.g., thymine, cytosine, adenine 2,4 diaminopyrimidine, or a combination thereof, and the like) or with a substitutional atom (e.g., O, C, N, P, S, and the like) in a purine ring or pyrimidine ring of the nucleic acid of complementary base 10. In an embodiment, first complementary base 10A, second complementary base 10B, third complementary base 10C, and forth complementary base 10D independently includes adenosine, cytosine, guanine, and thymine. A number (e.g., 1, 2, 3, . . . , 100, and the like) of complementary bases 10 disposed on atomically thin membrane 2 can be any number effective to interact with single stranded nucleic acid 14 to produce flexural movement of atomically thin membrane 2 with respect to solid electrode 32 by which selected distance D changes. In an embodiment, three complementary bases or disposed on atomically thin membrane 2. In an embodiment, atomically thin membrane 2 is graphene. In a particular embodiment, atomically thin membrane 2 is molybdenum disulfide. In a certain embodiment, first atomically thin membrane 2A, second atomically thin membrane 2B, third atomically thin membrane 2C, and forth atomically thin membrane 2D independently include graphene, molybdenum disulfide, or a combination thereof.

Linker 12 can be a covalent bond or an atom (e.g., C—C bond, C—S bond thiol group (R—S—H), C atom, S atom, O atom and the like). Exemplary linkers 12 include C—S bond, thiol group, C—C bond, and the like, or a combination thereof.

In the nucleic acid sequencer 100, complementary base 10 disposed on atomically thin membrane 2 forms a hydrogen bond with particular nitrogenous bases 16 in single stranded nucleic acid 14 to form base pair 22. Base pair 22 includes a Watson-Crick base pair, a wobble base pair, or an unnatural base pair. Single stranded nucleic acid 14 can include adenine, cytosine guanine, thymine, uracil, or a combination thereof. Nitrogenous bases 16 independently can be a nucleic acid containing bases such as an adenine, a cytosine, a guanine, a thymine, a uracil. Here, nitrogenous base 16 can be derivatized with a functional group (e.g., cy3 dye, cy5 dye, fluorescein, or a combination thereof, and the like) or with a substitutional atom (e.g., O, C, N, P, S, and the like) in a purine ring or pyrimidine ring of the nucleic acid of nitrogenous base 16. Backbone 18 can include deoxyribose, phosphate group, or a combination thereof.

In the nucleic acid sequencer 100, spacer member 4 is electrically insulating to electrically insulate atomically thin membrane 2 from solid electrode 32. Further, spacer member 4 is rigid so not to bend or change shape under interaction with a single stranded nucleic acid 14. Exemplary materials for spacer member 4 include silica, undoped silicon, or a combination thereof. A shape of spacer member 4 can be rectangular, trapezoidal, circular, or a combination thereof. A thickness of spacer member 4 can be from 1 nanometers (nm) to 1 micrometer (µm). An elastic modulus of spacer member 4 can be from 40 GPa to 500 GPa.

Aperture 70 disposed in spacer member 4 (e.g., first wall 76 or second wall 78) can have a width or diameter from 1 nm to 50 µm, specifically from 1 nm to 50 µm, and more specifically from 1 nm to 50 µm.

In the nucleic acid sequencer 100, alignment member 92 is electrically conductive, electrically semiconductive, electrically insulating, or combination thereof. Exemplary materials for alignment member 92 include silica, coated silica, Teflon, or a combination thereof. A shape of alignment member 92 can be rectangular, circular, trapezoidal, or a combination thereof. A thickness of alignment member 92 can be from 1 nanometer (nm) to 1 millimeter (mm). An elastic modulus of alignment member 92 can be from 50 GPa to 500 GPa.

Alignment aperture 94 disposed in alignment member 92 can have an inner diameter from 1 nm to 50 µm, specifically from 1 nm to 50 µm, and more specifically from 1 nm to 50 µm.

Figure 22:
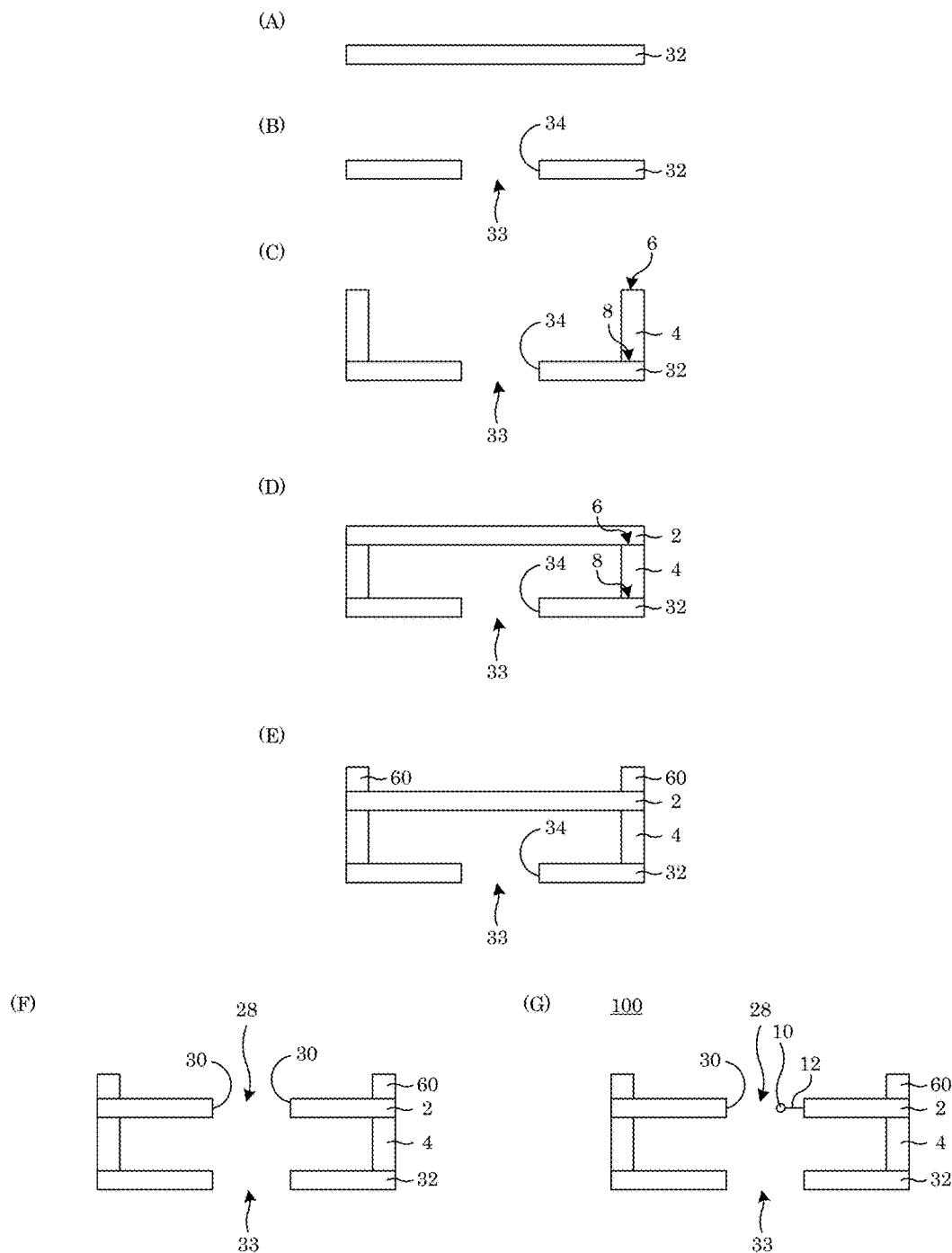
FIG. 22 shows various steps in making a nucleic acid sequencer.

In an embodiment, with reference to FIG. 22, a process for making nucleic acid sequencer 100 includes providing solid electrode 32 (panel A); disposing aperture 33 bounded by wall 34 in solid electrode 32 (panel B); disposing spacer member 4 on solid electrode 32 (panel C); disposing atomically thin membrane 2 on pacer member 4 (panel D); disposing wire 60 on atomically thin membrane 2 (panel E); forming aperture 28 bounded by wall 30 in atomically thin membrane 2 (panel F); and covalently disposing complementary base 10 on atomically thin membrane 2 (panel D).

In the process, providing solid electrode 32 includes photolitographically deposited, nanomechanically deposited, or epitaxially grown slab of electrical conductor.

In the process, disposing aperture 33 bounded by wall 34 in solid electrode 32 includes subjecting a focused electron beam or ion beam to solid electrode 32.

In the process, disposing spacer member 4 on solid electrode 32 includes photolitographically depositing or epitaxially growing spacer members 4 on top of the surface of solid electrode 4.

In the process, disposing atomically thin membrane 2 on spacer member 4 includes nanomechanically depositing previously synthesized atomically thin membrane of appropriate dimensions and structure (using e.g. vapor deposition process or via mechanical exfoliation) upon spacer member 4.

In the process, disposing wire 60 on atomically thin membrane 2 includes photolitographically depositing or printing an electrically conductive layer to form an electrical connection with atomically thin membrane 2, or depositing an electrically conductive layer on spacer member 4 prior to depositing of atomically thin membrane 2 upon spacer member 4.

In the process, forming aperture 28 bounded by wall 30 in atomically thin membrane 2 includes subjecting a focused electron beam or ion beam to atomically thin membrane 2.

In the process, covalently disposing complementary base 10 on atomically thin membrane 2 includes using a wet chemistry process, immersing atomically thin membrane 2 in an appropriate solution of complementary bases 10, or using an electrostatically biased atomic force microscope tip to deposit complementary base 10 on atomically thin membrane 2.

Additionally, the process further can include microscopy-guided device assembly to align aperture 28 to aperture 32; chemically or electrostatically remove impurities left over after deposition processes, add additional micro/nanofluidic guides for DNA sample 16; adding driver electrodes to control the movement of DNA sample 16 through sequencer 100.

Nucleic acid sequencer 100 has numerous beneficial uses, including determining a sequence of nitrogenous bases 16 of single stranded nucleic acid 14. In an embodiment, a process for determining a sequence of nitrogenous bases 16 of single stranded nucleic acid 14 includes preparing aqueous single-strand nucleic acid 14 from a DNA duplex by employing a recombination protein RecA from bacteria (e.g., E. coli). Immersing four stacked nucleic acid sequencers 100 into aqueous solution and disposing of nucleic acid 14 into the solution proximate to alignment member 92. The sequencers 100 can differ by an identity of complementary base 10 to detect different nitrogenous bases. In a first sequencer 100, base 10 includes cytosine to detect guanine. In a second sequencer 100, complementary base includes guanine to detect cytosine. Applying a driver electric field perpendicularly to the plane of alignment member 92, solid electrode 32, and atomically thin membrane 2 to facilitate insertion of nucleic acid into stacked sequencers 100. Applying additional constant voltage between solid electrode 32 and atomically thin membrane to power sequencer 100. As nucleic acid 14 begins to sequentially traverse sequencers 100 under the driver electric field, sequencing process starts. Identifying the DNA sequence is performed by assigning a nucleotide occurrence to the recorded current changes, which stand out from the background noise. For example, consider nucleic acid sample 14, in which the sequence of bases 16 is ACGTACGTACGT (SEQ ID NO: 1). As a result, sequencer 100 detects aimed at nitrogenous base adenine (A) and produces an increase in electrical current such as A - - - A - - - A - - - . Similarly, sequencer 100 that detects nitrogenous base cytosine (C) produces that electrical current due to the sequence - C - - - C - - - C - - . Sequencer 100 that detects nitrogenous base guanine (G) produces electrical current in response to the sequence - - G - - - G - - - G - . Sequencer 100 that detects nitrogenous base guanine (T) produces electrical current in response to the sequence - - - T - - - T - - - T. The process can include digitizing and storing these signals in computer memory. Because the distance between stacked sequencers 100 and strength of the driver electric field (and thus the rate of motion of sample 14) is known beforehand, the time delays between the four signals are known, analysis of the electrical signals from the four sequencers 100, e.g., combining the temporal responses from sequencer 100, provides the sequence of single stranded nucleic acid 14 as SEQ ID NO: 1.

In an embodiment, sequencers 100 are laterally disposed instead of stacked, and four identical single stranded nucleic acids 14 are detected by four sequencers 100, wherein each sequencer 100 includes a different complementary base 10. Here, each sequencer 100 simultaneously detects individual single stranded nucleic acids 14

Nucleic acid sequencer 100 has numerous advantageous and beneficial properties. In an aspect, nucleic acid sequencer 100 provides cost-effective sequencing of single-strand nucleic acid with accuracy at millions of bases per second.

Advantageously, unexpectedly, and surprisingly, nucleic acid sequencer 100 provides scalability in terms of membrane dimensions, which allows for model-based engineering of the nucleic acid sequencer 100 and optimization of electronic signals subject to measurement. In addition, capacitive currents from nucleic acid sequencer 100 provides sequencing accuracy that increases with sequencing speed.

The articles and processes herein are illustrated further by the following Examples, which are non-limiting.

EXAMPLES

Example 1

Equations in this Example Start at S1.

An aqueous functionalized molybdenum disulfide nanoribbon suspended over a solid electrode as a capacitive displacement sensor was designed to determine a sequence of nitrogenous bases in nucleic acid, e.g., deoxyribonucleic acid (DNA) sequence. Detectable sequencing events arise from the combination of Watson-Crick base-pairing with the ability of appropriately sized atomically thin membranes to flex substantially in response to sub-nanonewton forces. We employ carefully designed numerical simulations and theoretical estimates to demonstrate excellent (79% to 86%) raw target detection accuracy at ~70 million bases per second and electrical measurability of the detected events. In addition, we demonstrate reliable detection of repeated DNA motifs. The nucleic acid sequencer is base-specific, a high-throughput electronic DNA sequencing device and cost-effective.

Aiming for a realistic and naturally nucleotide-specific sequencer not relying on either ionic currents, or field effects, we simulated a strain-sensitive graphene nanoribbon (GNR) at room temperature in aqueous environment. As proposed, a single-strand DNA (ssDNA) molecule was translocated via a nanopore in a locally suspended GNR at a given rate. The interior of the nanopore was chemically functionalized with a nucleobase complementary to the target base subject to detection. As target ssDNA bases pass, Watson-Crick base-pairing temporarily deflects the nanoribbon out of plane, in turn causing changes in the GNR conductance via near-uniaxial lattice strain. A single-measurement sequencing accuracy near 90% without false positives was estimated for the G-C pair at the effective sequencing rate of ~66 million nucleotides per second. Engineering graphene's hydrophobicity via local non-covalent coating is possible to alleviate adsorption of nucleic acid on graphene. Molybdenum disulfide ($MoS_2$) does not adsorb DNA.

Density Functional Theory (DFT) simulations, room temperature molecular dynamics (MD) simulations, and analytical calculations were combined to investigate the operation of a nucleobase-functionalized monolayer $MoS_2$ nanoribbon as a central element in a displacement sensor aimed at selective detection of nucleotides. A nanoscale flat-plate capacitor, in which one of the plates is selectively deflected out of plane by the passing target nucleotides during DNA translocation. The sequencing readout is then performed as a measurement of the time-varying capacitance. In addition, the relatively high bending rigidity of $MoS_2$ results in significantly reduced flexural fluctuations, reducing readout signal noise. At the same time, flexibility of monolayer $MoS_2$ provides considerable out-of-plane nanoribbon deformation in response to the forces required to break up a Watson-Crick pair. Functionalization of $MoS_2$ with organic molecules provides determination of a sequence of nitrogenous bases in a single stranded nucleic acid, e.g., DNA.

Figure 24:
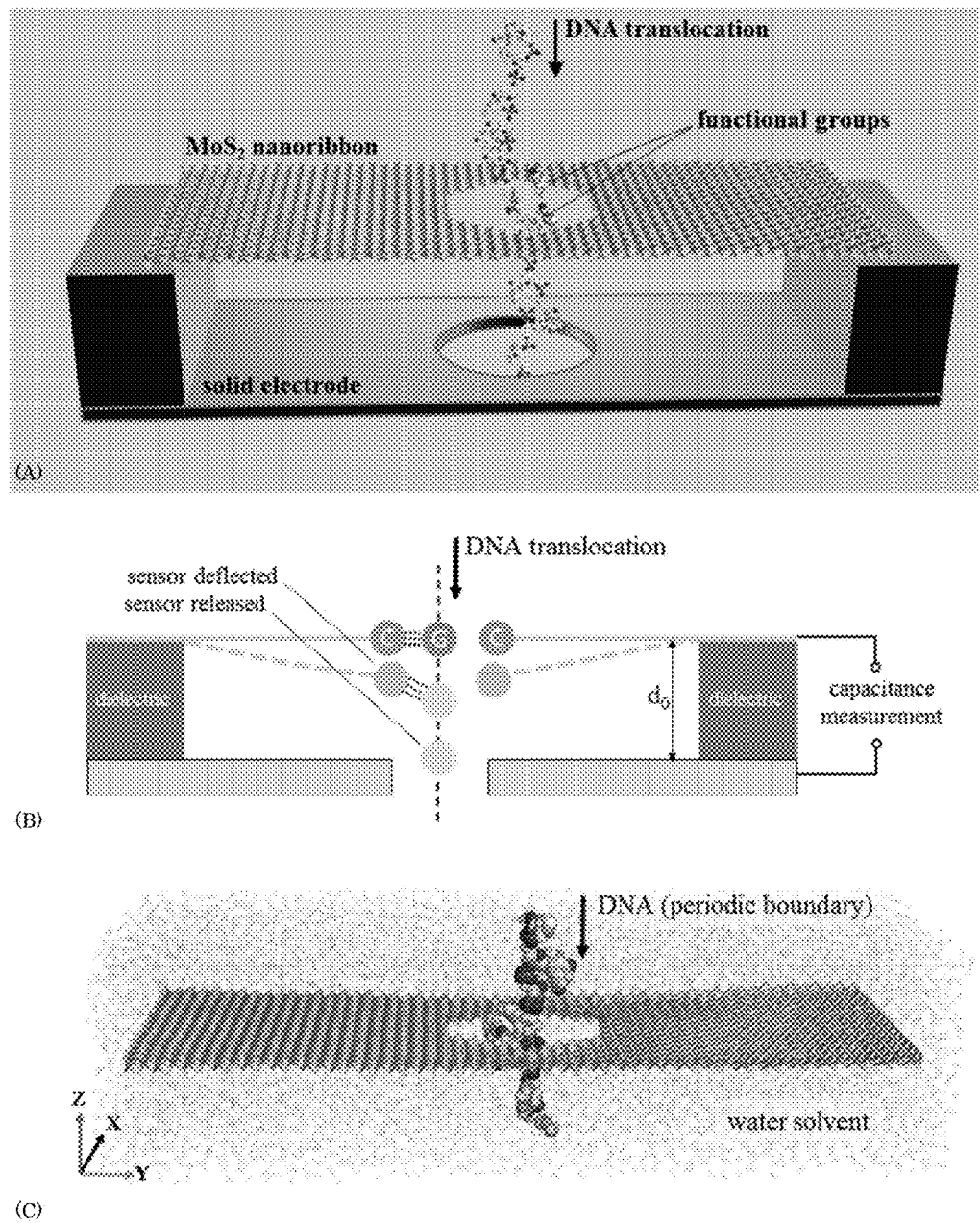
FIG. 24 shows capacitive displacement of a nucleic acid sequencer sensor in panels A and B and disposal of the nucleic acid sequencer in water in panel C, wherein dotted lines in panel B are hydrogen bonds.

The nucleic acid sequencer that detected guanine (G) base is shown in FIG. 24, wherein and interior of the pore formed in the $MoS_2$ nanoribbon is functionalized by cytosine (C) molecules, which are complementary to G. The metal electrode at the bottom of the proposed sensor forms a flat-plate capacitor with the locally suspended monolayer $MoS_2$ nanoribbon. In such a setup, the modification of capacitance caused by the temporary deflection of the nanoribbon is subject to measurement, as mentioned earlier and depicted in panel B of FIG. 24). Further, the capacitance variation in response to the ribbon deflections and the resulting electrical signal are measurable using existing integrated circuits without requiring microscopy methods. Following the Watson-Crick base-pairing principle, the "raw" (single-read) DNA sequence can then be obtained using at least two different strategies. In one, the sequence is produced in a single DNA translocation via a stack of four sensors (e.g. cytosine-functionalized nanoribbon aimed at detecting guanine and vice versa, etc.). Alternatively, the sequence may be constructed from simultaneous scans of identical DNA copies via four sensors, each aimed at a single base type. In principle, the presented displacement sensor is expected to be applicable to all sufficiently flexible, electrically conductive (under appropriately selected bias) membranes, including graphene.

The system subject to MD simulations is shown in panel C of FIG. 24. The interior of the pore in the $MoS_2$ nanoribbon is functionalized by two cytosine molecules. Functionalization with a cytosine moiety was achieved via a single covalent S—C bond with the cytosine carbon at position six. The orientation of the functional group relative to $MoS_2$ plane was confirmed by DFT energy minimization, as detailed in Example 2.

DFT simulations were performed on a system consisting of a triangular monolayer $MoS_2$ cluster with a cytosine molecule attached as shown in FIG. 30. In the MD simulations, the nanoribbon dimensions are $L_x$=4.5 nm×$L_y$=15.5 nm; the nanopore diameter is ~2.5 nm. The ends of the nanoribbon were position-restrained to mimic local binding to the supporting substrate (see panel A of FIG. 24). Each simulated ssDNA sample consisted of six bases. To reduce the computational cost and enable continuous ssDNA translocation, each DNA strand was made periodic in the Z-direction, as shown in panel C of FIG. 24. Prior to production simulations, periodic ssDNA samples were pre-stretched along Z-direction. A total of six potassium ions were added to the solvent to counteract the negative net charge of the six-base DNA samples. Weak in-plane harmonic position restraints with a constant of $$200.0 \frac{kJ}{mol\ nm^2}$$

were applied to the six $CH_2$-bound oxygens of the phosphate moieties, mimicking the effect of an insertion aperture, which maintains the DNA position reasonably close to the center of the nanopore, while allowing rotation around Z-axis.

DFT simulations for determining the stability of the functional group (cytosine) and its orientation relative to the MoS$_2$ plane were performed using the CP2K package. Perdew, Burke and Ernzerhof (PBE) exchange functional, Gaussian plane-wave pseudopotentials, and the DZVP basis set were used. In addition, D3 non-local correction was applied. All MD simulations were performed using GROMACS 5.1.2 package. The MD models of the DNA and functionalized MoS$_2$ were based on the AMBER94 force-field. The intramolecular interactions in MoS$_2$ were refined to reproduce the basic mechanical material properties in a reasonable manner. The charges of sulfur and molybdenum atoms were set according to quantum-mechanical calculations. The system was immersed in a rectangular container filled with explicit water molecules, using the TIP4P model. Prior to the production MD simulations, all systems underwent NPT relaxation at T=300 K and p=0.1 MPa. The production simulations of the DNA translocation via nanopores were performed in an NVT ensemble at T=300 K, maintained by a velocity-rescaling thermostat with a time constant of 0.1 ps.

Figure 25:
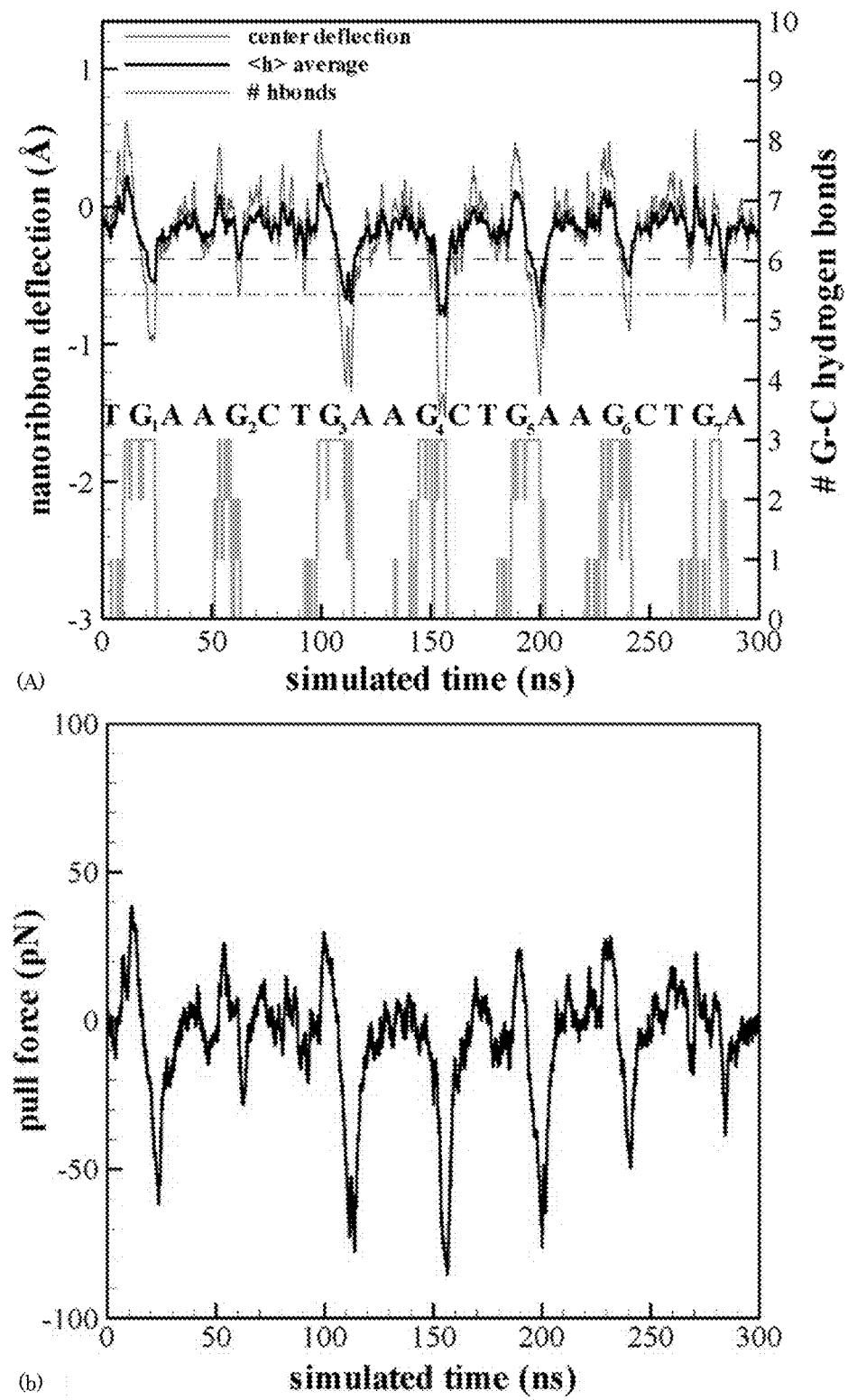
FIG. 25 shows maximum (center) and average deflection ⟨h⟩ of an atomically thin membrane that includes $MoS_2$ along with the number of G-C hydrogen bonds in panel A, and ssDNA pulling force in panel B as a function of simulation time; DNA translocation rate was 5 cm/s; a low-pass filter with 800 MHz cutoff was applied to the raw deflection and pulling force data.

A sample sequence TGAAGC was set up as shown in panel C of FIG. 24 and translocated for 300 ns at an average prescribed rate of 5 cm/s in the negative Z-direction. At the given rate and simulated time, the DNA travels 15 nm along the prescribed direction. Therefore, given a periodic boundary in the Z-direction and the fact that the pre-stretched six-base DNA sample length was approximately 4.4 nm along the Z-axis, the sample sequence is expected to traverse the pore 15 nm/4.4 nm≈3.4 times. Therefore, the complete test sequence, as seen by the functional groups in the nanopore, was close to TGAAGC|TGAAGC|TGAAGC|TG (SEQ ID NO: 2) (underlined base inside the pore at the start of the simulation) with a total of seven guanine passages expected. The nanoribbon deflection data (maximum deflection at the nanoribbon center and average deflection $$\langle h \rangle = \frac{1}{N_{Mo}} \sum_{N_{Mo}} z_i$$

calculated from a total of $N_{Mo}$ molybdenum atoms), together with the number of hydrogen bonds as functions of simulated time, are shown in panel A of FIG. 25. Seven binding events occurred as shown in panel a of FIG. 25. Except for G$_2$, for which the duration of binding is the shortest, all hydrogen bond formation events are accompanied by deflection events beyond the provided thresholds. At the same time, no false-positive deflections beyond thresholds occur, which suggests an overall raw detection error near one out of seven, or 14%. The vertical force causing selective deflections can be evaluated directly from panel B of FIG. 25, where the DNA external pulling force is plotted as a function of simulated time. At the peaks corresponding to the deflection maxima, the critical force required to break up the resulting G-C pairs is obtained. From averaging over six "useful" deflection events, the force peak magnitude is ≈60 pN.

In the capacitive configuration, the relative change in capacitance is straightforward to estimate as $$\frac{\Delta C}{C_0} \approx -\frac{\langle h \rangle}{d_0},$$

assuming $\langle h \rangle \ll d_0$, where $d_0$ is the plate separation, as defined in panel B of FIG. 24. The value of $\langle h \rangle$ averaged over the six deflection events in panel A of FIG. 25 is $\langle h \rangle_{ave} \approx 0.6$ Å, and thus with $d_0$=1.0 nm, $$\frac{\Delta C}{C_0} \approx 6\%.$$

The subject of measurement, however, is not the value of capacitance, but the transient electrical current $$i_d(t) = V_0 \frac{dC(t)}{dt}$$

arising because of deflections of atomically thin membrane 2 and proportional to the rate of these deflections, as shown below.

Figure 26:
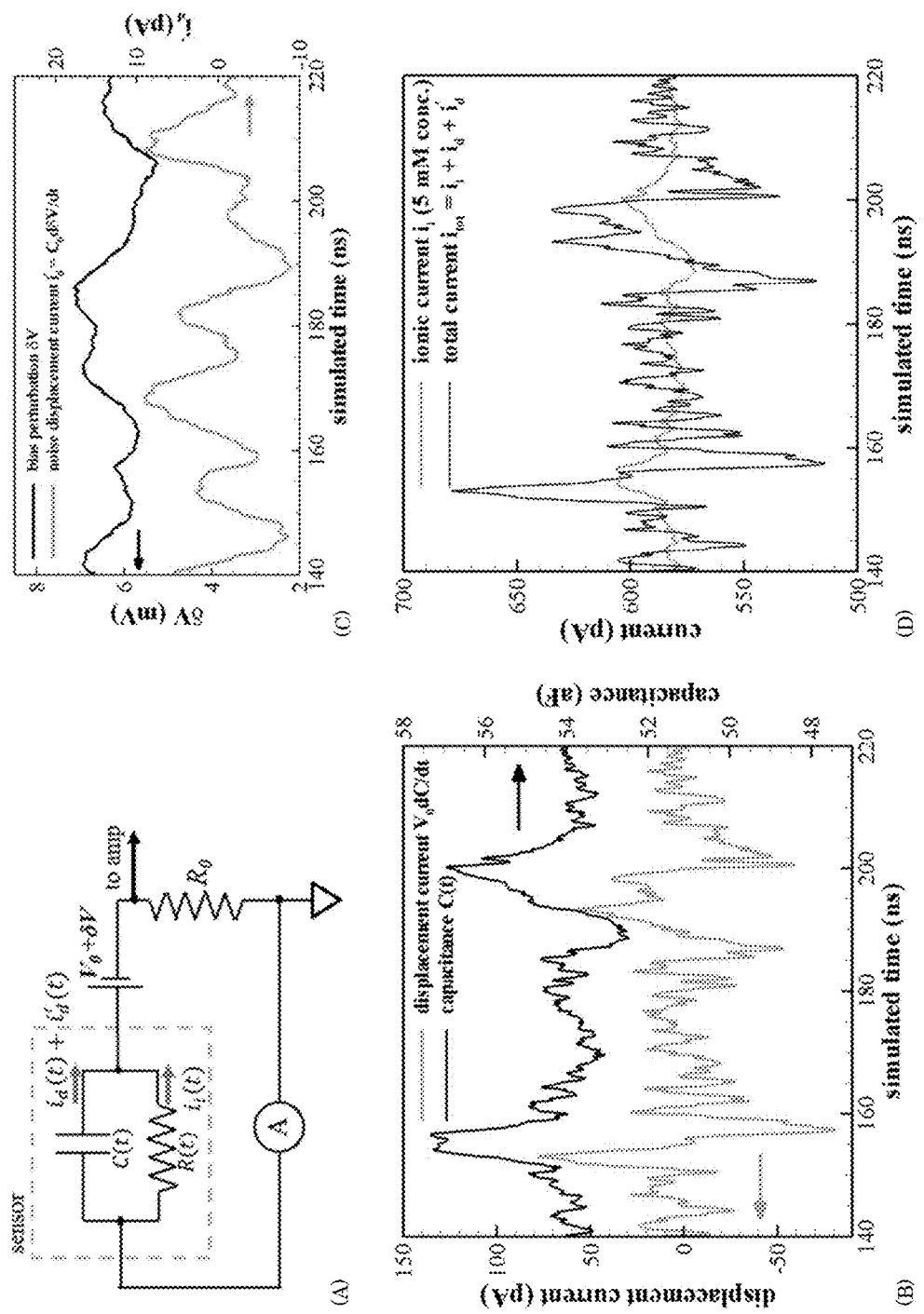
FIG. 26 shows an equivalent circuit for a nucleic acid sensor in panel A, displacement current and capacitance as functions of simulated time in panel B, bias perturbation contributed by the translocating DNA sample in panel C, and ionic current contribution and the total current in the circuit in panel D.

Regarding panel A of FIG. 26, presence of electrolyte ions in the aqueous system containing DNA, an ionic conductor is connected in parallel with the ideal capacitor formed between the MoS$_2$ membrane and the solid electrode. A selected constant voltage V$_0$ is applied across the sensor and the total current through the circuit is the effective measured signal, which is fed to the amplifier stage as a voltage drop across a small resistive load R$_0$, as shown in panel A of FIG. 26. An additional noise voltage contribution $\delta V \ll V_0$ is also present in the system, as discussed further. Only first-order perturbative effects are considered here.

The total current in the circuit is $I_{tot}(t)=[i_d(t)+i_d'(t)]+i_i(t)$, where $$i_d(t) = V_0 \frac{dC(t)}{dt} \left(\text{with } C(t) \approx C_0\left(1 - \frac{\langle h \rangle(t)}{d_0}\right)\right)$$

is the displacement current associated with membrane deflections, $$i_d'(t) = C_0 \frac{d\delta V(t)}{dt}$$

is the displacement current noise from voltage perturbations $\delta V(t)$ contributed by the solvent, dissolved ions, as well as the ssDNA, and $i_i(t)$ is the ionic leakage current, also subject to perturbation due to varying electric field between the capacitor plates. Here, plate charge perturbation is contributed by the change in the capacitor geometry due to membrane deflections, while the density of mobile charge carriers in the semiconducting MoS$_2$ ribbon remains constant.

A data excerpt from the simulation that yielded the results in FIG. 25 was used directly to reveal detailed time dependence of the electrical response to membrane deflections. In particular, C(t) and $i_d(t)$ are plotted in panel B of FIG. 26 for V$_0$=150 mV. As expected, $i_d(t)$ oscillates around zero overall and produces pairs of transient peaks more than 50 pA when the membrane deflects and slips back. In absence of other contributions, these current spikes represent the primary signal subject to detection.

The noise arising from fast fluctuations of the solvent and the dissolved ions is expected to be in the frequency range far beyond that of the "useful" signal. However, the electrostatic bias noise due to the motion of the ssDNA sample, including its translocation and any spurious movements, occurs within the timescale of interest. Conveniently, the noise current $$i'_d(t) = C_0 \frac{d\delta V(t)}{dt}$$

can be estimated directly from the simulated electrostatics. We note that δV(t) can be obtained from the time-dependent solution of the Poisson's equation in the region occupied by the $MoS_2$ membrane, as contributed by the DNA atomic charges. As shown in panel C of FIG. 26, δV(t) indeed varies relatively slowly during DNA translocation and the resulting displacement current noise $i_d'(t)$ amplitude is only 10% to 15% of the $i_d(t)$ peaks in panel B of FIG. 26. This noise contribution further decreased with increasing membrane size due to the ~1/r dependence of the electrostatic potential perturbations contributed by a near-linear strand of DNA perpendicular to the membrane.

Finally, the ionic leakage current $i_i(t)$ and the total current $I_{tot}(t)=[i_d(t)+i_d'(t)]+i_i(t)$ through the circuit are estimated. The ionic current between the capacitor plates of length L and width w (assuming the "worst-case" scenario, in which each ion transfers charge to the membrane) is estimated for dissolved KCl as $$i_i(t) = \frac{nwLqV_0(\mu_K + \mu_{Cl})}{d_0}\left(1 - \frac{\langle h \rangle(t)}{d_0}\right),$$

where n, $\mu_K$, and $\mu_{Cl}$ are the electrolyte concentration and the ionic mobilities, respectively. A 5 mM KCl concentration is assumed. As shown in panel D of FIG. 26, the ionic contribution results in a significant overall current baseline, subject to transient fluctuation via $$\frac{\langle h \rangle(t)}{d_0}.$$

Importantly, however, deflection-induced variation of the total current $I_{tot}(t)$ remains dominated by the displacement current $i_d(t)$ for the selected salt concentration. De-ionization of DNA samples, membrane passivation, or providing an alternative conductive path for the mobile electrolyte ions via additional fields can be included when determining a sequence of nitrogenous bases in the nucleic acid.

Both $\langle h \rangle (\propto L^3/w)$ and $C_0 \propto Lw/d_0$ are subject to refined design in terms of the ribbon dimensions. The value of $d_0$ (and thus the bias voltage $V_0$) should then also be optimizable for larger nanoribbons to achieve optimal signal contributions, while remaining within the reach of device fabrication capability.

The data presented in FIG. 25 corresponded to a DNA sequence . . . TGAAGC . . . , in which target guanines were separated by two non-target bases. Given that the proposed detection mechanism relies on hydrogen bond formation and subsequent deflections of the nanoribbon, a realistic motif consisting of repeated target nucleotides may present a sequencing challenge. This challenge is two-fold, including "skipping" detection of the targets due to their close spacing (especially when the expected maximum deflections of a given nanoribbon are comparable to the base spacing), as well as guanine-guanine interactions within an ssDNA chain, which may cause "interference" during interactions with the functional groups at the pore interior. The latter can arise from hydrogen bonding between a hydrogen atom of the amino group and the carboxylic oxygen of the neighboring guanine moieties.

Figure 27:
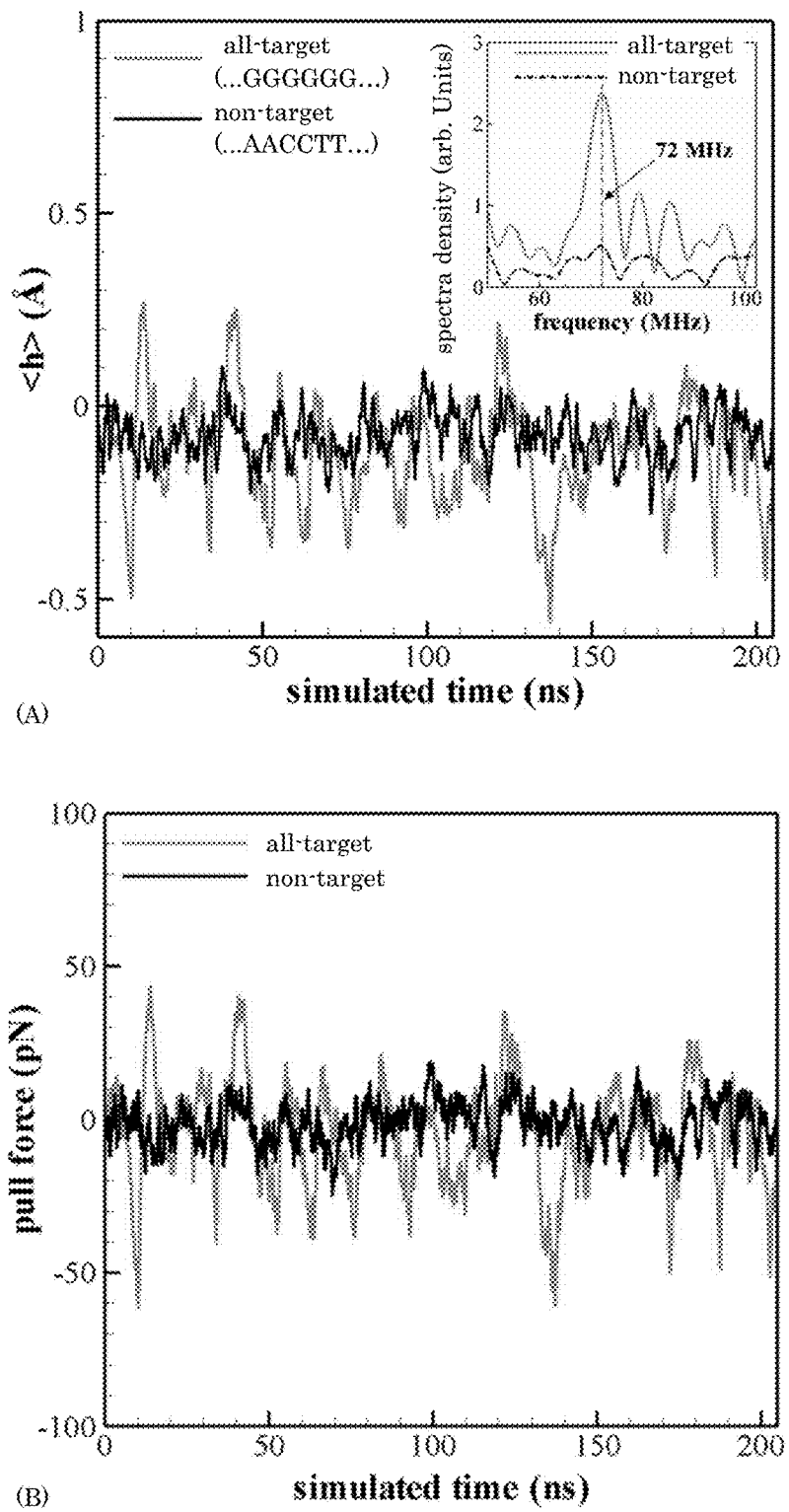
FIG. 27 shows average nanoribbon deflections ⟨h⟩ (A) and ssDNA pulling forces (B) as functions of simulated time for the repeated all-target sequence and the non-target sequence; inset in (A) shows frequency spectra obtained from the presented time-domain data; DNA translocation rate was 5 cm/s, and a low-pass filter with 800 MHz cutoff was applied to the raw deflection data.

To detect a repeated target sequence and to provide a comparison with the results obtained for a sequence containing no target bases, additional translocation simulations were set up as described above and run for 200 ns. The results obtained for the test sequences . . . GGGGGG . . . (all-target) and . . . AACCTT . . . (non-target) are shown in FIG. 27. For the all-target sequence, 11 distinct deflection events (with an average of $\langle h \rangle_{ave} \approx 0.37$ Å) are observed, while only thermal fluctuations are observed for the non-target case. In 200 ns, a total of 14 complete target base passages are expected and, given that 11 deflection events are observed, the raw detection accuracy, as calculated from the presented data, is $11/14 \approx 79\%$. To resolve the presence of a repeated sequence better, we calculated the Fourier spectra of the time-dependent deflection data, as shown in the inset of in panel A of FIG. 27. In contrast with the spectral distribution obtained for the non-target sequence, an outstanding $f_0=72$ MHz peak is observed for the all-target case, corresponding to a base spacing of $v_{scan} \times 1/f_0 = 6.94$ Å. Given the ≈4.14 nm length of the periodic pre-stretched all-target sample consisting of six bases along the Z-axis, the event periodicity from a purely geometric standpoint is 4.14 nm/6=6.90 Å, in excellent agreement with the periodicity obtained from the spectrum. Therefore, given that the translocation rate is known, a continuous calculation of the spectral properties of the deflection data (performed within an appropriately selected time "window") can serve as an effective repeated sequence detection measure.

Figure 28:
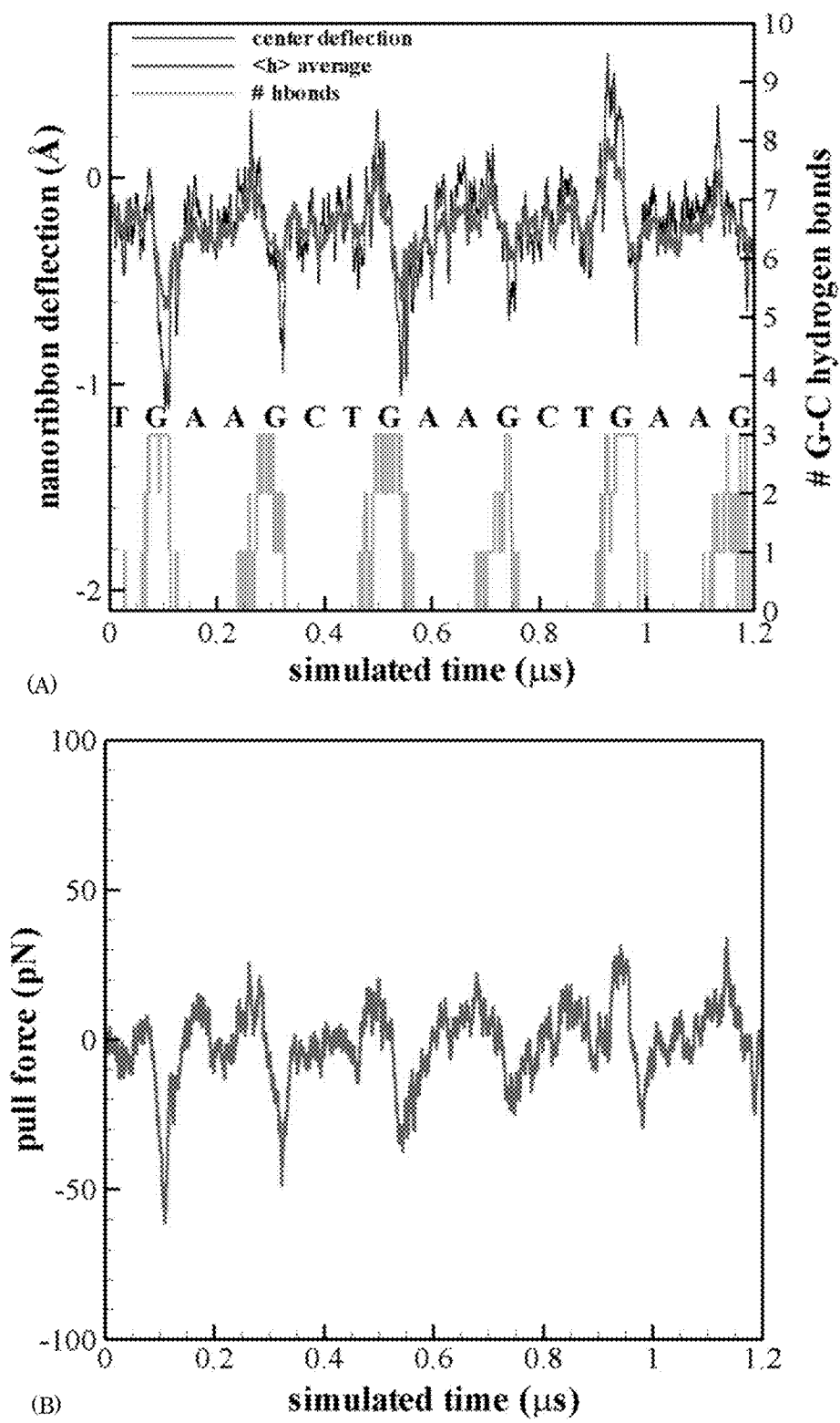
FIG. 28 shows maximum (center) and average deflection ⟨h⟩ of an atomically thin membrane that included $MoS_2$ along with the number of G-C hydrogen bonds (A), and ssDNA pulling force (B) as functions of simulated time.

The results presented in FIG. 25 and FIG. 27 were obtained for the DNA translocation rate of 5 cm/s (corresponding to the read rate 14 ns/base or ~70 million bases per second). As shown in the discussion accompanying FIG. 27, the useful signal frequency range associated with the 5 cm/s translocation rate is well within the capacity of the currently available measurement equipment. We performed an additional 1.2 μs long ssDNA translocation simulation at 1 cm/s, corresponding to 70 ns/base or 14 million bases per second. For the DNA sequence, identical to that in FIG. 25, the results are presented in FIG. 28. Except for the short binding event at ~0.75 μs, distinct nanoribbon deflections accompany all the target binding events, like the results in FIG. 25. Therefore, translocation rate reduction by a factor of five does not appear to degrade target detection rate.

Another nucleic acid sequencer is shown in FIG. 29, wherein the ssDNA sample is shown to be translocated perpendicularly to the functionalized edge of the locally suspended membrane, omitting the nanopore entirely. Such a geometry still requires a solid aperture for proper positioning of the DNA sample relative to the sensor. In this configuration, a twisting deformation occurred in addition to bending and stretching, possibly modifying the useful signal estimates for the readout scheme previously proposed for graphene. A relative change in capacitance due to deflection is $$\frac{\Delta C}{C_0} \approx \frac{\langle h \rangle}{d_0}.$$

The distribution of the out-of-plane atomic positions throughout the membrane is shown in panel B of FIG. 29, as obtained for a $F_z=75$ pN out-of-plane force applied at the edge. Although some degree of twisting is observed, the membrane is deflected throughout, $\langle h \rangle \approx 0.6$ Å.

Example 2

The intramolecular bonded interactions for $MoS_2$ were described by the harmonic bond and inter-bond angle energy terms $$E_b = \frac{k_b}{2}(r-r_0)^2$$

and $E_\alpha = k_\alpha(\theta-\theta_0)^2$, respectively. The interaction groups and the corresponding constants are listed in Table 1 in which is listed bonded groups and constants for intramolecular interactions in $MoS_2$.

TABLE 1

| bond | Mo—S | $k_b = 81176.0 \frac{kJ}{mol\ nm^2}$ | $r_0 = 2.39$ Å |
|---|---|---|---|
| angle | Mo—S—Mo<br>S—Mo—S | $k_a = 534.16 \frac{kJ}{mol\ rad^2}$ | $\theta_0 = 84.3°$ |

As shown in panel A of FIG. 31, a 2-D modulus of 126.0 N/m obtained for the $MoS_2$ model used here is close to the lower end of the range 120-180 N/m. The 0 K bending rigidity directly calculated from the 2-D modulus Y as $\gamma = Yh_m^2/12(1-\upsilon^2)$ ($h_m \approx 3.12$ Å is the effective $MoS_2$ monolayer thickness and $\upsilon=0.29$ is the Poisson's ratio)[1] yields $\gamma=7.1$ eV.

The capacitance of a flat-plate capacitor in absence of perturbations is:

$$C_0 = \frac{\varepsilon\varepsilon_0 A}{d_0}, \tag{S1}$$

where $\varepsilon$ is the dielectric constant of the material between the plates (water, in this case), A is the total plate surface area, and $d_0 \ll \sqrt{A}$ is the distance between the plates. When an out-of-plane perturbation is applied to one of the plates, the effective corresponding capacitance is subject to perturbation. Neglecting field fringing and assuming small deflections, the perturbed capacitance is $$C = \varepsilon\varepsilon_0 \int \frac{d\Omega}{d(x,y)}, \tag{S2}$$

where $d\Omega$ is a differential element of the flexible plate area at $(x,y)$, $d(x,y)$ is the corresponding vertical distance between the element at $(x,y)$ and the solid plate, and the integral is over the entire plate surface. We set $d(x,y)=d_0+h(x,y)$, where $h(x,y) \ll d_0$ is the local (upwards) Z-deflection of the perturbed plate element. Hence, $$C = \frac{\varepsilon\varepsilon_0}{d_0} \int \frac{d\Omega}{1+\frac{h(x,y)}{d_0}} \approx \frac{\varepsilon\varepsilon_0}{d_0} \int\left(1-\frac{h(x,y)}{d_0}\right)d\Omega. \tag{S3}$$

From Eq. (S3), $$C \approx C_0 - \frac{\varepsilon\varepsilon_0}{d_0^2} \int h(x,y) d\Omega, \tag{S4}$$

where the subtrahend is the capacitance perturbation $\Delta C$. We note that $\int h(x,y)d\Omega = \langle h \rangle A$, where $\langle h \rangle$ is the average deflection for the entire perturbed plate (in our case calculable directly from the simulated atomic positions of the membrane). Therefore, for $\langle h \rangle < d_0$ this estimate is reduced to finding an equivalent flat-plate capacitor with a plate separation of $d' = d_0 + \langle h \rangle$. Thus, the relative change in capacitance is independent of the deflection profile of the flexible plate $d(x,y)$, depending only on $\langle h \rangle$ and $d_0$:

$$\frac{\Delta C}{C_0} \approx -\frac{\langle h \rangle}{d_0}. \tag{S5}$$

For a deflection $\langle h \rangle < 0$ (toward the solid plate), $$\frac{\Delta C}{C_0}$$

reverses sign, and differentiation between the directions of deflection occurs.

The ionic leakage current between the capacitor plates is estimated. Consider KCl salt of concentration n, for which $\mu_K$ and $\mu_{Cl}$ are the corresponding ion mobility values. The ionic drift current via the entire capacitor is:

$$i_i = nq(\mu_K+\mu_{Cl})\int E_z(x,y)d\Omega, \tag{S6}$$

where $$E_z(x,y) = \frac{V_0}{d(x,y)}$$

is the driving field distribution throughout the plate; $V_0$ is the capacitor bias and q is the ionic charge. Eq. (S6) is then an analog of Eq. (S2):

$$i_i = nq(\mu_K+\mu_{Cl})V_0 \int \frac{d\Omega}{d(x,y)}. \tag{S7}$$

The total current subject to deflection-induced perturbation is:

$$i_i = \frac{nwLqV_0(\mu_K+\mu_{Cl})}{d_0}\left(1-\frac{\langle h \rangle(t)}{d_0}\right). \tag{S8}$$

The total attractive force between the plates carrying opposite charges of magnitude Q due to bias $V_0$ is:

$$F_0 = \frac{1}{2}QV_0/d_0 = \frac{\varepsilon\varepsilon_0 wLV_0^2}{2d_0^2}. \tag{S8}$$

For the exact dimensions of the simulated membrane of L=15.5 nm, w=4.5 nm, with $d_0=1.0$ nm, $\varepsilon=80$, and $V_0=0.15$ V, we obtain $F_0 \sim 555$ pN, distributed throughout the entire membrane area. Maximum deflection of the membrane with fixed edges and an out-of-plane load $F_0$ homogeneously distributed throughout the membrane is $$h_{max} = \frac{F_0 L^3}{384 \gamma w},$$

where γ is the bending rigidity of the material—half the deflection for the case of $F_0$ concentrated at the center. Given that the deflection in response to ~75 pN (concentrated at the center) arising from hydrogen bonds has already been simulated at ~0.5 Å, and finally noting that $\langle h \rangle \approx 0.5\, h_{max}$ the pre-deflection due to inter-plate attraction is $\langle h \rangle_0 \approx 0.5$ Å×0.5×(555/75)=1.85 Å, such that the geometrically selected plate separation (as calculated at the supported ends of the membrane) should be $d_0 + \langle h \rangle_0 = 1.185$ nm to yield $d_0 = 1.0$ nm used in our electrostatics estimates. The small plate separation and the bias voltage of 150 mV were selected to produce a reasonable capacitance value and the corresponding charge perturbation $\delta Q = V_0 C_0 \langle h \rangle / d_0$ of at least a few electron charges, given the small system size and thus the quantized nature of the charge transfer process.

By rescaling the device toward more realistic dimensions, this pre-deformation effect can be greatly diminished. For example, with L=100 nm, w=75 nm, $d_0$=25 nm, the new capacitance value is estimated at 212 aF, while the voltage can be selected at 50 mV, which leads to an inter-plate force of only 10 pN. The expected average deflection $\langle h \rangle$ from breaking a C-G pair for this membrane is estimated at ~2 nm<<$d_0$.

The data in FIG. 26 and analytical calculations can be used to provide a rough estimate of the threshold electrolyte concentration, beyond which one cannot rely on the capacitive effect in a DC circuit. Per each deflection event, two displacement current peaks occur, per $$i_d(t) = V_0 \frac{dC(t)}{dt}:$$

one during while the membrane deflects, and one when it snaps back. The timescale of the former is associated with the translocation rate, while the timescale of the latter process is governed entirely by the membrane material properties and size, as well as the damping properties of the solvent. For both processes, the displacement current is proportional to the rate, at which the capacitance changes and in the following we only consider the deflecting part, while the snap-off process, leading to the second peak, can be evaluated in a similar manner. Per Eq. (S5), the current peak magnitude (in absence of noise) is:

$$i_{d,peak} = \frac{V_0 C_0}{d_0} \frac{d\langle h \rangle}{dt} = \frac{\varepsilon \varepsilon_0 w L V_0}{d_0^2} \frac{d\langle h \rangle}{dt}. \quad (S9)$$

By noting that $\langle h \rangle \approx h_{max}/2$ and $$\frac{dh_{max}}{dt} \approx u_t,$$

where $u_t$ is the translocation speed, we obtain.

$$i_{d,peak} \approx \frac{\varepsilon \varepsilon_0 w L V_0 u_t}{2 d_0^2}. \quad (S10)$$

The ionic current mostly contributes a considerable baseline shift, but also fluctuates because of deflection (per Eq. (S8))—proportional to $\langle h \rangle$ and not $d\langle h \rangle/dt$. The magnitude of this current fluctuation is of interest. Its peak occurs at the maximum average detection $\langle h \rangle_{max}$ (immediately prior to base-pair breakage) and the corresponding magnitude is:

$$i_{i,peak} \approx \frac{n w L q V_0 (\mu_K + \mu_{Cl}) \langle h \rangle_{max}}{d_0^2}. \quad (S11)$$

The peaks given by Eqs. (S10) and (S11) differ by phase, but their magnitudes can be directly compared to determine the electrolyte concentration, at which the displacement current peak from deflecting the membrane no longer dominates. By setting $$\frac{i_{i,peak}}{i_{d,peak}} > 1,$$

we obtain:

$$n > \frac{2 \varepsilon \varepsilon_0 u_t}{q (\mu_K + \mu_{Cl}) \langle h \rangle_{max}}, \quad (S12)$$

where membrane size dependence enters only via $\langle h \rangle_{max} \propto L^3/w$. Given direct proportionality to $u_t$, capacitance-based detection favors fast translocation in the DC-bias case. Assuming ionic mobility of the single-charged K$^+$ and Cl$^-$ ions of $$\sim 8 \times 10^{-8} \frac{m^2}{V \cdot s}, \langle h \rangle_{max} = 0.5 \text{ Å},$$

and $u_t$=5 cm/s, we estimate that with n>0.1 M, ionic leakage starts to dominate charge transfer in the system, masking the deflection-induced current peak. With increasing membrane dimensions (and thus generally increasing $\langle h \rangle_{max}$) this threshold decreases as $1/\langle h \rangle_{max}$.

Example 3

A sequencer includes a water-immersed nucleobase-functionalized suspended graphene nanoribbon here is selective for nucleotide detection. The proposed sensing method combines Watson-Crick selective base pairing with graphene's capacity for converting anisotropic lattice strain to changes in an electrical current at the nanoscale.

Here, we report on utilizing graphene's electronic properties, effectively combined with the Watson-Crick base-pairing, as a possible method of high-speed DNA sequencing at ambient conditions in aqueous environment. A graphene nanoribbon (GNR) with a nanoscale opening, the interior of which is chemically functionalized with selected nucleobases. As shown in panel A of FIG. 32, a single-strand DNA (ssDNA) molecule is inserted into the functionalized pore and translocated at a prescribed rate perpendicularly to the GNR. When a base complementary to the GNR's functional group traverses the pore during translocation, selective hydrogen bond formation is expected to occur, as shown in panel B of FIG. 32 with dwell time for a prescribed translocation rate. Because of local DNA-GNR binding, the GNR is pulled upon and deflected in the out-of-plane direction, followed by a slip when the critical force required for breaking the hydrogen bonds is reached. The effect of deflection-induced strain on the electronic properties of the GNR is used to detect a temporary change in the electrical current (from the electrical bias, as sketched in panel A of FIG. 32. Therefore, temporary changes in the electrical current can serve as electrically measurable nucleobase detection events. Given that C/G-functionalized GNR is a G/C-selective, while an A/T-functionalized GNR is T/A-selective, vertically stacking a total of four independently biased and appropriately functionalized GNRs would result in an integrated sequence detector.

Here, results of carefully designed atomistic molecular dynamics (MD) simulations of the continuous ssDNA translocation through a C-functionalized GNR in an aqueous environment are presented. The simulation results provide selectivity of detecting G nucleobases in terms of the effective GNR deflection at room temperature.

Shown in panel A of FIG. 33 is the central portion of the sensor, which consists of a $L_x$=4.5 nm×$L_y$=15.5 nm GNR with a ~2.5 nm-wide nanopore, whose interior is functionalized with three cytosine molecules. The GNR is position-restrained at the ends, mimicking suspension between solid electrodes. The carbon atom at position six in the cytosine molecule was covalently attached to an edge carbon in the pore of the functionalized GNR (FGNR), as seen in the magnification in panel A of FIG. 33. Such an attachment point keeps the hydrogen-bonding groups facing the interior of the nanopore, and thus available for interaction with the side-chains of the nucleotides subject to sensing. The atomic-level geometry of the cytosine-functionalized region, including the near-90° orientation of the cytosine moiety relative to the graphene plane, was obtained from a DFT energy optimization of an anthracene molecule, functionalized by the cytosine moiety at position nine. As shown in panel B of FIG. 33, six-residue ssDNA samples (sequences defined further) periodic in the Z-direction was inserted into the nanopore, as shown in panel C of FIG. 33. DNA backbones were pre-stretched in the Z-direction by a force of ~0.1 nN to promote strand linearity. In addition, weak positional restraint in the XY-plane was applied to the ssDNA backbone, so it on average remained close to the center of the nanopore, essentially mimicking a precision aperture. All MD simulations of the DNA translocation process were performed at ambient conditions (T=300 K, p=0.1 MPa). The DFT optimization of the GNR functional region was performed with the use of Gaussian 09 at the B3LYP/6-31+G(d) theory level. Partial atomic charges in the functional group were calculated per the CHELPG scheme at the HF/6-31+G(d) theory level for the optimized geometry. The MD models of the ssDNA and the FGNR were based on the OPLS-AA forcefield. The intramolecular interaction parameters for graphene were obtained from the optimized bond-order potential for carbon. As shown in panel C of FIG. 33, the system was immersed in a rectangular box filled with water described by the TIP4P model. Prior to the production MD runs, the systems were carefully pre-relaxed in NPT simulations at T=300 K and p=0.1 MPa, while the production simulations of DNA translocation were performed in an NVT ensemble at T=300 K, using GROMACS v. 5.0.5 software.

The results obtained in a simulated ssDNA translocation aimed at sensing the G residues by a C-functionalized GNR are discussed next. We used two arbitrarily selected six-residue periodic sequences of GAAGCT (SEQ1) and TCGAAC (SEQ2) translocated in the negative-Z direction at a constant rate of 5 cm/s, as dictated by the MD time limitations for a system of this size. The FGNR in all cases was pre-stretched at the ends (along the Y-axis) by 0.5% to enable a rapid return to post-deflection unperturbed state and to somewhat suppress the thermal fluctuations. The total simulated time was 300 ns, during which the sequences translocated through the pore were repeated approximately 3.3 times. In the case of SEQ1, this effectively corresponds to GAAGCT|GAAGCT|GAAGCT|GA (SEQ ID NO: 3), and thus seven passes of the G residue are expected. For SEQ2, the corresponding sequence is TCGAAC|TCGAAC|TCGAAC|TC (SEQ ID NO: 4) with three expected passes of G. Note that the nucleobase inside the pore at the start of a simulation (underlined) can vary, because the pre-translocation MD relaxation steps for the various systems discussed here allowed for spurious translocation of the sample ssDNA. As seen further, the variation in the starting residue does not affect the clarity of our observations, as we effectively track the passage of the G-bases. Shown in panel A of FIG. 34 we present the results of SEQ1 translocation in the form of the out-of-plane deflection of the GNR as a function of simulated time, shown alongside the number of hydrogen bonds formed between the functional groups and the G residues in the tested ssDNA. The latter measure enables clear tracking of the residue of interest, as it passes through the pore. A total of seven binding events occur between the functional groups at the pore interior and the residues of interest. A total of three hydrogen bonds are created in each case, as shown in panel A of FIG. 34. In six out of the seven G-passage events, the bond formation is accompanied by a clear GNR out-of-plane deflection of the average ~2 Å magnitude, followed in each case by a sharp slip when the critical force required for breaking the G-C hydrogen bonds was reached. The clearly missed event is located at t≈100 ns. As observed in panel E of FIG. 34, the pulling force in the range 50-80 pN, consistent with the experimentally measured 54.0-61.4 pN. Note that for a sensor aimed at detecting the A/T bases (with a T/A-functionalized GNR), the corresponding critical force would be ~⅔ of the average C-G value, reducing the corresponding deflection magnitude accordingly. In panel B, D, and F of FIG. 34, the same data is presented for SEQ2. Similarly, the passage of the G-nucleobase is accompanied by a temporary GNR deflection. No post-processing of the deflection data was performed beyond basic low-pass filtering with a bandwidth of 500 MHz. Such filtering allowed effective removal of thermal noise, as well as clear resolution of the deflection events, which, from the presented data, took ~15 ns on average, thus corresponding to an effective frequency of ~66 MHz.

The intended ssDNA-FGNR chemical coupling can be seen in FIG. 35, where a representative deflected state of the FGNR immediately prior to pull-off is shown. The interacting groups are properly oriented and the hydrogen bonds are formed between the functional group at the nanopore edge and the passing G-base. No false-positives occurred during simulated translocation, likely due to no significant hydrogen bond formation between the FGNR and the non-guanine nucleobases in the test sample. This cause for the demonstrated level of selectivity is supported by the data in panels C and D FIG. 34, where spurious hydrogen bonds are tracked throughout the simulated time alongside the intended (FGNR-G) bonds.

The translocation rate can affect the device performance in terms of the bond formation and the overall system relaxation, resulting in effects on the noise, and nucleobase selectivity. We performed translocation tests of SEQ1 at a significantly higher rate of 25 cm/s, corresponding approximately to 330 million nucleobases per second, simulated for 60 ns. The resulting FGNR deflection and the number of C-G hydrogen bonds as functions of time are shown in FIG. 36. Although C-G bonds continue to form between the FGNR and the passing ssDNA, and the average deflection magnitude is higher (likely due to lack of system relaxation. We observe a noisy resolution of the G passage at t≈10 ns and a missed event at t≈35 ns.

Combined data in panels A and B of FIG. 34 provide an overall single-sensor detection error probability near 1/10 for the 5 cm/s translocation rate. Given that no false positives were observed, one roughly estimates that a total of four independent measurements would be required to achieve a 99.99% fidelity at the translocation rate of 5 cm/s. In addition, given that an experimental setup would likely use even lower translocation speeds, the overall single-measurement error rate may be further improved.

Nucleotide passage can be detected in an atomic force microscopy-like setup by tracking the deflections directly, or by monitoring the FGNR-DNA interaction forces. However, direct electronic detection of the nanoscale deflection is a highly attractive option. Assuming negligible contact resistance and positing that thermally activated carriers in the conduction band dominate at T=300 K, the Landauer formalism yields a relative change in electrical resistance of a GNR of the order $$\frac{\Delta R}{R} \approx \frac{\Delta E_{gap}}{kT},$$

where R is the electrical resistance, $\Delta E_{gap}$ is the energy bandgap modulation at the Dirac point due to the deflection-induced uniaxial strain (regardless of the existing bandgap in an undeflected state due to GNR edge type, width, etc.) and k is the Boltzmann constant. A tight-binding estimate for the effect of uniaxial strain $\varepsilon$ is $\Delta E_{gap} \propto 3t_0\varepsilon$ ($t_0 \approx 2.7$ eV is the nearest-neighbor electron hopping energy for graphene). For a GNR of length L deflected by h<<L, $\varepsilon \approx 2(h/L)^2$, and thus for the FGNR dimensions and h=2 Å in this work, we estimate $\varepsilon$=0.033%, yielding a positive $$\frac{\Delta R}{R} = 10.4\%$$

due to the largeness of the ($t_0$/kT) ratio, and thus resulting in an appreciable average current decrease.

If, depending on the GNR, coherent transport dominates the conductive process, the effect of strain on an ungated GNR would be negligible. Thus, an effective use of a gate electrode was suggested, which enables modification of the carrier transmission probability and results in an effective relative change in conductance of the order ($h^2/L\alpha_0$), where $\alpha_0$=1.42 Å is the C—C bond length in graphene. The latter estimate yields a relative change of ≈2% for the deflected GNR considered here. The deflection-to-length ratio is $$\frac{h}{L} \sim (F_c/w)^{1/3},$$

where w is the GNR width and $F_c$ is the critical C-G shearing force, and thus the amount of deflection could be increased in a longer and wider GNR with a somewhat higher aspect ratio. For instance, a 10 nm×60 nm GNR would be deflected (at $F_c$=const) by ≈6.4 Å, thus resulting in a relative average current shift by ≈4.8%. In a GNR with the original dimensions and without lateral pre-strain, the two detection mechanisms discussed above yield a relative change in resistance of 71% and 12%, respectively.

Ripple scattering strength is decreased because of deflection-induced strain. Therefore, if ripple scattering is expected to significantly contribute to the overall resistance in each GNR, the observed effect may become a contributing mechanism, suggesting an additional design consideration in terms of the GNR dimensions, edge type, and doping parameters. The rippling process is intrinsically dynamic in suspended atomically thin membranes, causing significant rippling mean-square variation in the time domain. This suggests a temporal modulation of the local electron hopping parameters, and thus an additional source of rippling-induced noise. However, because the timescale of the ripple dynamics is fundamentally linked to the flexural wave propagation velocity in graphene of the order of kilometers per second, the dynamic modulation of current occurs at the picosecond timescale. Thus, given that the timescale of the deflection-induced signal is of the order of tens of nanoseconds for the translocation rate of 5 cm/s (~15 ns/base), low-pass signal filtering should be sufficient to eliminate the high-frequency current noise arising from the FGNR fluctuations.

Example 4

Equations are number beginning at S1 in this Example.

A relative variation of the electrical current around the baseline values due to deflection-induced strains can be estimated at the order-of-magnitude level for idealized cases. Furthermore, the nanomechanical deflections reported in the main text are for a zigzag-edged GNR and are generally valid for armchair GNRs of similar dimensions. Therefore, our discussion of the strain value estimates is not necessarily limited to the GNR type used in our MD simulations. Further, as seen in Eq. (S4) below and mentioned in the main text, a similar nanomechanical response can be obtained from GNRs of varying length and width (provided some requirements on the aspect ratio are met), thus allowing a degree of freedom in varying the dimensions, crucial for the design of the GNR properties in absence of strain. Here we briefly present the basic mechanisms underlying the effect of uniaxial strains on the electronic properties of GNRs, while the numerical estimates are provided in section S2.

The resistance of a GNR at a given appropriately selected bias point, excluding contact resistance for clarity, in the thermally activated regime is approximated as [9]:

$$R = \frac{R_0}{|t|^2}\left(1 + e^{-\frac{E_{gap}}{kT}}\right), \quad (S1)$$

where $R_0$ is the quantum resistance unit, $|t|^2$ is the effective transmission probability for electrons with a given energy E (as dictated by the bias), such that $|E-E_F|>E_{gap}$ ($E_F$ and $E_{gap}$ are the Fermi level and the bandgap, as determined by the GNR dimensions, edge, etc., respectively), and T is the temperature. In the thermally activated conduction regime expected to dominate the water-immersed GNR at room temperature, the effect of strain is primarily due to modification of the number of carriers proportional to e $$-\frac{E_{gap}}{kT}$$

via strain-induced change of $E_{gap}$, resulting in $$\frac{\delta R}{R} \approx \frac{\delta E_{gap}}{kT}$$

(independent of $E_{gap}$ itself in the perturbative approximation), where $\delta E_{gap} \approx 3 t_0 \varepsilon$, ($t_0 \approx 2.7$ eV is the nearest-neighbor electron hopping energy for graphene, $\varepsilon$ is the strain), thus yielding $$\frac{\delta R}{R} \approx \frac{3 t_0 \varepsilon}{kT}.$$

For completeness, in the T=0 K limit, Eq. (S1) is effectively replaced by the coherent transport term:

$$R = \frac{R_0}{|t|^2} \quad (S2)$$

and the effect of strain is via modification of the effective (quantized) transmission probability $|t|^2$. In this case, the effect of strain on a gateless GNR is negligible. However, around an appropriately selected bias point, strain can indeed be detected in an interferometer-type measurement setup with a relative variation of R estimated at $$\frac{\delta R}{R} = -\frac{\delta |t|^2}{|t|^2} \approx \frac{h^2}{La_0},$$

where h is the out-of-plane deflection, L is the effective GNR length, and $a_0$ is the C—C interatomic distance in graphene.

As a rough estimate, the maximum out-of-plane deflection h of an edge-clamped GNR of length L due to force F applied at L/2 is the solution of the following cubic equation:

$$F = \frac{2 E_{2D} w h}{L^2}\left(\varepsilon_0 L + \frac{2 h^2}{L}\right), \quad (S3)$$

where $E_{2D}$, w, and $\varepsilon_0$ are the two-dimensional Young's modulus of graphene, GNR width, and the initial pre-strain along the GNR length, respectively. A reasonable agreement with the simulated data was obtained with $E_{2D} \approx (E_{3D} h_0) = 106$ N/m, where $E_{3D} = 1.06$ TPa and $h_0 = 0.1$ nm are the 3-D Young's modulus of graphene and its effective "continuum" thickness, respectively.

For L=15.5 nm, F=75 pN, and $\varepsilon_0$=0.5%, Eq. (S3) yields h=2.24 Å. Without pre-strain ($\varepsilon_0$=0), the central deflection is:

$$h = L\left(\frac{F}{4 E_{2D} w}\right)^{1/3}, \quad (S4)$$

yielding $h_{\varepsilon_0=0}$=5.27 Å. The deflection-induced strain in this case is $$\varepsilon \approx 2\left(\frac{h}{L}\right)^2 = 0.23\%,$$

which causes an estimated $$\frac{\delta R}{R} \approx \frac{\delta E_{gap}}{kT} = \frac{3 t_0 \varepsilon}{kT} = 71\% \text{ and } \frac{\delta R}{R} \approx \frac{h^2}{La_0} = 12\%,$$

per Eqs. (S1) and (S2), respectively. For the A-T binding with a critical force of F=50 pN, $h_{\varepsilon_0=0}$=4.60 Å, yielding the $$\frac{\delta R}{R}$$

estimates of 32% and 5.3%, per Eqs. (S1) and (S2), respectively.

With $E_{2D}$=352 N/m [13], Eq. (S3) underestimates the deflections obtained in our simulations with $\varepsilon_0$=0.5%. However, with lower $\varepsilon_0$, it yields deflections of comparable magnitude, and thus all the estimates made here remain valid. For example, with $E_{2D}$=352 N/m and $\varepsilon_0$=0.1%, we obtain a deflection value of 1.9 Å for the C-G pair, and thus identical $$\frac{\delta R}{R}$$

estimates. Without pre-strain, the maximum deflection per Eq. (S2) is $h_{\varepsilon_0=0}$=3.1 Å, and thus $$\frac{\delta R}{R} \approx \frac{\delta E_{gap}}{kT} = \frac{3 t_0 \varepsilon}{kT} = 24\%$$

from Eq. (S1). Within the approximations made, these estimates are valid for GNRs of appropriately scaled dimensions.

A very narrow GNR, such as the one used in our simulations, would present a region of locally reduced conductance in the nanopore region, given the closeness of the pore edge to the GNR edge. An additional effect on the electrical conductivity thus would arise from the local strain inhomogeneity near the pore.

An estimate of the time-averaged effect of the ripples can be obtained from considering them as carrier scatterers, which leads to an overall increase of the electrical resistivity, in addition to the temporal modulation of the current. In the long-wave approximation, this excess resistivity $\rho_r$ increases with the rippling strength (e.g., in terms of the mean-square out-of-plane displacement $\langle h^2 \rangle$), while its size-scaling properties depend on the rippling Fourier scaling law $h_q^2$. Here, we discuss the qualitative effect of FGNR rippling on $\rho_r$ during DNA translocation by considering the wave-vector distributions $h_q^2$ and the $\langle h^2 \rangle$ averages, as obtained during the passage of G and non-G residues through the FGNR. Shown in FIG. 37 are the $h_q^2$ distributions for the FGNR at T=300 K, along with the raw rippling data in the corresponding inset. As shown, the distributions are similar during the passage of G and non-G residues, although the rippling strength during G passage is consistently lower. The latter is expected, because even the relatively faint lateral strain can significantly suppress thermal flexural fluctuations. Direct calculations of $\langle h^2 \rangle$ ($\propto \int h_q^2 d\Omega_q$, where $d\Omega_q$ is an area element in the 2-D reciprocal space) confirm this observation, yielding a decrease from 1.63 Å$^2$ to 1.35 Å$^2$ during the passage of non-G and G, respectively. An accurate quantitative estimate of $\Delta \rho_r/\rho_r$ due to FGNR deflection induced strain would crucially depend on the dimensions, as well as the fabrication methods of an experimentally relevant GNR. However, the relatively high sensitivity of the ripple scattering mechanism to $\langle h^2 \rangle$ (and thus to deflection-induced strain) can be revealed via previously estimated $\rho_r \propto n_r/n_c$, where $n_r \propto \langle h^2 \rangle^2$ and $$n_c \propto e^{-\frac{E_{gap}}{kT}}$$

is the effective sheet density of the scatterers and charge carriers, respectively. Because of excess strain due to G-induced FGNR deflection, $$\frac{\Delta \rho_r}{\rho_r} \propto \frac{\Delta n_r}{n_r} - \frac{\Delta n_c}{n_c}.$$

Here, $n_r \propto \langle h^2 \rangle^2$ is considerably reduced (by ~30%, from the $\langle h^2 \rangle$ estimates above) and $$\Delta n_c/n_c \propto -\frac{3t_0 \varepsilon}{kT} < 0$$

due to strain-induced bandgap modulation, estimated at ~10% above. The net result of this competition between strain-induced decreased scattering and a decrease in the number of charge carriers is reduction of $\rho_r$ by ~20%. Therefore, if ripple scattering is expected to significantly contribute to the overall resistance in each GNR, the described effect of strain-induced ripple suppression may become an additional mechanism contributing to the net current variation.

For the t-th MD frame, an individual $h_q^2$ distribution was calculated directly from the atomic population of the FGNR as the corresponding 2-D Fourier transform of $(z_i - \bar{z}_t)^2$, where $z_i$ is the i-th atom's position along Z and $\bar{z}_t$ is the local plane level at time t. The distributions $h_q^2$ were presented as averages of distributions over multiple frames for each translocation portion (G and non-G).

The t-th per-frame average from N atoms in the GNR is $$\langle h_t^2 \rangle = \frac{1}{N-1} \sum_N (z_i - \bar{z}_t)^2, \quad (S5)$$

and the grand average per multiple frames is calculated as $$\langle h^2 \rangle = \frac{1}{\tau} \sum_\tau \langle h_t^2 \rangle.$$

Note that for a membrane deflected at the center, the use of a global "plane level"

$$\bar{z}_t = \frac{1}{N} \sum_N z_i$$

is incorrect. Therefore, we used the local plane level $\bar{z}_{t,i}$ equal to the per-atom running time-average obtained from an infinite impulse response (IIR) filter. Ripple suppression was independently confirmed by using Eq. (S5), while calculating $\bar{z}_{t,i}$ from a second-order polynomial surface fit at every MD frame. The data in FIG. S1 and the grand averages discussed in section S4 were calculated over τ=20 ns long periods of G and non-G translocation. The frame spacing was 50 ps, resulting in a total of 400 frames used in the averaging for each passage.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A nucleic acid sequencer to electrically determine a sequence of nitrogenous bases in a single stranded nucleic acid, the nucleic acid sequencer comprising:
   an atomically thin membrane;
   a solid electrode spaced apart from the atomically thin membrane and arranged in a capacitive configuration with the atomically thin membrane;
   a spacer member interposed between the atomically thin membrane and the solid electrode and comprising:
      a first surface on which the atomically thin membrane is disposed; and
      a second surface on which the solid electrode is disposed, such that the spacer member provides a selected distance between the atomically thin membrane and the solid electrode;
   a complementary base covalently disposed on the atomically thin membrane and arranged to base pair with a nitrogenous base of the single stranded nucleic acid;
   a power source in electrical communication with the solid electrode and that provides electrical power to the solid electrode; and
   a resistor in electrical communication with the power source and that receives electric current from the power source and that also is in electrical communication with the atomically thin membrane such that an amount of the electric current changes in response to a change in the selected distance between the atomically thin membrane and the solid electrode.

2. The nucleic acid sequencer of claim 1, wherein the atomically thin membrane comprises a first atomically thin membrane, and
   the complementary base comprises a first complementary base covalently disposed on the first atomically thin membrane.

3. The nucleic acid sequencer of claim 2, wherein the atomically thin membrane further comprises a second atomically thin membrane, and
   the complementary base further comprises a second complementary base covalently disposed on the second atomically thin membrane,
   wherein the first atomically thin membrane and the second atomically thin membrane are spaced apart, and
   the first complementary base is different than the second complementary base.

4. The nucleic acid sequencer of claim 3, wherein the atomically thin membrane further comprises a third atomically thin membrane, and
   the complementary base further comprises a third complementary base covalently disposed on the third atomically thin membrane,
   wherein the first atomically thin membrane, the second atomically thin membrane, and the third atomically thin membrane are spaced apart, and
   the first complementary base and the second complementary base are different than the third complementary base.

5. The nucleic acid sequencer of claim 4, wherein the atomically thin membrane further comprises a fourth atomically thin membrane, and
   the complementary base further comprises a fourth complementary base covalently disposed on the fourth atomically thin membrane, wherein the first atomically thin membrane, the second atomically thin membrane, the third atomically thin membrane and the fourth atomically thin membrane are spaced apart, and the first complementary base, the second complementary base, and the third complementary base are different than the fourth complementary base.

6. The nucleic acid sequencer of claim 1, wherein the atomically thin membrane comprises carbon, molybdenum, oxygen, sulfur, or a combination comprising at least one of the foregoing elements.

7. The nucleic acid sequencer of claim 6, wherein the atomically thin membrane comprises carbon arranged as graphene.

8. The nucleic acid sequencer of claim 6, wherein the atomically thin membrane comprises molybdenum and sulfur arranged as molybdenum disulfide.

9. The nucleic acid sequencer of claim 1, wherein the atomically thin membrane comprises an aperture through which to communicate the single stranded nucleic acid.

10. The nucleic acid sequencer of claim 9, wherein a first complementary base is covalently disposed on the aperture.

11. The nucleic acid sequencer of claim 9, wherein a second complementary base is covalently disposed on a peripheral edge of the atomically thin membrane.

12. The nucleic acid sequencer of claim 1, wherein the complementary base is covalently disposed on a peripheral edge of the atomically thin membrane.

13. The nucleic acid sequencer of claim 1, wherein the solid electrode comprises degenerately doped silicon, copper, gold, or a combination comprising at least one of the foregoing electrode materials.

14. The nucleic acid sequencer of claim 1, wherein the solid electrode comprises an aperture through which to communicate the single stranded nucleic acid.

15. The nucleic acid sequencer of claim 1, wherein the spacer member comprises silica, undoped silicon, or a combination comprising at least one of the foregoing spacer member materials.

16. The nucleic acid sequencer of claim 1, wherein the complementary base comprises an adenine, a cytosine, a guanine, a thymine, a uracil, 2,4-diaminopyrimidine, or a combination comprising at least one of the foregoing nucleobases.

17. The nucleic acid sequencer of claim 1, wherein the base pair comprises a Watson-Crick base pair, a wobble base pair, or an unnatural base pair.

18. The nucleic acid sequencer of claim 1, further comprising an alignment member that receives the single stranded nucleic acid and comprises an alignment aperture through which the single stranded nucleic acid is communicated and that aligns the single stranded nucleic acid with the complementary base covalently disposed on the atomically thin membrane.

19. The nucleic acid sequencer of claim 1, wherein the solid electrode is electrically conductive.

20. The nucleic acid sequencer of claim 1, wherein the atomically thin membrane comprises a bending modulus from 80 electron volts (eV) to 110 eV.

* * * * *

SEQUENCE LISTING

```
<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: probe
```

```
<400> SEQUENCE: 1
acgtacgtac gt                                                           12

<210> SEQ ID NO 2
<211> LENGTH: 20
<212> TYPE: DNA
<213> ORGANISM: Artificial Sequence
<220> FEATURE:
<223> OTHER INFORMATION: probe

<400> SEQUENCE: 2
tgaagctgaa gctgaagctg                                                   20

<210> SEQ ID NO 3
<211> LENGTH: 20
<212> TYPE: DNA
<213> ORGANISM: Artificial Sequence
<220> FEATURE:
<223> OTHER INFORMATION: probe

<400> SEQUENCE: 3
gaagctgaag ctgaagctga                                                   20

<210> SEQ ID NO 4
<211> LENGTH: 20
<212> TYPE: DNA
<213> ORGANISM: Artificial Sequence
<220> FEATURE:
<223> OTHER INFORMATION: probe

<400> SEQUENCE: 4
tcgaactcga actcgaactc                                                   20
```